(12) United States Patent
Monia et al.

(10) Patent No.: US 7,414,033 B2
(45) Date of Patent: Aug. 19, 2008

(54) MODULATION OF DIACYLGLYCEROL ACYLTRANSFERASE 1 EXPRESSION

(75) Inventors: Brett P. Monia, Encinitas, CA (US); Mark J. Graham, San Clemente, CA (US)

(73) Assignee: Isis Pharmaceuticals, Inc., Carlsbad, CA (US)

(*) Notice: Subject to any disclaimer, the term of this patent is extended or adjusted under 35 U.S.C. 154(b) by 460 days.

(21) Appl. No.: 10/803,482

(22) Filed: Mar. 18, 2004

(65) Prior Publication Data

US 2004/0209838 A1 Oct. 21, 2004

Related U.S. Application Data

(63) Continuation-in-part of application No. 10/394,808, filed on Mar. 21, 2003, now abandoned.

(51) Int. Cl.
*A61K 31/70* (2006.01)
*C07H 21/02* (2006.01)
*C07H 21/04* (2006.01)
*C12Q 1/68* (2006.01)

(52) U.S. Cl. ............... 514/44; 536/23.1; 536/24.1; 536/24.5; 435/6; 435/375; 435/377

(58) Field of Classification Search ............... None
See application file for complete search history.

(56) References Cited

U.S. PATENT DOCUMENTS

| | | | |
|---|---|---|---|
| 5,708,160 A * | 1/1998 | Goh et al. ............... 536/24.32 |
| 5,998,148 A * | 12/1999 | Bennett et al. ............... 435/6 |
| 6,100,077 A | 8/2000 | Sturley et al. |
| 6,344,548 B1 | 2/2002 | Farese, Jr. et al. |
| 6,444,427 B1 | 9/2002 | Ludwig et al. |
| 6,512,099 B2 | 1/2003 | Omura et al. |
| 6,607,893 B2 | 8/2003 | Ramharack et al. |
| 6,822,141 B2 | 11/2004 | Lardizabal et al. |
| 6,867,039 B2 * | 3/2005 | Monia et al. ............... 435/375 |
| 2002/0119138 A1 | 8/2002 | Cases et al. |
| 2002/0127627 A1 | 9/2002 | Ramharack et al. |
| 2002/0193315 A1 | 12/2002 | Omura et al. |
| 2003/0028923 A1 | 2/2003 | Lardizabal et al. |
| 2003/0073103 A1 | 4/2003 | Ludwig et al. |
| 2003/0100480 A1 | 5/2003 | Smith et al. |
| 2003/0104414 A1 | 6/2003 | Attersand |
| 2003/0115632 A1 | 6/2003 | Lardizabal et al. |
| 2003/0124126 A1 | 7/2003 | Cases et al. |
| 2003/0152574 A1 | 8/2003 | Logan et al. |
| 2003/0161831 A1 | 8/2003 | Cases et al. |
| 2003/0170691 A1 | 9/2003 | Gimeno et al. |
| 2003/0200563 A1 | 10/2003 | Butler et al. |
| 2003/0202968 A1 | 10/2003 | Cases et al. |
| 2004/0054177 A1 | 3/2004 | Otake et al. |
| 2004/0058820 A1 | 3/2004 | Hagmann et al. |
| 2004/0076977 A1 | 4/2004 | Georges et al. |
| 2004/0078836 A1 * | 4/2004 | Farese et al. ............... 800/14 |
| 2004/0107459 A1 | 6/2004 | Lardizabal et al. |
| 2004/0122033 A1 | 6/2004 | Nargund et al. |
| 2004/0185559 A1 | 9/2004 | Monia et al. |

FOREIGN PATENT DOCUMENTS

| | | |
|---|---|---|
| EP | 1308459 A2 | 5/2003 |
| WO | WO 99/67268 A1 | 12/1999 |
| WO | WO-00/78961 | 12/2000 |
| WO | WO-01/68848 | 9/2001 |
| WO | WO-01/77389 | 10/2001 |
| WO | WO-02/08260 | 1/2002 |
| WO | WO 02/062954 | 8/2002 |
| WO | WO 03/004630 A2 | 1/2003 |

OTHER PUBLICATIONS

Yu et al. Circulation vol. 100(18 Suppl.): 1745, Nov. 2, 1999.*
Buhman et al., "DGAT1 is not essential for intestinal triacylglycerol absorption or chylomicron synthesis", *J. Biol. Chem.* Jul. 12, 2002 277:25474-25479.
Cases et al., "Identification of a gene encoding an acyl CoA: diacylglycerol acyltransferase, a key enzyme in triacylglycerol synthesis", *Proc. Natl. Acad. Sci.* USA Oct. 27, 1998 95:13018-13023.
Cases et al., "Cloning of DGAT2, a second mammalian diacylglycerol acyltransferase, and related family members", *J. Biol. Chem.* Oct. 19, 2001 276:38870-38876.
Chen et al., "Increased insulin and leptin sensitivity in mice lacking acyl CoA: diacylglycerol acyltransferase 1", *J. Clin. Invest.* Apr. 2002 109:1049-1055.
Chen et al., "Leptin modulates the effects of acyl CoA: diacylglycerol acyltransferase deficiency on murine fur and sebaceous glands", *J. Clin. Invest.* Jan. 2002 109:175-181.
Cheng et al., "Human acyl-CoA: diacylglycerol acyltransferase is a tetrameric protein", *Biochem. J.* Nov. 1, 2001 359:707-714.
Farese et al., "Triglyceride synthesis: insights from the cloning of diacylglycerol acyltransferase", *Curr. Opin. Lipidol.* Jun. 2000 11:229-234.
Lardizabal et al., "DGAT2 is a new diacylglycerol acyltransferase gene family: purification, cloning, and expression in insect cells of two polypeptides from *Mortierella ramanniana* with diacylglycerol acyltransferase activity", *J. Biol. Chem.* Oct. 19, 2001 276:38862-38869.

(Continued)

*Primary Examiner*—Sean R McGarry
(74) *Attorney, Agent, or Firm*—McDermott Will & Emery LLP

(57) ABSTRACT

Compounds, compositions and methods are provided for modulating the expression of diacylglycerol acyltransferase 1. The compositions comprise oligonucleotides, targeted to nucleic acid encoding diacylglycerol acyltransferase 1. Methods of using these compounds for modulation of diacylglycerol acyltransferase 1 expression and for diagnosis and treatment of disease associated with expression of diacylglycerol acyltransferase 1, such as obesity and obesity-related conditions, are provided.

65 Claims, No Drawings

OTHER PUBLICATIONS

Ludwig et al., "DGAT1 promoter polymorphism associated with alterations in body mass index, high density lipoprotein levels and blood pressure in Turkish women", *Clin. Genet.* Jul. 2002 62:68-73.

Meegalla et al., "Concerted elevation of acyl-coenzyme A: diacylglycerol acyltransferase (DGAT) activity through independent stimulation of mRNA expression of DGAT1 and DGAT2 by carbohydrate and insulin", *Biochem. Biophys. Res. Commun.* Nov. 1, 2002 298:317-323.

Oelkers et al., "Characterization of two human genes encoded acyl coenzyme A: cholesterol acyltransferase-related enzymes," *J. Biol. Chem.* Oct. 9, 1998 273:26765-26771.

Smith et al., "Obesity resistance and multiple mechanisms of triglyceride synthesis in mice lacking DGAT", *Nat. Genet.* May 2000 25:87-90.

Tabata et al., "Xanthohumols, diacylglycerol acyltransferase inhibitors, from *Humulus lupulus*", *Phytochemistry* Oct. 1997 46:683-687.

Tomoda et al., "Roselipins, inhibitors of diacylglycerol acyltransferase, produced by *Gliocladium roseum* KF-1040", *J. Antibiot.* (Tokyo) Aug. 1999 52:689-694.

Waterman et al., "Distinct ontogenic patterns or overt and latent DGAT activities of rat liver microsomes", *J. Lipid. Res.* Sep. 2002 43:1555-1562.

Yu et al., "Posttranscriptional control of the expression and function of diacylglycerol acyltransferase-1 in mouse adipocytes", *J. Biol. Chem.* Dec. 27, 2002 277:50876-50884.

Chin, Andrew "On the Preparation and Utilization of Isolated and Purified Oligonucleotides." Document purportedly located on a CD-ROM and contributed to the public collection of the Katherine R. Everett Law Library of the University of North Carolina on Mar. 14, 2002.

Murray, Susan, et al., "Inhibition of DGAT1 with a Novel Optimized Antisense Inhibitor Lowers Plasma Glucose Levels," *Diabetes*, 52(Supp. 1): p. A300, XP009077409 (2003).

* cited by examiner

SEQUENCE LISTING

<160> NUMBER OF SEQ ID NOS: 231

<210> SEQ ID NO 1
<211> LENGTH: 20
<212> TYPE: DNA
<213> ORGANISM: Artificial Sequence

```
<220> FEATURE:
<223> OTHER INFORMATION: Antisense Oligonucleotide

<400> SEQUENCE: 1
tccgtcatcg ctcctcaggg                                                    20

<210> SEQ ID NO 2
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 2
gtgcgcgcga gcccgaaatc                                                    20

<210> SEQ ID NO 3
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 3
atgcattctg cccccaagga                                                    20

<210> SEQ ID NO 4
<211> LENGTH: 1976
<212> TYPE: DNA
<213> ORGANISM: H. sapiens
<220> FEATURE:
<220> FEATURE:
<221> NAME/KEY: CDS
<222> LOCATION: (245)...(1711)

<400> SEQUENCE: 4
gaatggacga gagaggcggc cgtccattag ttagcggctc cggagcaacg cagccgttgt        60
ccttgaggcc gacgggcctg acgcgggcgg gttgaacgcg ctggtgaggc ggtcacccgg       120
gctacggcgg ccggcagggg gcagtggcgg ccgttgtcta gggcccggag gtggggccgc       180
gcgcctcggg cgctacgaac ccggcaggcc cacgcttggc tgcggccggg tgcgggctga       240 ggcc atg ggc gac cgc ggc agc tcc cgg cgc cgg agg aca ggg tcg cgg       289
     Met Gly Asp Arg Gly Ser Ser Arg Arg Arg Arg Thr Gly Ser Arg
       1               5                  10                  15 ccc tcg agc cac ggc ggc ggc ggg cct gcg gcg gcg gaa gaa gag gtg       337
Pro Ser Ser His Gly Gly Gly Gly Pro Ala Ala Ala Glu Glu Glu Val
             20                  25                  30 cgg gac gcc gct gcg ggc ccc gac gtg gga gcc gcg ggg gac gcg cca       385
Arg Asp Ala Ala Ala Gly Pro Asp Val Gly Ala Ala Gly Asp Ala Pro
         35                  40                  45 gcc ccg gcc ccc aac aag gac gga gac gcc ggc gtg ggc agc ggc cac       433
Ala Pro Ala Pro Asn Lys Asp Gly Asp Ala Gly Val Gly Ser Gly His
     50                  55                  60 tgg gag ctg agg tgc cat cgc ctg cag gat tct tta ttc agc tct gac       481
Trp Glu Leu Arg Cys His Arg Leu Gln Asp Ser Leu Phe Ser Ser Asp
 65                  70                  75 agt ggc ttc agc aac tac cgt ggc atc ctg aac tgg tgt gtg gtg atg       529
Ser Gly Phe Ser Asn Tyr Arg Gly Ile Leu Asn Trp Cys Val Val Met
 80                  85                  90                  95 ctg atc ttg agc aat gcc cgg tta ttt ctg gag aac ctc atc aag tat       577
Leu Ile Leu Ser Asn Ala Arg Leu Phe Leu Glu Asn Leu Ile Lys Tyr
                100                 105                 110
```

-continued

| | |
|---|---|
| ggc atc ctg gtg gac ccc atc cag gtg gtt tct ctg ttc ctg aag gat<br>Gly Ile Leu Val Asp Pro Ile Gln Val Val Ser Leu Phe Leu Lys Asp<br>115                      120                      125 | 625 |
| ccc cat agc tgg ccc gcc cca tgc ctg gtt att gcg gcc aat gtc ttt<br>Pro His Ser Trp Pro Ala Pro Cys Leu Val Ile Ala Ala Asn Val Phe<br>130                      135                      140 | 673 |
| gct gtg gct gca ttc cag gtt gag aag cgc ctg gcg gtg ggt gcc ctg<br>Ala Val Ala Ala Phe Gln Val Glu Lys Arg Leu Ala Val Gly Ala Leu<br>145                      150                      155 | 721 |
| acg gag cag gcg gga ctg ctg ctg cac gta gcc aac ctg gcc acc att<br>Thr Glu Gln Ala Gly Leu Leu Leu His Val Ala Asn Leu Ala Thr Ile<br>160                      165                      170                      175 | 769 |
| ctg tgt ttc cca gcg gct gtg gtc tta ctg gtt gag tct atc act cca<br>Leu Cys Phe Pro Ala Ala Val Val Leu Leu Val Glu Ser Ile Thr Pro<br>                    180                      185                      190 | 817 |
| gtg ggc tcc ctg ctg gcg ctg atg gcg cac acc atc ctc ttc ctc aag<br>Val Gly Ser Leu Leu Ala Leu Met Ala His Thr Ile Leu Phe Leu Lys<br>                    195                      200                      205 | 865 |
| ctc ttc tcc tac cgc gac gtc aac tca tgg tgc cgc agg gcc agg gcc<br>Leu Phe Ser Tyr Arg Asp Val Asn Ser Trp Cys Arg Arg Ala Arg Ala<br>                    210                      215                      220 | 913 |
| aag gct gcc tct gca ggg aag aag gcc agc agt gct gct gcc ccg cac<br>Lys Ala Ala Ser Ala Gly Lys Lys Ala Ser Ser Ala Ala Ala Pro His<br>225                      230                      235 | 961 |
| acc gtg agc tac ccg gac aat ctg acc tac cgc gat ctc tac tac ttc<br>Thr Val Ser Tyr Pro Asp Asn Leu Thr Tyr Arg Asp Leu Tyr Tyr Phe<br>240                      245                      250                      255 | 1009 |
| ctc ttc gcc ccc acc ttg tgc tac gag ctc aac ttt ccc cgc tct ccc<br>Leu Phe Ala Pro Thr Leu Cys Tyr Glu Leu Asn Phe Pro Arg Ser Pro<br>                    260                      265                      270 | 1057 |
| cgc atc cgg aag cgc ttt ctg ctg cga cgg atc ctt gag atg ctg ttc<br>Arg Ile Arg Lys Arg Phe Leu Leu Arg Arg Ile Leu Glu Met Leu Phe<br>                    275                      280                      285 | 1105 |
| ttc acc cag ctc cag gtg ggg ctg atc cag cag tgg atg gtc ccc acc<br>Phe Thr Gln Leu Gln Val Gly Leu Ile Gln Gln Trp Met Val Pro Thr<br>                    290                      295                      300 | 1153 |
| atc cag aac tcc atg aag ccc ttc aag gac atg gac tac tca cgc atc<br>Ile Gln Asn Ser Met Lys Pro Phe Lys Asp Met Asp Tyr Ser Arg Ile<br>305                      310                      315 | 1201 |
| atc gag cgc ctc ctg aag ctg gcg gtc ccc aat cac ctc atc tgg ctc<br>Ile Glu Arg Leu Leu Lys Leu Ala Val Pro Asn His Leu Ile Trp Leu<br>320                      325                      330                      335 | 1249 |
| atc ttc ttc tac tgg ctc ttc cac tcc tgc ctg aat gcc gtg gct gag<br>Ile Phe Phe Tyr Trp Leu Phe His Ser Cys Leu Asn Ala Val Ala Glu<br>                    340                      345                      350 | 1297 |
| ctc atg cag ttt gga gac cgg gag ttc tac cgg gac tgg tgg aac tcc<br>Leu Met Gln Phe Gly Asp Arg Glu Phe Tyr Arg Asp Trp Trp Asn Ser<br>                    355                      360                      365 | 1345 |
| gag tct gtc acc tac ttc tgg cag aac tgg aac atc cct gtg cac aag<br>Glu Ser Val Thr Tyr Phe Trp Gln Asn Trp Asn Ile Pro Val His Lys<br>                    370                      375                      380 | 1393 |
| tgg tgc atc aga cac ttc tac aag ccc atg ctt cga cgg ggc agc agc<br>Trp Cys Ile Arg His Phe Tyr Lys Pro Met Leu Arg Arg Gly Ser Ser<br>385                      390                      395 | 1441 |
| aag tgg atg gcc agg aca ggg gtg ttc ctg gcc tcg gct ttc ttc cac<br>Lys Trp Met Ala Arg Thr Gly Val Phe Leu Ala Ser Ala Phe Phe His<br>400                      405                      410                      415 | 1489 |
| gag tac ctg gtg agc gtc cct ctg cga atg ttc cgc ctc tgg gct ttc<br>Glu Tyr Leu Val Ser Val Pro Leu Arg Met Phe Arg Leu Trp Ala Phe<br>                    420                      425                      430 | 1537 |

-continued

```
acg ggc atg atg gct cag atc cca ctg gcc tgg ttc gtg ggc cgc ttt    1585
Thr Gly Met Met Ala Gln Ile Pro Leu Ala Trp Phe Val Gly Arg Phe
        435                 440                 445 ttc cag ggc aac tat ggc aac gca gct gtg tgg ctg tcg ctc atc atc    1633
Phe Gln Gly Asn Tyr Gly Asn Ala Ala Val Trp Leu Ser Leu Ile Ile
    450                 455                 460 gga cag cca ata gcc gtc ctc atg tac gtc cac gac tac tac gtg ctc    1681
Gly Gln Pro Ile Ala Val Leu Met Tyr Val His Asp Tyr Tyr Val Leu
465                 470                 475 aac tat gag gcc cca gcg gca gag gcc tga gctgcacctg agggcctggc      1731
Asn Tyr Glu Ala Pro Ala Ala Glu Ala
480                 485 ttctcactgc cacctcaaac ccgctgccag agcccacctc tcctcctagg cctcgagtgc   1791
tggggatggg cctggctgca cagcatcctc ctctggtccc agggaggcct ctctgcccta   1851
tggggctctg tcctgcaccc ctcagggatg gcgacagcag gccagacaca gtctgatgcc   1911
agctgggagt cttgctgacc ctgccccggg tccgagggtg tcaataaagt gctgtccagt   1971
gggag                                                              1976

<210> SEQ ID NO 5
<211> LENGTH: 15
<212> TYPE: DNA
<213> ORGANISM: Artificial Sequence
<220> FEATURE:
<223> OTHER INFORMATION: PCR Primer

<400> SEQUENCE: 5
tccccgcatc cggaa                                                   15

<210> SEQ ID NO 6
<211> LENGTH: 22
<212> TYPE: DNA
<213> ORGANISM: Artificial Sequence
<220> FEATURE:
<223> OTHER INFORMATION: PCR Primer

<400> SEQUENCE: 6
ctgggtgaag aacagcatct ca                                           22

<210> SEQ ID NO 7
<211> LENGTH: 22
<212> TYPE: DNA
<213> ORGANISM: Artificial Sequence
<220> FEATURE:
<223> OTHER INFORMATION: PCR Probe

<400> SEQUENCE: 7
cgctttctgc tgcgacggat cc                                           22

<210> SEQ ID NO 8
<211> LENGTH: 19
<212> TYPE: DNA
<213> ORGANISM: Artificial Sequence
<220> FEATURE:
<223> OTHER INFORMATION: PCR Primer

<400> SEQUENCE: 8
gaaggtgaag gtcggagtc                                               19

<210> SEQ ID NO 9
<211> LENGTH: 20
<212> TYPE: DNA
```

<213> ORGANISM: Artificial Sequence
<220> FEATURE:
<223> OTHER INFORMATION: PCR Primer

<400> SEQUENCE: 9
gaagatggtg atgggatttc                                                20

<210> SEQ ID NO 10
<211> LENGTH: 20
<212> TYPE: DNA
<213> ORGANISM: Artificial Sequence
<220> FEATURE:
<223> OTHER INFORMATION: PCR Probe

<400> SEQUENCE: 10
caagcttccc gttctcagcc                                                20

<210> SEQ ID NO 11
<211> LENGTH: 1650
<212> TYPE: DNA
<213> ORGANISM: M. musculus
<220> FEATURE:
<220> FEATURE:
<221> NAME/KEY: CDS
<222> LOCATION: (96)...(1592)

<400> SEQUENCE: 11

```
ggatgaatgg aaataagtag aattaggcat acttaggata gggctcaagc cgcggcccgt       60
gaagattggg ccgcgacgag gtgcgggccg aagcc atg ggc gac cgc gga ggc         113
                                     Met Gly Asp Arg Gly Gly
                                      1               5 gcg gga agc tct cgg cgt cgg agg acc ggc tcg cgg gtt tcc gtc cag       161
Ala Gly Ser Ser Arg Arg Arg Arg Thr Gly Ser Arg Val Ser Val Gln
              10                  15                  20 ggt ggt agt ggg ccc aag gta gaa gag gac gag gtg cga gac gcg gct       209
Gly Gly Ser Gly Pro Lys Val Glu Glu Asp Glu Val Arg Asp Ala Ala
         25                  30                  35 gtg agc ccc gac ttg ggc gcc ggg ggt gac gcg ccg gct ccg gct ccg       257
Val Ser Pro Asp Leu Gly Ala Gly Gly Asp Ala Pro Ala Pro Ala Pro
     40                  45                  50 gct cca gcc cat acc cgg gac aaa gac ggg cgg acc agc gtg ggc gac       305
Ala Pro Ala His Thr Arg Asp Lys Asp Gly Arg Thr Ser Val Gly Asp
 55                  60                  65                  70 ggc tac tgg gat ctg agg tgc cat cgt ctg caa gat tct ttg ttc agc       353
Gly Tyr Trp Asp Leu Arg Cys His Arg Leu Gln Asp Ser Leu Phe Ser
                 75                  80                  85 tca gac agt ggt ttc agc aat tat cgt ggt atc ctg aat tgg tgt gtg       401
Ser Asp Ser Gly Phe Ser Asn Tyr Arg Gly Ile Leu Asn Trp Cys Val
             90                  95                 100 gtg atg ctg atc ctg agt aat gca agg tta ttt tta gag aac ctt atc       449
Val Met Leu Ile Leu Ser Asn Ala Arg Leu Phe Leu Glu Asn Leu Ile
        105                 110                 115 aag tat ggc atc ctg gtg gat cct atc cag gtg gtg tct ctg ttt ttg       497
Lys Tyr Gly Ile Leu Val Asp Pro Ile Gln Val Val Ser Leu Phe Leu
    120                 125                 130 aag gac ccc tac agc tgg cct gcc cca tgc gtg att att gca tcc aat       545
Lys Asp Pro Tyr Ser Trp Pro Ala Pro Cys Val Ile Ile Ala Ser Asn
135                 140                 145                 150 att ttt gtt gtg gct gca ttt cag att gag aag cgc ctg gca gtg ggt       593
Ile Phe Val Val Ala Ala Phe Gln Ile Glu Lys Arg Leu Ala Val Gly
                155                 160                 165 gcc ctg aca gag cag atg ggg ctg ctg cta cat gtg gtt aac ctg gcc       641
```

```
                Ala Leu Thr Glu Gln Met Gly Leu Leu Leu His Val Asn Leu Ala
                            170                 175                 180 aca atc att tgc ttc cca gca gct gtg gcc tta ctg gtt gag tct atc           689
Thr Ile Ile Cys Phe Pro Ala Ala Val Ala Leu Leu Val Glu Ser Ile
            185                 190                 195 act cca gtg ggt tcc gtg ttt gct ctg gca tca tac tcc atc atg ttc           737
Thr Pro Val Gly Ser Val Phe Ala Leu Ala Ser Tyr Ser Ile Met Phe
        200                 205                 210 ctc aag ctt tat tcc tac cgg gat gtc aac ctg tgg tgc cgc cag cga           785
Leu Lys Leu Tyr Ser Tyr Arg Asp Val Asn Leu Trp Cys Arg Gln Arg
215                 220                 225                 230 agg gtc aag gcc aaa gct gtc tct aca ggg aag aag gtc agt ggg gct           833
Arg Val Lys Ala Lys Ala Val Ser Thr Gly Lys Lys Val Ser Gly Ala
                235                 240                 245 gct gcc cag caa gct gtg agc tat cca gac aac ctg acc tac cga gat           881
Ala Ala Gln Gln Ala Val Ser Tyr Pro Asp Asn Leu Thr Tyr Arg Asp
            250                 255                 260 ctc tat tac ttc atc ttt gct cct act ttg tgt tat gaa ctc aac ttt           929
Leu Tyr Tyr Phe Ile Phe Ala Pro Thr Leu Cys Tyr Glu Leu Asn Phe
        265                 270                 275 cct cgg tcc ccc cga ata cga aag cgc ttt ctg cta cga cga gtt ctt           977
Pro Arg Ser Pro Arg Ile Arg Lys Arg Phe Leu Leu Arg Arg Val Leu
280                 285                 290 gag atg ctc ttt ttt acc cag ctt caa gtg ggg ctg atc caa cag tgg          1025
Glu Met Leu Phe Phe Thr Gln Leu Gln Val Gly Leu Ile Gln Gln Trp
295                 300                 305                 310 atg gtc cct act atc cag aac tcc atg aag ccc ttc aag gat atg gac          1073
Met Val Pro Thr Ile Gln Asn Ser Met Lys Pro Phe Lys Asp Met Asp
                315                 320                 325 tat tca cgg atc att gag cgt ctc tta aag ctg gcg gtc ccc aac cat          1121
Tyr Ser Arg Ile Ile Glu Arg Leu Leu Lys Leu Ala Val Pro Asn His
            330                 335                 340 ctg atc tgg ctt atc ttc ttc tat tgg ttt ttc cac tcc tgt ctc aat          1169
Leu Ile Trp Leu Ile Phe Phe Tyr Trp Phe Phe His Ser Cys Leu Asn
        345                 350                 355 gct gtg gca gag ctt ctg cag ttt gga gac cgc gag ttc tac aga gat          1217
Ala Val Ala Glu Leu Leu Gln Phe Gly Asp Arg Glu Phe Tyr Arg Asp
360                 365                 370 tgg tgg aat gct gag tct gtc acc tac ttt tgg cag aac tgg aat atc          1265
Trp Trp Asn Ala Glu Ser Val Thr Tyr Phe Trp Gln Asn Trp Asn Ile
375                 380                 385                 390 ccc gtg cac aag tgg tgc atc aga cac ttc tac aag cct atg ctc aga          1313
Pro Val His Lys Trp Cys Ile Arg His Phe Tyr Lys Pro Met Leu Arg
                395                 400                 405 cat ggc agc agc aaa tgg gtg gcc agg aca gga gta ttt ttg acc tca          1361
His Gly Ser Ser Lys Trp Val Ala Arg Thr Gly Val Phe Leu Thr Ser
            410                 415                 420 gcc ttc ttc cat gag tac cta gtg agc gtt ccc ctg cgg atg ttc cgc          1409
Ala Phe Phe His Glu Tyr Leu Val Ser Val Pro Leu Arg Met Phe Arg
        425                 430                 435 ctc tgg gca ttc aca gcc atg atg gct cag gtc cca ctg gcc tgg att          1457
Leu Trp Ala Phe Thr Ala Met Met Ala Gln Val Pro Leu Ala Trp Ile
440                 445                 450 gtg ggc cga ttc ttc caa ggg aac tat ggc aat gca gct gtg tgg gtg          1505
Val Gly Arg Phe Phe Gln Gly Asn Tyr Gly Asn Ala Ala Val Trp Val
455                 460                 465                 470 aca ctc atc att ggg caa ccg gtg gct gtg ctc atg tat gtc cac gac          1553
Thr Leu Ile Ile Gly Gln Pro Val Ala Val Leu Met Tyr Val His Asp
                475                 480                 485
```

```
tac tac gtg ctc aac tac gat gcc cca gtg ggg gta tga gctactgcca      1602
Tyr Tyr Val Leu Asn Tyr Asp Ala Pro Val Gly Val
            490                 495 aaggccagcc ctccctaacc tgggcctgga gttctggagg ggttcctg                1650
```

<210> SEQ ID NO 12
<211> LENGTH: 18
<212> TYPE: DNA
<213> ORGANISM: Artificial Sequence
<220> FEATURE:
<223> OTHER INFORMATION: PCR Primer

<400> SEQUENCE: 12

```
gttccgcctc tgggcatt                                                  18
```

<210> SEQ ID NO 13
<211> LENGTH: 18
<212> TYPE: DNA
<213> ORGANISM: Artificial Sequence
<220> FEATURE:
<223> OTHER INFORMATION: PCR Primer

<400> SEQUENCE: 13

```
gaatcggccc acaatcca                                                  18
```

<210> SEQ ID NO 14
<211> LENGTH: 25
<212> TYPE: DNA
<213> ORGANISM: Artificial Sequence
<220> FEATURE:
<223> OTHER INFORMATION: PCR Probe

<400> SEQUENCE: 14

```
cagccatgat ggctcaggtc ccact                                          25
```

<210> SEQ ID NO 15
<211> LENGTH: 20
<212> TYPE: DNA
<213> ORGANISM: Artificial Sequence
<220> FEATURE:
<223> OTHER INFORMATION: PCR Primer

<400> SEQUENCE: 15

```
ggcaaattca acggcacagt                                                20
```

<210> SEQ ID NO 16
<211> LENGTH: 20
<212> TYPE: DNA
<213> ORGANISM: Artificial Sequence
<220> FEATURE:
<223> OTHER INFORMATION: PCR Primer

<400> SEQUENCE: 16

```
gggtctcgct cctggaagat                                                20
```

<210> SEQ ID NO 17
<211> LENGTH: 27
<212> TYPE: DNA
<213> ORGANISM: Artificial Sequence
<220> FEATURE:
<223> OTHER INFORMATION: PCR Probe

<400> SEQUENCE: 17

```
aaggccgaga atgggaagct tgtcatc                                        27
```

<210> SEQ ID NO 18
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 18
gccgcctctc tcgtccattc                                              20

<210> SEQ ID NO 19
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 19
gagccgctaa ctaatggacg                                              20

<210> SEQ ID NO 20
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 20
acaacggctg cgttgctccg                                              20

<210> SEQ ID NO 21
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 21
ccgcccgcgt caggcccgtc                                              20

<210> SEQ ID NO 22
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 22
gcctcaccag cgcgttcaac                                              20

<210> SEQ ID NO 23
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 23
ccctgccggc cgccgtagcc                                              20

<210> SEQ ID NO 24
<211> LENGTH: 20
<212> TYPE: DNA
<213> ORGANISM: Artificial Sequence
<220> FEATURE:
<223> OTHER INFORMATION: Antisense Oligonucleotide -continued

<400> SEQUENCE: 24
ctccgggccc tagacaacgg                                              20

<210> SEQ ID NO 25
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 25
gttcgtagcg cccgaggcgc                                              20

<210> SEQ ID NO 26
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 26
cccggccgca gccaagcgtg                                              20

<210> SEQ ID NO 27
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 27
gcccatggcc tcagcccgca                                              20

<210> SEQ ID NO 28
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 28
tggctcgagg gccgcgaccc                                              20

<210> SEQ ID NO 29
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 29
ccgcaggccc gccgccgccg                                              20

<210> SEQ ID NO 30
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 30
ccgcacctct tcttccgccg                                              20

<210> SEQ ID NO 31
<211> LENGTH: 20

```
<212> TYPE: DNA
<213> ORGANISM: Artificial Sequence
<220> FEATURE:
<223> OTHER INFORMATION: Antisense Oligonucleotide

<400> SEQUENCE: 31
acgccggcgt ctccgtcctt                                              20

<210> SEQ ID NO 32
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 32
gctcccagtg gccgctgccc                                              20

<210> SEQ ID NO 33
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 33
ctgcaggcga tggcacctca                                              20

<210> SEQ ID NO 34
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 34
aggatgccac ggtagttgct                                              20

<210> SEQ ID NO 35
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 35
gcatcaccac acaccagttc                                              20

<210> SEQ ID NO 36
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 36
gccatacttg atgaggttct                                              20

<210> SEQ ID NO 37
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 37
```

```
gacattggcc gcaataacca                                              20

<210> SEQ ID NO 38
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 38
cttctcaacc tggaatgcag                                              20

<210> SEQ ID NO 39
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 39
gcagtcccgc ctgctccgtc                                              20

<210> SEQ ID NO 40
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 40
caggttggct acgtgcagca                                              20

<210> SEQ ID NO 41
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 41
ccagtaagac cacagccgct                                              20

<210> SEQ ID NO 42
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 42
ggtgtgcgcc atcagcgcca                                              20

<210> SEQ ID NO 43
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 43
cagcactgct ggccttcttc                                              20

<210> SEQ ID NO 44
<211> LENGTH: 20
<212> TYPE: DNA
<213> ORGANISM: Artificial Sequence
```

```
<220> FEATURE:
<223> OTHER INFORMATION: Antisense Oligonucleotide

<400> SEQUENCE: 44
tgagctcgta gcacaaggtg                                              20

<210> SEQ ID NO 45
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 45
cactgctgga tcagccccac                                              20

<210> SEQ ID NO 46
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 46
atgcgtgagt agtccatgtc                                              20

<210> SEQ ID NO 47
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 47
tgagccagat gaggtgattg                                              20

<210> SEQ ID NO 48
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 48
gagctcagcc acggcattca                                              20

<210> SEQ ID NO 49
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 49
tctgccagaa gtaggtgaca                                              20

<210> SEQ ID NO 50
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 50
gatgagcgac agccacacag                                              20
```

<210> SEQ ID NO 51
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 51
ctcatagttg agcacgtagt                                             20

<210> SEQ ID NO 52
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 52
cagtgagaag ccaggccctc                                             20

<210> SEQ ID NO 53
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 53
ccatccccag cactcgaggc                                             20

<210> SEQ ID NO 54
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 54
aggatgctgt gcagccaggc                                             20

<210> SEQ ID NO 55
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 55
ggtgcaggac agagccccat                                             20

<210> SEQ ID NO 56
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 56
gtgtctggcc tgctgtcgcc                                             20

<210> SEQ ID NO 57
<211> LENGTH: 20
<212> TYPE: DNA
<213> ORGANISM: Artificial Sequence
<220> FEATURE:
<223> OTHER INFORMATION: Antisense Oligonucleotide

```
<400> SEQUENCE: 57
ctcccagctg gcatcagact                                              20

<210> SEQ ID NO 58
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 58
ctacttattt ccattcatcc                                              20

<210> SEQ ID NO 59
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 59
tatcctaagt atgcctaatt                                              20

<210> SEQ ID NO 60
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 60
gcttgagccc tatcctaagt                                              20

<210> SEQ ID NO 61
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 61
ctcgtcgcgg cccaatcttc                                              20

<210> SEQ ID NO 62
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 62
cccatggctt cggcccgcac                                              20

<210> SEQ ID NO 63
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 63
cagccgcgtc tcgcacctcg                                              20

<210> SEQ ID NO 64
```

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 64
cggagccggc gcgtcacccc                                              20

<210> SEQ ID NO 65
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 65
ccacgctggt ccgcccgtct                                              20

<210> SEQ ID NO 66
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 66
cagatcccag tagccgtcgc                                              20

<210> SEQ ID NO 67
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 67
tcttgcagac gatggcacct                                              20

<210> SEQ ID NO 68
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 68
tcaggatacc acgataattg                                              20

<210> SEQ ID NO 69
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 69
cagcatcacc acacaccaat                                              20

<210> SEQ ID NO 70
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 70
```

```
aaccttgcat tactcaggat                                                 20

<210> SEQ ID NO 71
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 71
atccaccagg atgccatact                                                 20

<210> SEQ ID NO 72
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 72
agagacacca cctggatagg                                                 20

<210> SEQ ID NO 73
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 73
cagcagcccc atctgctctg                                                 20

<210> SEQ ID NO 74
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 74
gccaggttaa ccacatgtag                                                 20

<210> SEQ ID NO 75
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 75
aaccagtaag gccacagctg                                                 20

<210> SEQ ID NO 76
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 76
cccactggag tgatagactc                                                 20

<210> SEQ ID NO 77
<211> LENGTH: 20
<212> TYPE: DNA
```

```
<213> ORGANISM: Artificial Sequence
<220> FEATURE:
<223> OTHER INFORMATION: Antisense Oligonucleotide

<400> SEQUENCE: 77
atggagtatg atgccagagc                                               20

<210> SEQ ID NO 78
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 78
acccttcgct ggcggcacca                                               20

<210> SEQ ID NO 79
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 79
tggatagctc acagcttgct                                               20

<210> SEQ ID NO 80
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 80
tctcggtagg tcaggttgtc                                               20

<210> SEQ ID NO 81
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 81
ctcaagaact cgtcgtagca                                               20

<210> SEQ ID NO 82
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 82
gttggatcag ccccacttga                                               20

<210> SEQ ID NO 83
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 83
gtgaatagtc catatccttg                                               20
```

```
<210> SEQ ID NO 84
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 84
taagagacgc tcaatgatcc                                               20

<210> SEQ ID NO 85
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 85
tctgccacag cattgagaca                                               20

<210> SEQ ID NO 86
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 86
ccaatctctg tagaactcgc                                               20

<210> SEQ ID NO 87
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 87
gtgacagact cagcattcca                                               20

<210> SEQ ID NO 88
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 88
gtctgatgca ccacttgtgc                                               20

<210> SEQ ID NO 89
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 89
tgccatgtct gagcataggc                                               20

<210> SEQ ID NO 90
<211> LENGTH: 20
<212> TYPE: DNA
<213> ORGANISM: Artificial Sequence
<220> FEATURE:
```

```
<223> OTHER INFORMATION: Antisense Oligonucleotide

<400> SEQUENCE: 90
atactcctgt cctggccacc                                                   20

<210> SEQ ID NO 91
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 91
attgccatag ttcccttgga                                                   20

<210> SEQ ID NO 92
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 92
agtgtcaccc acacagctgc                                                   20

<210> SEQ ID NO 93
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 93
ccaccggttg cccaatgatg                                                   20

<210> SEQ ID NO 94
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 94
gtggacatac atgagcacag                                                   20

<210> SEQ ID NO 95
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 95
tagttgagca cgtagtagtc                                                   20

<210> SEQ ID NO 96
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 96
ctttggcagt agctcatacc                                                   20
```

```
<210> SEQ ID NO 97
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 97
tccagaactc caggcccagg                                               20

<210> SEQ ID NO 98
<211> LENGTH: 20
<212> TYPE: RNA
<213> ORGANISM: H. sapiens
<220> FEATURE:

<400> SEQUENCE: 98
gaauggacga gagaggcggc                                               20

<210> SEQ ID NO 99
<211> LENGTH: 20
<212> TYPE: RNA
<213> ORGANISM: H. sapiens
<220> FEATURE:

<400> SEQUENCE: 99
ccguugucua gggcccggag                                               20

<210> SEQ ID NO 100
<211> LENGTH: 20
<212> TYPE: RNA
<213> ORGANISM: H. sapiens
<220> FEATURE:

<400> SEQUENCE: 100
gcgccucggg cgcuacgaac                                               20

<210> SEQ ID NO 101
<211> LENGTH: 20
<212> TYPE: RNA
<213> ORGANISM: H. sapiens
<220> FEATURE:

<400> SEQUENCE: 101
cacgcuuggc ugcggccggg                                               20

<210> SEQ ID NO 102
<211> LENGTH: 20
<212> TYPE: RNA
<213> ORGANISM: H. sapiens
<220> FEATURE:

<400> SEQUENCE: 102
ugcgggcuga ggccaugggc                                               20

<210> SEQ ID NO 103
<211> LENGTH: 20
<212> TYPE: RNA
<213> ORGANISM: H. sapiens
<220> FEATURE:

<400> SEQUENCE: 103
gggucgcggc ccucgagcca                                               20

<210> SEQ ID NO 104
```

-continued

```
<211> LENGTH: 20
<212> TYPE: RNA
<213> ORGANISM: H. sapiens
<220> FEATURE:

<400> SEQUENCE: 104
cggcggcggc gggccugcgg                                           20

<210> SEQ ID NO 105
<211> LENGTH: 20
<212> TYPE: RNA
<213> ORGANISM: H. sapiens
<220> FEATURE:

<400> SEQUENCE: 105
aaggacggag acgccggcgu                                           20

<210> SEQ ID NO 106
<211> LENGTH: 20
<212> TYPE: RNA
<213> ORGANISM: H. sapiens
<220> FEATURE:

<400> SEQUENCE: 106
gggcagcggc cacugggagc                                           20

<210> SEQ ID NO 107
<211> LENGTH: 20
<212> TYPE: RNA
<213> ORGANISM: H. sapiens
<220> FEATURE:

<400> SEQUENCE: 107
ugaggugcca ucgccugcag                                           20

<210> SEQ ID NO 108
<211> LENGTH: 20
<212> TYPE: RNA
<213> ORGANISM: H. sapiens
<220> FEATURE:

<400> SEQUENCE: 108
agcaacuacc guggcauccu                                           20

<210> SEQ ID NO 109
<211> LENGTH: 20
<212> TYPE: RNA
<213> ORGANISM: H. sapiens
<220> FEATURE:

<400> SEQUENCE: 109
agaaccucau caaguauggc                                           20

<210> SEQ ID NO 110
<211> LENGTH: 20
<212> TYPE: RNA
<213> ORGANISM: H. sapiens
<220> FEATURE:

<400> SEQUENCE: 110
ugguuauugc ggccaauguc                                           20

<210> SEQ ID NO 111
<211> LENGTH: 20
<212> TYPE: RNA
```

<213> ORGANISM: H. sapiens
<220> FEATURE:

<400> SEQUENCE: 111
gacggagcag gcgggacugc                                                    20

<210> SEQ ID NO 112
<211> LENGTH: 20
<212> TYPE: RNA
<213> ORGANISM: H. sapiens
<220> FEATURE:

<400> SEQUENCE: 112
agcggcugug gucuuacugg                                                    20

<210> SEQ ID NO 113
<211> LENGTH: 20
<212> TYPE: RNA
<213> ORGANISM: H. sapiens
<220> FEATURE:

<400> SEQUENCE: 113
uggcgcugau ggcgcacacc                                                    20

<210> SEQ ID NO 114
<211> LENGTH: 20
<212> TYPE: RNA
<213> ORGANISM: H. sapiens
<220> FEATURE:

<400> SEQUENCE: 114
gaagaaggcc agcagugcug                                                    20

<210> SEQ ID NO 115
<211> LENGTH: 20
<212> TYPE: RNA
<213> ORGANISM: H. sapiens
<220> FEATURE:

<400> SEQUENCE: 115
caccuugugc uacgagcuca                                                    20

<210> SEQ ID NO 116
<211> LENGTH: 20
<212> TYPE: RNA
<213> ORGANISM: H. sapiens
<220> FEATURE:

<400> SEQUENCE: 116
gacauggacu acucacgcau                                                    20

<210> SEQ ID NO 117
<211> LENGTH: 20
<212> TYPE: RNA
<213> ORGANISM: H. sapiens
<220> FEATURE:

<400> SEQUENCE: 117
caaucaccuc aucuggcuca                                                    20

<210> SEQ ID NO 118
<211> LENGTH: 20
<212> TYPE: RNA
<213> ORGANISM: H. sapiens
<220> FEATURE:

```
<400> SEQUENCE: 118
ugaaugccgu ggcugagcuc                                           20

<210> SEQ ID NO 119
<211> LENGTH: 20
<212> TYPE: RNA
<213> ORGANISM: H. sapiens
<220> FEATURE:

<400> SEQUENCE: 119
acuacgugcu caacuaugag                                           20

<210> SEQ ID NO 120
<211> LENGTH: 20
<212> TYPE: RNA
<213> ORGANISM: H. sapiens
<220> FEATURE:

<400> SEQUENCE: 120
gagggccugg cuucucacug                                           20

<210> SEQ ID NO 121
<211> LENGTH: 20
<212> TYPE: RNA
<213> ORGANISM: H. sapiens
<220> FEATURE:

<400> SEQUENCE: 121
gccucgagug cuggggaugg                                           20

<210> SEQ ID NO 122
<211> LENGTH: 20
<212> TYPE: RNA
<213> ORGANISM: H. sapiens
<220> FEATURE:

<400> SEQUENCE: 122
gccuggcugc acagcauccu                                           20

<210> SEQ ID NO 123
<211> LENGTH: 20
<212> TYPE: RNA
<213> ORGANISM: H. sapiens
<220> FEATURE:

<400> SEQUENCE: 123
auggggcucu guccugcacc                                           20

<210> SEQ ID NO 124
<211> LENGTH: 20
<212> TYPE: RNA
<213> ORGANISM: H. sapiens
<220> FEATURE:

<400> SEQUENCE: 124
ggcgacagca ggccagacac                                           20

<210> SEQ ID NO 125
<211> LENGTH: 20
<212> TYPE: RNA
<213> ORGANISM: H. sapiens
<220> FEATURE:

<400> SEQUENCE: 125
```
agucugaugc cagcugggag                                               20

<210> SEQ ID NO 126
<211> LENGTH: 20
<212> TYPE: RNA
<213> ORGANISM: M. musculus
<220> FEATURE:

<400> SEQUENCE: 126
gugcgggccg aagccauggg                                               20

<210> SEQ ID NO 127
<211> LENGTH: 20
<212> TYPE: RNA
<213> ORGANISM: M. musculus
<220> FEATURE:

<400> SEQUENCE: 127
cgaggugcga gacgcggcug                                               20

<210> SEQ ID NO 128
<211> LENGTH: 20
<212> TYPE: RNA
<213> ORGANISM: M. musculus
<220> FEATURE:

<400> SEQUENCE: 128
ggggugacgc gccggcuccg                                               20

<210> SEQ ID NO 129
<211> LENGTH: 20
<212> TYPE: RNA
<213> ORGANISM: M. musculus
<220> FEATURE:

<400> SEQUENCE: 129
agacgggcgg accagcgugg                                               20

<210> SEQ ID NO 130
<211> LENGTH: 20
<212> TYPE: RNA
<213> ORGANISM: M. musculus
<220> FEATURE:

<400> SEQUENCE: 130
gcgacggcua cugggaucug                                               20

<210> SEQ ID NO 131
<211> LENGTH: 20
<212> TYPE: RNA
<213> ORGANISM: M. musculus
<220> FEATURE:

<400> SEQUENCE: 131
aggugccauc gucugcaaga                                               20

<210> SEQ ID NO 132
<211> LENGTH: 20
<212> TYPE: RNA
<213> ORGANISM: M. musculus
<220> FEATURE:

<400> SEQUENCE: 132
caauuaucgu gguauccuga                                               20

<210> SEQ ID NO 133
<211> LENGTH: 20
<212> TYPE: RNA
<213> ORGANISM: M. musculus
<220> FEATURE:

<400> SEQUENCE: 133
auuggugugu ggugaugcug                                              20

<210> SEQ ID NO 134
<211> LENGTH: 20
<212> TYPE: RNA
<213> ORGANISM: M. musculus
<220> FEATURE:

<400> SEQUENCE: 134
auccgaguaa augcaagguu                                              20

<210> SEQ ID NO 135
<211> LENGTH: 20
<212> TYPE: RNA
<213> ORGANISM: M. musculus
<220> FEATURE:

<400> SEQUENCE: 135
cagagcagau ggggcugcug                                              20

<210> SEQ ID NO 136
<211> LENGTH: 20
<212> TYPE: RNA
<213> ORGANISM: M. musculus
<220> FEATURE:

<400> SEQUENCE: 136
cuacaugugg uuaaccuggc                                              20

<210> SEQ ID NO 137
<211> LENGTH: 20
<212> TYPE: RNA
<213> ORGANISM: M. musculus
<220> FEATURE:

<400> SEQUENCE: 137
gcucuggcau cauacuccau                                              20

<210> SEQ ID NO 138
<211> LENGTH: 20
<212> TYPE: RNA
<213> ORGANISM: M. musculus
<220> FEATURE:

<400> SEQUENCE: 138
uggugccgcc agcgaagggu                                              20

<210> SEQ ID NO 139
<211> LENGTH: 20
<212> TYPE: RNA
<213> ORGANISM: M. musculus
<220> FEATURE:

<400> SEQUENCE: 139
agcaagcugu gagcuaucca                                              20

```
<210> SEQ ID NO 140
<211> LENGTH: 20
<212> TYPE: RNA
<213> ORGANISM: M. musculus
<220> FEATURE:

<400> SEQUENCE: 140
ugcuacgacg aguucuugag                                                     20

<210> SEQ ID NO 141
<211> LENGTH: 20
<212> TYPE: RNA
<213> ORGANISM: M. musculus
<220> FEATURE:

<400> SEQUENCE: 141
caaggauaug gacuauucac                                                     20

<210> SEQ ID NO 142
<211> LENGTH: 20
<212> TYPE: RNA
<213> ORGANISM: M. musculus
<220> FEATURE:

<400> SEQUENCE: 142
ugucucaaug cuguggcaga                                                     20

<210> SEQ ID NO 143
<211> LENGTH: 20
<212> TYPE: RNA
<213> ORGANISM: M. musculus
<220> FEATURE:

<400> SEQUENCE: 143
gcgaguucua cagagauugg                                                     20

<210> SEQ ID NO 144
<211> LENGTH: 20
<212> TYPE: RNA
<213> ORGANISM: M. musculus
<220> FEATURE:

<400> SEQUENCE: 144
uggaaugcug agucugucac                                                     20

<210> SEQ ID NO 145
<211> LENGTH: 20
<212> TYPE: RNA
<213> ORGANISM: M. musculus
<220> FEATURE:

<400> SEQUENCE: 145
gcacaagugg ugcaucagac                                                     20

<210> SEQ ID NO 146
<211> LENGTH: 20
<212> TYPE: RNA
<213> ORGANISM: M. musculus
<220> FEATURE:

<400> SEQUENCE: 146
gccuaugcuc agacauggca                                                     20

<210> SEQ ID NO 147
<211> LENGTH: 20
```

```
<212> TYPE: RNA
<213> ORGANISM: M. musculus
<220> FEATURE:

<400> SEQUENCE: 147
gguggccagg acaggaguau                                                   20

<210> SEQ ID NO 148
<211> LENGTH: 20
<212> TYPE: RNA
<213> ORGANISM: M. musculus
<220> FEATURE:

<400> SEQUENCE: 148
uccaagggaa cuauggcaau                                                   20

<210> SEQ ID NO 149
<211> LENGTH: 20
<212> TYPE: RNA
<213> ORGANISM: M. musculus
<220> FEATURE:

<400> SEQUENCE: 149
gcagcugugu gggugacacu                                                   20

<210> SEQ ID NO 150
<211> LENGTH: 20
<212> TYPE: RNA
<213> ORGANISM: M. musculus
<220> FEATURE:

<400> SEQUENCE: 150
caucauuggg caaccggugg                                                   20

<210> SEQ ID NO 151
<211> LENGTH: 20
<212> TYPE: RNA
<213> ORGANISM: M. musculus
<220> FEATURE:

<400> SEQUENCE: 151
cugugcucau guauguccac                                                   20

<210> SEQ ID NO 152
<211> LENGTH: 20
<212> TYPE: RNA
<213> ORGANISM: M. musculus
<220> FEATURE:

<400> SEQUENCE: 152
ccugggccug gaguucugga                                                   20

<210> SEQ ID NO 153
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 153
ccttccctga aggttcctcc                                                   20

<210> SEQ ID NO 154
<211> LENGTH: 1751
<212> TYPE: DNA
```

<213> ORGANISM: R. norvegicus
<220> FEATURE:
<221> NAME/KEY: CDS
<222> LOCATION: (36)...(1532)

<400> SEQUENCE: 154

```
gaagattggg ccgcgacgag gtgcgggccg aagcc atg ggc gac cgc gga ggc         53
                                      Met Gly Asp Arg Gly Gly
                                        1               5 gcg gga agc tct cgg cgt cgc agg acc ggc tcg cgg gtt tcc gtc cag        101
Ala Gly Ser Ser Arg Arg Arg Thr Gly Ser Arg Val Ser Val Gln
             10                  15                  20 gga ggt agt ggg ccc aag gta gaa gag gac gag gtg cga gaa gcg gct        149
Gly Gly Ser Gly Pro Lys Val Glu Glu Asp Glu Val Arg Glu Ala Ala
         25                  30                  35 gtg agc ccc gac ttg ggc gcc ggg ggt gac gcg ccg gct ccg gct ccg        197
Val Ser Pro Asp Leu Gly Ala Gly Gly Asp Ala Pro Ala Pro Ala Pro
 40                  45                  50 gct cca gcc cat acc cgg gac aaa gac cgg cag acc agc gtg ggc gac        245
Ala Pro Ala His Thr Arg Asp Lys Asp Arg Gln Thr Ser Val Gly Asp
 55                  60                  65                  70 ggc cac tgg gag ctg agg tgc cat cgt ctg caa gac tct ttg ttc agc        293
Gly His Trp Glu Leu Arg Cys His Arg Leu Gln Asp Ser Leu Phe Ser
                 75                  80                  85 tca gac agc ggt ttc agc aat tac cgt ggt atc ctg aat tgg tgc gtg        341
Ser Asp Ser Gly Phe Ser Asn Tyr Arg Gly Ile Leu Asn Trp Cys Val
             90                  95                 100 gtg atg ctg atc ctg agt aat gca agg tta tct tta gag aat ctt atc        389
Val Met Leu Ile Leu Ser Asn Ala Arg Leu Ser Leu Glu Asn Leu Ile
        105                 110                 115 aag tat ggc atc ctg gtg gat ccc atc cag gtg gtg tct ctg ttt ctg        437
Lys Tyr Gly Ile Leu Val Asp Pro Ile Gln Val Val Ser Leu Phe Leu
    120                 125                 130 aag gac ccc tac agc tgg cct gcc cca tgc ttg atc att gca tcc aat        485
Lys Asp Pro Tyr Ser Trp Pro Ala Pro Cys Leu Ile Ile Ala Ser Asn
135                 140                 145                 150 atc ttt att gtg gct aca ttt cag att gag aag cgc ctg tca gtg ggt        533
Ile Phe Ile Val Ala Thr Phe Gln Ile Glu Lys Arg Leu Ser Val Gly
                155                 160                 165 gcc ctg aca gag cag atg ggg ctg cta cat gtg gtt aac ctg gcc            581
Ala Leu Thr Glu Gln Met Gly Leu Leu Leu His Val Val Asn Leu Ala
            170                 175                 180 aca att atc tgc ttc cca gca gct gtg gcc tta ctg gtt gag tct atc        629
Thr Ile Ile Cys Phe Pro Ala Ala Val Ala Leu Leu Val Glu Ser Ile
        185                 190                 195 act cca gtg ggt tcc ctg ttt gct ctg gca tca tac tcc atc atc ttc        677
Thr Pro Val Gly Ser Leu Phe Ala Leu Ala Ser Tyr Ser Ile Ile Phe
    200                 205                 210 ctc aag ctt tct tcc tac cgg gat gtc aat ctg tgg tgc cgc cag cga        725
Leu Lys Leu Ser Ser Tyr Arg Asp Val Asn Leu Trp Cys Arg Gln Arg
215                 220                 225                 230 agg gtc aag gcc aaa gct gtg tct gca ggg aag aag gtc agt ggg gct        773
Arg Val Lys Ala Lys Ala Val Ser Ala Gly Lys Lys Val Ser Gly Ala
                235                 240                 245 gct gcc cag aac act gta agc tat ccg gac aac ctg acc tac cga gat        821
Ala Ala Gln Asn Thr Val Ser Tyr Pro Asp Asn Leu Thr Tyr Arg Asp
            250                 255                 260 ctc tat tac ttc atc ttt gct cct act ttg tgt tat gaa ctc aac ttt        869
Leu Tyr Tyr Phe Ile Phe Ala Pro Thr Leu Cys Tyr Glu Leu Asn Phe
        265                 270                 275
```

```
cct cga tcc ccc cga ata cga aag cgc ttt ctg cta cgg cgg gtt ctt      917
Pro Arg Ser Pro Arg Ile Arg Lys Arg Phe Leu Leu Arg Arg Val Leu
    280                 285                 290 gag atg ctc ttt ttc acc cag ctt caa gtg ggg ctg atc cag cag tgg      965
Glu Met Leu Phe Phe Thr Gln Leu Gln Val Gly Leu Ile Gln Gln Trp
295                 300                 305                 310 atg gtc cct act atc cag aac tcc atg aag ccc ttc aag gac atg gac     1013
Met Val Pro Thr Ile Gln Asn Ser Met Lys Pro Phe Lys Asp Met Asp
                315                 320                 325 tat tca cga atc att gag cgt ctc tta aag ctg gcg gtc ccc aac cat     1061
Tyr Ser Arg Ile Ile Glu Arg Leu Leu Lys Leu Ala Val Pro Asn His
            330                 335                 340 ctg ata tgg ctc atc ttc ttc tat tgg ctt ttc cac tca tgt ctc aat     1109
Leu Ile Trp Leu Ile Phe Phe Tyr Trp Leu Phe His Ser Cys Leu Asn
        345                 350                 355 gct gtg gca gag ctc ctg cag ttt gga gac cgc gag ttc tac agg gac     1157
Ala Val Ala Glu Leu Leu Gln Phe Gly Asp Arg Glu Phe Tyr Arg Asp
    360                 365                 370 tgg tgg aat gct gag tct gtc acc tac ttt tgg cag aac tgg aat atc     1205
Trp Trp Asn Ala Glu Ser Val Thr Tyr Phe Trp Gln Asn Trp Asn Ile
375                 380                 385                 390 ccc gtg cac aag tgg tgc atc aga cac ttt tac aag cct atg ctc aga     1253
Pro Val His Lys Trp Cys Ile Arg His Phe Tyr Lys Pro Met Leu Arg
                395                 400                 405 ctg ggc agc aac aaa tgg atg gcc agg act ggg gtc ttt tgg gcg tca     1301
Leu Gly Ser Asn Lys Trp Met Ala Arg Thr Gly Val Phe Trp Ala Ser
            410                 415                 420 gct ttc ttt cat gag tac cta gtg agc att ccc ctg agg atg ttc cgc     1349
Ala Phe Phe His Glu Tyr Leu Val Ser Ile Pro Leu Arg Met Phe Arg
        425                 430                 435 ctt tgg gca ttc aca gca atg atg gct cag gtc cca ctg gcc tgg att     1397
Leu Trp Ala Phe Thr Ala Met Met Ala Gln Val Pro Leu Ala Trp Ile
    440                 445                 450 gtg aac cgc ttc ttc caa ggg aac tat ggc aat gca gct gtg tgg gtg     1445
Val Asn Arg Phe Phe Gln Gly Asn Tyr Gly Asn Ala Ala Val Trp Val
455                 460                 465                 470 aca ctc atc att ggg caa ccg gtg gct gtg ctc atg tat gtc cac gac     1493
Thr Leu Ile Ile Gly Gln Pro Val Ala Val Leu Met Tyr Val His Asp
                475                 480                 485 tac tac gtg ctc aac tat gat gcc cca gtg ggg gca tga gctactgcca     1542
Tyr Tyr Val Leu Asn Tyr Asp Ala Pro Val Gly Ala *
            490                 495 aaggccagcc tccctaacct gggcctggag ttctggaggg cttcctgctg ctgcacactc   1602
ccctagtttg gaggcctttc tgccctatg gggcctactc ctgctcttgg ggatggccct    1662
gagccagctg gttgagccag tgctgggagt ttgtgctgac caggggctta ggatatcaat   1722
aaagagctat ctaaaaaaaa aaaaaaaa                                      1751

<210> SEQ ID NO 155
<211> LENGTH: 16
<212> TYPE: DNA
<213> ORGANISM: Artificial Sequence
<220> FEATURE:
<223> OTHER INFORMATION: PCR Primer

<400> SEQUENCE: 155
cagaccagcg tgggcg                                                     16

<210> SEQ ID NO 156
<211> LENGTH: 24
```

```
<212> TYPE: DNA
<213> ORGANISM: Artificial Sequence
<220> FEATURE:
<223> OTHER INFORMATION: PCR Primer

<400> SEQUENCE: 156
gaacaaagag tcttgcagac gatg                                    24

<210> SEQ ID NO 157
<211> LENGTH: 21
<212> TYPE: DNA
<213> ORGANISM: Artificial Sequence
<220> FEATURE:
<223> OTHER INFORMATION: PCR Probe

<400> SEQUENCE: 157
cggccactgg gagctgaggt g                                       21

<210> SEQ ID NO 158
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 158
tcgcccatgg cttcggcccg                                         20

<210> SEQ ID NO 159
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 159
agcttcccgc gcctccgcgg                                         20

<210> SEQ ID NO 160
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 160
ggtcctgcga cgccgagagc                                         20

<210> SEQ ID NO 161
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 161
ctggacggaa acccgcgagc                                         20

<210> SEQ ID NO 162
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 162
```

-continued taccttgggc ccactacctc 20

<210> SEQ ID NO 163
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 163
tcgcacctcg tcctcttcta 20

<210> SEQ ID NO 164
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 164
gagccggcgc gtcaccccg 20

<210> SEQ ID NO 165
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 165
tatgggctgg agccggagcc 20

<210> SEQ ID NO 166
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 166
ccgggtatgg gctggagccg 20

<210> SEQ ID NO 167
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 167
tcgcccacgc tggtctgccg 20

<210> SEQ ID NO 168
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 168
ggcacctcag ctcccagtgg 20

<210> SEQ ID NO 169
<211> LENGTH: 20
<212> TYPE: DNA
<213> ORGANISM: Artificial Sequence -continued

```
<220> FEATURE:
<223> OTHER INFORMATION: Antisense Oligonucleotide

<400> SEQUENCE: 169
ctgtctgagc tgaacaaaga                                               20

<210> SEQ ID NO 170
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 170
aggataccac ggtaattgct                                               20

<210> SEQ ID NO 171
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 171
caccaattca ggataccacg                                               20

<210> SEQ ID NO 172
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 172
gcattactca ggatcagcat                                               20

<210> SEQ ID NO 173
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 173
ctaaagataa ccttgcatta                                               20

<210> SEQ ID NO 174
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 174
acttgataag attctctaaa                                               20

<210> SEQ ID NO 175
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 175
ccaccaggat gccatacttg                                               20
```

<210> SEQ ID NO 176
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 176
ggatccacca ggatgccata                                               20

<210> SEQ ID NO 177
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 177
aaacagagac accacctgga                                               20

<210> SEQ ID NO 178
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 178
ggatgcaatg atcaagcatg                                               20

<210> SEQ ID NO 179
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 179
acaataaaga tattggatgc                                               20

<210> SEQ ID NO 180
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 180
cttctcaatc tgaaatgtag                                               20

<210> SEQ ID NO 181
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 181
aggcgcttct caatctgaaa                                               20

<210> SEQ ID NO 182
<211> LENGTH: 20
<212> TYPE: DNA
<213> ORGANISM: Artificial Sequence
<220> FEATURE:
<223> OTHER INFORMATION: Antisense Oligonucleotide

```
<400> SEQUENCE: 182
gctctgtcag ggcacccact                                              20

<210> SEQ ID NO 183
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 183
agccccatct gctctgtcag                                              20

<210> SEQ ID NO 184
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 184
accacatgta gcagcagccc                                              20

<210> SEQ ID NO 185
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 185
gggaagcaga taattgtggc                                              20

<210> SEQ ID NO 186
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 186
aaggccacag ctgctgggaa                                              20

<210> SEQ ID NO 187
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 187
agactcaacc agtaaggcca                                              20

<210> SEQ ID NO 188
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 188
tggagtgata gactcaacca                                              20

<210> SEQ ID NO 189
```

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 189
ggagtatgat gccagagcaa                                                    20

<210> SEQ ID NO 190
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 190
gaggaagatg atggagtatg                                                    20

<210> SEQ ID NO 191
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 191
ccggtaggaa gaaagcttga                                                    20

<210> SEQ ID NO 192
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 192
ccttcgctgg cggcaccaca                                                    20

<210> SEQ ID NO 193
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 193
acagctttgg ccttgaccct                                                    20

<210> SEQ ID NO 194
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 194
accttcttcc ctgcagacac                                                    20

<210> SEQ ID NO 195
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 195
```

```
cagcagcccc actgaccttc                                              20

<210> SEQ ID NO 196
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 196
gatagcttac agtgttctgg                                              20

<210> SEQ ID NO 197
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 197
ggtaggtcag gttgtccgga                                              20

<210> SEQ ID NO 198
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 198
agagatctcg gtaggtcagg                                              20

<210> SEQ ID NO 199
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 199
aagatgaagt aatagagatc                                              20

<210> SEQ ID NO 200
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 200
acaaagtagg agcaaagatg                                              20

<210> SEQ ID NO 201
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 201
aagttgagtt cataacacaa                                              20

<210> SEQ ID NO 202
<211> LENGTH: 20
<212> TYPE: DNA
```

```
<213> ORGANISM: Artificial Sequence
<220> FEATURE:
<223> OTHER INFORMATION: Antisense Oligonucleotide

<400> SEQUENCE: 202
aaaaagagca tctcaagaac                                              20

<210> SEQ ID NO 203
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 203
cagccccact tgaagctggg                                              20

<210> SEQ ID NO 204
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 204
catccactgc tggatcagcc                                              20

<210> SEQ ID NO 205
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 205
ggagttctgg atagtaggga                                              20

<210> SEQ ID NO 206
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 206
aagggcttca tggagttctg                                              20

<210> SEQ ID NO 207
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 207
catgtccttg aagggcttca                                              20

<210> SEQ ID NO 208
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 208
cgccagcttt aagagacgct                                              20
```

<210> SEQ ID NO 209
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 209
gctctgccac agcattgaga                                            20

<210> SEQ ID NO 210
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 210
tagaactcgc ggtctccaaa                                            20

<210> SEQ ID NO 211
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 211
ggtgacagac tcagcattcc                                            20

<210> SEQ ID NO 212
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 212
gatattccag ttctgccaaa                                            20

<210> SEQ ID NO 213
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 213
tgtctgatgc accacttgtg                                            20

<210> SEQ ID NO 214
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 214
agaccccagt cctggccatc                                            20

<210> SEQ ID NO 215
<211> LENGTH: 20
<212> TYPE: DNA
<213> ORGANISM: Artificial Sequence
<220> FEATURE:

```
<223> OTHER INFORMATION: Antisense Oligonucleotide

<400> SEQUENCE: 215
tactcatgaa agaaagctga                                                    20

<210> SEQ ID NO 216
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 216
cattgctgtg aatgcccaaa                                                    20

<210> SEQ ID NO 217
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 217
acaatccagg ccagtgggac                                                    20

<210> SEQ ID NO 218
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 218
tgcattgcca tagttccctt                                                    20

<210> SEQ ID NO 219
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 219
gcccaatgat gagtgtcacc                                                    20

<210> SEQ ID NO 220
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 220
gtagtcgtgg acatacatga                                                    20

<210> SEQ ID NO 221
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 221
ttggcagtag ctcatgcccc                                                    20
```

```
<210> SEQ ID NO 222
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 222
ctggcctttg gcagtagctc                                               20

<210> SEQ ID NO 223
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 223
cctccagaac tccaggccca                                               20

<210> SEQ ID NO 224
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 224
atccccaaga gcaggagtag                                               20

<210> SEQ ID NO 225
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 225
cccagcactg gctcaaccag                                               20

<210> SEQ ID NO 226
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 226
ttgatatcct aagcccctgg                                               20

<210> SEQ ID NO 227
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 227
tttttttttt ttagatagct                                               20

<210> SEQ ID NO 228
<211> LENGTH: 19
<212> TYPE: DNA
<213> ORGANISM: Artificial Sequence
<220> FEATURE:
<223> OTHER INFORMATION: antisense Oligonucleotide
```

-continued

```
<400> SEQUENCE: 228
cgagaggcgg acgggaccg                                            19

<210> SEQ ID NO 229
<211> LENGTH: 21
<212> TYPE: DNA
<213> ORGANISM: Artificial Sequence
<220> FEATURE:
<223> OTHER INFORMATION: antisense Oligonucleotide

<400> SEQUENCE: 229
cgagaggcgg acgggaccgt t                                         21

<210> SEQ ID NO 230
<211> LENGTH: 21
<212> TYPE: DNA
<213> ORGANISM: Artificial Sequence
<220> FEATURE:
<223> OTHER INFORMATION: complement Oligonucleotide

<400> SEQUENCE: 230
ttgctctccg cctgccctgg c                                         21

<210> SEQ ID NO 231
<211> LENGTH: 19
<212> TYPE: DNA
<213> ORGANISM: Artificial Sequence
<220> FEATURE:
<223> OTHER INFORMATION: complement Oligonucleotide

<400> SEQUENCE: 231
gctctccgcc tgccctggc                                            19
```

MODULATION OF DIACYLGLYCEROL ACYLTRANSFERASE 1 EXPRESSION

CROSS-REFERENCE TO RELATED APPLICATION

This application is a continuation-in-part application of U.S. non-provisional patent application No. 10/394,808 filed Mar. 21, 2003.

BACKGROUND OF THE INVENTION

Triglycerides are one of the major energy storage molecules in eukaryotes. The absorption of triglycerides (also called triacylglycerols) from food is a very efficient process that occurs by a series of steps wherein the dietary triacylglycerols are hydrolyzed in the intestinal lumen and then resynthesized within enterocytes. The resynthesis of triacylglycerols can occur via the monoacylglycerol pathway, which commences with monoacylglycerol acyltransferase (MGAT) catalyzing the synthesis of diacylglycerol from monoacylglycerol and fatty acyl-CoA. An alternative synthesis of diacylglycerols is provided by the glycerol-phosphate pathway, which describes the coupling of two molecules of fatty acyl-CoA to glycerol-3-phosphate. In either case, diacylglycerol is then acylated with another molecule of fatty acyl-CoA in a reaction catalyzed by one of two diacylglycerol acyltransferase enzymes to form the triglyceride (Farese et al., *Curr. Opin. Lipidol.*, 2000, 11, 229-234).

The reaction catalyzed by diacylglycerol acyltransferase 1 is the final and only committed step in triglyceride synthesis. As such, diacylglycerol acyltransferase 1 is involved in intestinal fat absorption, lipoprotein assembly, regulating plasma triglyceride concentrations, and fat storage in adipocytes. Although identified in 1960, the genes encoding human and mouse diacylglycerol acyltransferase 1 (also called DGAT1, acyl CoA:diacylglycerol acyltransferase, acyl CoA:cholesterol acyltransferase-related enzyme, ACAT related gene product, and ARGP1) were not cloned until 1998 (Cases et al., *Proc. Natl. Acad. Sci. U. S. A.*, 1998, 95, 13018-13023; Oelkers et al., *J. Biol. Chem.*, 1998, 273, 26765-26771). U.S. Pat. No. 6,100,077 refers to an isolated nucleic acid encoding a human diacylglycerol acyltransferase 1. Diacylglycerol acyltransferase 1 is a microsomal membrane bound enzyme and has 39% nucleotide identity to the related acyl CoA:cholesterol acyltransferase (Oelkers et al., *J. Biol. Chem.*, 1998, 273, 26765-26771). A splice variant of diacylglycerol acyltransferase 1 has also been cloned that contains a 77 nucleotide insert of unspliced intron with an in-frame stop codon, resulting in a truncated form of diacylglycerol acyltransferase 1 that terminates at Arg-387 deleting 101 residues from the C-terminus containing the putative active site (Cheng et al., *Biochem. J.*, 2001, 359, 707-714).

Dysregulation of diacylglycerol acyltransferase 1 may play a role in the development of obesity. Upon differentiation of mouse 3T3-L1 cells into mature adipocytes, a 90 fold increase in diacylglycerol acyltransferase 1 levels is observed. However, forced overexpression of diacylglycerol acyltransferase 1 in mature adipocytes results in only a 2 fold increase in diacylglycerol acyltransferase 1 levels. This leads to an increase in cellular triglyceride synthesis without a concomitant increase in triglyceride lipolysis, leading to the suggestion that manipulation of the steady state level of diacylglycerol acyltransferase 1 may offer a potential means to treat obesity (Yu et al., *J. Biol. Chem.*, 2002, 277, 50876-50884).

Alterations in diacylglycerol acyltransferase 1 expression may affect human body weight. In a random Turkish population, five polymorphisms in the human diacylglycerol acyltransferase 1 promoter and 5' non-coding sequence have been identified. One common variant, C79T, revealed reduced promoter activity for the 79T allele and is associated with a lower body mass index, higher plasma cholesterol HDL levels, and lower diastolic blood pressure in Turkish women (Ludwig et al., *Clin. Genet.*, 2002, 62, 68-73).

Diacylglycerol acyltransferase 1 knockout mice exhibit interesting phenotypes which indicate that inhibition of diacylglycerol acyltransferase 1 may offer a strategy for treating obesity and obesity-associated insulin resistance. Mice lacking diacylglycerol acyltransferase 1 are viable and can still synthesize triglycerides through other biological routes. However the mice are lean and resistant to diet-induce obesity (Smith et al., *Nat. Genet.*, 2000, 25, 87-90), have decreased levels of tissue triglycerides, and increased sensitivity to insulin and leptin (Chen et al., *J. Clin. Invest.*, 2002, 109, 1049-1055).

Currently, there are no known therapeutic agents which effectively inhibit the synthesis of diacylglycerol acyltransferase 1 and to date, investigative strategies aimed at modulating diacylglycerol acyltransferase 1 function have involved naturally-occurring small molecule derivatives of roselipins and xanthohumols isolated from *Gliocladium roseum* and *Humulus lupulus*, respectively (Tabata et al., *Phytochemistry*, 1997, 46, 683-687; Tomoda et al., *J. Antibiot.* (Tokyo)., 1999, 52, 689-694).

Consequently, there remains a long felt need for additional agents capable of effectively inhibiting diacylglycerol acyltransferase 1 function.

SUMMARY OF THE INVENTION

The present invention provides compositions and methods for modulating the expression of diacylglycerol acyltransferase 1. In particular, this invention relates to compounds, particularly oligonucleotide compounds, which, in preferred embodiments, hybridize with nucleic acid molecules encoding diacylglycerol acyltransferase 1. Such compounds are shown herein to modulate the expression of diacylglycerol acyltransferase 1.

The present invention is directed to compounds, especially nucleic acid and nucleic acid-like oligomers, which are targeted to a nucleic acid encoding diacylglycerol acyltransferase 1, and which modulate the expression of diacylglycerol acyltransferase 1. Pharmaceutical and other compositions comprising the compounds of the invention are also provided.

Antisense technology is emerging as an effective means for reducing the expression of specific gene products and is uniquely useful in a number of therapeutic, diagnostic, and research applications for the modulation of diacylglycerol acyltransferase 1 expression.

Further provided are methods of screening for modulators of diacylglycerol acyltransferase 1 and methods of modulating the expression of diacylglycerol acyltransferase 1 in cells, tissues or animals comprising contacting said cells, tissues or animals with one or more of the compounds or compositions of the invention. In these methods, the cells or tissues may be contacted in vivo. Alternatively, the cells or tissues may be contacted ex vivo.

Methods of treating an animal, particularly a human, suspected of having or being prone to a disease or condition associated with expression of diacylglycerol acyltransferase 1 are also set forth herein. Such methods comprise administering a therapeutically or prophylactically effective amount of one or more of the compounds or compositions of the invention to the person in need of treatment.

Also provided is a method of making a compound of the invention comprising specifically hybridizing in vitro a first nucleobase strand comprising a sequence of at least 8 contiguous nucleobases of the sequence set forth in SEQ ID NO: 4 to a second nucleobase strand comprising a sequence sufficiently complementary to said first strand so as to permit stable hybridization.

The invention further provides a compound of the invention for use in therapy.

The invention further provides use of a compound or composition of the invention in the manufacture of a medicament for the treatment of any and all conditions disclosed herein.

DETAILED DESCRIPTION OF THE INVENTION

A. Overview of the Invention

The present invention employs compounds, preferably oligonucleotides and similar species for use in modulating the function or effect of nucleic acid molecules encoding diacylglycerol acyltransferase 1. This is accomplished by providing oligonucleotides that specifically hybridize with one or more nucleic acid molecules encoding diacylglycerol acyltransferase 1. As used herein, the terms "target nucleic acid" and "nucleic acid molecule encoding diacylglycerol acyltransferase 1" have been used for convenience to encompass DNA encoding diacylglycerol acyltransferase 1, RNA (including pre-mRNA and mRNA or portions thereof) transcribed from such DNA, and also cDNA derived from such RNA. The hybridization of a compound of this invention with its target nucleic acid is generally referred to as "antisense". Consequently, the preferred mechanism believed to be included in the practice of some preferred embodiments of the invention is referred to herein as "antisense inhibition." Such antisense inhibition is typically based upon hydrogen bonding-based hybridization of oligonucleotide strands or segments such that at least one strand or segment is cleaved, degraded, or otherwise rendered inoperable. In this regard, it is presently preferred to target specific nucleic acid molecules and their functions for such antisense inhibition.

The functions of DNA to be interfered with can include replication and transcription. Replication and transcription, for example, can be from an endogenous cellular template, a vector, a plasmid construct or otherwise. The functions of RNA to be interfered with can include functions such as translocation of the RNA to a site of protein translation, translocation of the RNA to sites within the cell which are distant from the site of RNA synthesis, translation of protein from the RNA, splicing of the RNA to yield one or more RNA species, and catalytic activity or complex formation involving the RNA which may be engaged in or facilitated by the RNA. One preferred result of such interference with target nucleic acid function is modulation of the expression of diacylglycerol acyltransferase 1. In the context of the present invention, "modulation" and "modulation of expression" mean either an increase (stimulation) or a decrease (inhibition) in the amount or levels of a nucleic acid molecule encoding the gene, e.g., DNA or RNA. Inhibition is often the preferred form of modulation of expression and mRNA is often a preferred target nucleic acid.

In the context of this invention, "hybridization" means the pairing of complementary strands of oligomeric compounds. In the present invention, the preferred mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases that pair through the formation of hydrogen bonds. Hybridization can occur under varying circumstances.

An antisense compound is specifically hybridizable when binding of the compound to the target nucleic acid interferes with the normal function of the target nucleic acid to cause a loss of activity, and there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

In the present invention the phrase "stringent hybridization conditions" or "stringent conditions" refers to conditions under which a compound of the invention will hybridize to its target sequence, but to a minimal number of other sequences. Stringent conditions are sequence-dependent and will be different in different circumstances and in the context of this invention, "stringent conditions" under which oligomeric compounds hybridize to a target sequence are determined by the nature and composition of the oligomeric compounds and the assays in which they are being investigated.

"Complementary," as used herein, refers to the capacity for precise pairing between two nucleobases of an oligomeric compound. For example, if a nucleobase at a certain position of an oligonucleotide (an oligomeric compound), is capable of hydrogen bonding with a nucleobase at a certain position of a target nucleic acid, said target nucleic acid being a DNA, RNA, or oligonucleotide molecule, then the position of hydrogen bonding between the oligonucleotide and the target nucleic acid is considered to be a complementary position. The oligonucleotide and the further DNA, RNA, or oligonucleotide molecule are complementary to each other when a sufficient number of complementary positions in each molecule are occupied by nucleobases that can hydrogen bond with each other. Thus, "specifically hybridizable" and "complementary" are terms that are used to indicate a sufficient degree of precise pairing or complementarity over a sufficient number of nucleobases such that stable and specific binding occurs between the oligonucleotide and a target nucleic acid.

It is understood in the art that the sequence of an antisense compound can be, but need not be, 100% complementary to that of its target nucleic acid to be specifically hybridizable. Moreover, an oligonucleotide may hybridize over one or more segments such that intervening or adjacent segments are not involved in the hybridization event (e.g., a loop structure or hairpin structure). Preferably, the antisense compounds comprise at least 8 contiguous nucleobases of an antisense sequence disclosed herein. It is preferred that the antisense compounds of the present invention comprise at least 70%, or at least 75%, or at least 80%, or at least 85% sequence complementarity to a target region within the target nucleic acid. In another embodiment, the antisense compounds of the present invention comprise 90% sequence complementarity and even more preferably comprise 95% or at least 99% sequence complementarity to the target region within the target nucleic acid sequence to which they are targeted. For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., *J. Mol. Biol.*, 1990, 215, 403-410; Zhang and Madden, *Genome Res.*, 1997, 7, 649-656).

Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (*Adv. Appl. Math.*, 1981, 2, 482-489). In some preferred embodiments, homology, sequence identity or complementarity, between the oligomeric and target is between about 50% to about 60%. In some embodiments, homology, sequence identity or complementarity, is between about 60% to about 70%. In preferred embodiments, homology, sequence identity or complementarity, is between about 70% and about 80%. In more preferred embodiments, homology, sequence identity or complementarity, is between about 80% and about 90%. In some preferred embodiments, homology, sequence identity or complementarity, is about 90%, about 92%, about 94%, about 95%, about 96%, about 97%, about 98%, or about 99%.

B. Compounds of the Invention

According to the present invention, compounds include antisense oligomeric compounds, antisense oligonucleotides, ribozymes, external guide sequence (EGS) oligonucleotides, alternate splicers, primers, probes, and other oligomeric compounds that hybridize to at least a portion of the target nucleic acid. As such, these compounds may be introduced in the form of single-stranded, double-stranded, circular or hairpin oligomeric compounds and may contain structural elements such as internal or terminal bulges or loops. Once introduced to a system, the compounds of the invention may elicit the action of one or more enzymes or structural proteins to effect modification of the target nucleic acid. One non-limiting example of such an enzyme is RNAse H, a cellular endonuclease which cleaves the RNA strand of an RNA:DNA duplex. It is known in the art that single-stranded antisense compounds which are "DNA-like" elicit RNAse H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase III and ribonuclease L family of enzymes.

While the preferred form of antisense compound is a single-stranded antisense oligonucleotide, in many species the introduction of double-stranded structures, such as double-stranded RNA (dsRNA) molecules, induces potent and specific antisense-mediated reduction of the function of a gene or its associated gene products. This phenomenon occurs in both plants and animals and is believed to have an evolutionary connection to viral defense and transposon silencing.

The first evidence that dsRNA could lead to gene silencing in animals came in 1995 from work in the nematode, *Caenorhabditis elegans* (Guo and Kempheus, *Cell*, 1995, 81, 611-620). The primary interference effects of dsRNA are posttranscriptional (Montgomery et al., *Proc. Natl. Acad. Sci. USA*, 1998, 95, 15502-15507). The posttranscriptional antisense mechanism defined in *Caenorhabditis elegans* resulting from exposure to double-stranded RNA (dsRNA) has since been designated RNA interference (RNAi). This term has been generalized to mean antisense-mediated gene silencing involving the introduction of dsRNA leading to the sequence-specific reduction of endogenous targeted mRNA levels (Fire et al., *Nature*, 1998, 391, 806-811). Recently, the single-stranded RNA oligomers of antisense polarity of the dsRNAs have been reported to be the potent inducers of RNAi (Tijsterman et al., *Science*, 2002, 295, 694-697).

In the context of this invention, the term "oligomeric compound" refers to a polymer or oligomer comprising a plurality of monomeric units. In the context of this invention, the term "oligonucleotide" refers to an oligomer or polymer of ribonucleic acid (RNA) or deoxyribonucleic acid (DNA) or mimetics, chimeras, analogs and homologs thereof. This term includes oligonucleotides composed of naturally occurring nucleobases, sugars and covalent internucleoside (backbone) linkages as well as oligonucleotides having non-naturally occurring portions which function similarly. Such modified or substituted oligonucleotides are often preferred over native forms because of desirable properties such as, for example, enhanced cellular uptake, enhanced affinity for a target nucleic acid and increased stability in the presence of nucleases.

The oligonucleotides of the present invention also include modified oligonucleotides in which a different base is present at one or more of the nucleotide positions in the oligonucleotide. For example, if the first nucleotide is an adenosine, modified oligonucleotides may be produced which contain thymidine, guanosine or cytidine at this position. This may be done at any of the positions of the oligonucleotide. These oligonucleotides are then tested using the methods described herein to determine their ability to inhibit expression of diacylglycerol acyltransferase 1 mRNA.

While oligonucleotides are a preferred form of the compounds of this invention, the present invention comprehends other families of compounds as well, including but not limited to oligonucleotide analogs and mimetics such as those described herein.

The compounds in accordance with this invention preferably comprise from about 8 to about 80 nucleobases (i.e. from about 8 to about 80 linked nucleosides). One of ordinary skill in the art will appreciate that the invention embodies compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases in length.

In one preferred embodiment, the compounds of the invention are 12 to 50 nucleobases in length. One having ordinary skill in the art will appreciate that this embodies compounds of 12, 13, 14, 15, 16, 17, 18, 19, 20, 21, 22, 23, 24, 25, 26, 27, 28, 29, 30, 31, 32, 33, 34, 35, 36., 37, 38, 39, 40, 41, 42, 43, 44, 45, 46, 47, 48, 49, or 50 nucleobases in length.

In another preferred embodiment, the compounds of the invention are 15 to 30 nucleobases in length. One having ordinary skill in the art will appreciate that this embodies compounds of 15, 16, 17, 18, 19, 20, 21, 22, 23, 24, 25, 26, 27, 28, 29, or 30 nucleobases in length.

Particularly preferred compounds are oligonucleotides from about 12 to about 50 nucleobases, even more preferably those comprising from about 15 to about 30 nucleobases.

Antisense compounds 8-80 nucleobases in length comprising a stretch of at least eight (8) consecutive nucleobases selected from within the illustrative antisense compounds are considered to be suitable antisense compounds as well.

Exemplary preferred antisense compounds include oligonucleotide sequences that comprise at least the 8 consecutive nucleobases from the 5'-terminus of one of the illustrative preferred antisense compounds (the remaining nucleobases being a consecutive stretch of the same oligonucleotide beginning immediately upstream of the 5'-terminus of the antisense compound which is specifically hybridizable to the target nucleic acid and continuing until the oligonucleotide contains about 8 to about 80 nucleobases). Similarly preferred antisense compounds are represented by oligonucleotide sequences that comprise at least the 8 consecutive nucleobases from the 3'-terminus of one of the illustrative preferred antisense compounds (the remaining nucleobases being a consecutive stretch of the same oligonucleotide beginning immediately downstream of the 3'-terminus of the antisense compound which is specifically hybridizable to the target nucleic acid and continuing until the oligonucleotide contains about 8 to about 80 nucleobases). Exemplary compounds of this invention may be found identified in the Examples and listed in Tables 1, 2, 4, 10, and 11. One having skill in the art armed with the preferred antisense compounds illustrated herein will be able, without undue experimentation, to identify further preferred antisense compounds.

C. Targets of the Invention

"Targeting" an antisense compound to a particular nucleic acid molecule, in the context of this invention, can be a multistep process. The process usually begins with the identification of a target nucleic acid whose function is to be modulated. This target nucleic acid may be, for example, a cellular gene (or mRNA transcribed from the gene) whose expression is associated with a particular disorder or disease state, or a nucleic acid molecule from an infectious agent. In the present invention, the target nucleic acid encodes diacylglycerol acyltransferase 1.

The targeting process usually also includes determination of at least one target region, segment, or site within the target nucleic acid for the antisense interaction to occur such that the desired effect, e.g., modulation of expression, will result. Within the context of the present invention, the term "region" is defined as a portion of the target nucleic acid having at least one identifiable structure, function, or characteristic. Within regions of target nucleic acids are segments. "Segments" are defined as smaller or sub-portions of regions within a target nucleic acid. "Sites," as used in the present invention, are defined as positions within a target nucleic acid.

Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes, having translation initiation codons with the RNA sequence 5'-GUG, 5'-UUG or 5'-CUG, and 5'-AUA, 5'-ACG and 5'-CUG, have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA transcribed from a gene encoding diacylglycerol acyltransferase 1, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Consequently, the "start codon region" (or "translation initiation codon region") and the "stop codon region" (or "translation termination codon region") are all regions that may be targeted effectively with the antisense compounds of the present invention.

The open reading frame (QRF) or "coding region," which is known in the art to refer to the region between the translation initiation codon and the translation termination codon, is also a region which may be targeted effectively. Within the context of the present invention, a preferred region is the intragenic region encompassing the translation initiation or termination codon of the open reading frame (ORF) of a gene.

Other target regions include the 5' untranslated region (5' UTR), known in the art to refer to the portion of an mRNA in the 5' direction from the translation initiation codon, and thus including nucleotides between the 5' cap site and the translation initiation codon of an mRNA (or corresponding nucleotides on the gene), and the 3' untranslated region (3' UTR), known in the art to refer to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap site. It is also preferred to target the 5' cap region.

Accordingly, the present invention provides antisense compounds that target a portion of nucleotides 1-1976 as set forth in SEQ ID NO: 4. In one embodiment, the antisense compounds target at least an 8 nucleobase portion of nucleotides 1-1976 as set forth in SEQ ID NO: 4. In another embodiment, the antisense compounds target at least an 8 nucleobase portion of nucleotides 1-244 comprising the 5' UTR as set forth in SEQ ID NO: 4. In another embodiment, the antisense compounds target at least an 8 nucleobase portion of nucleotides 1712-1976 comprising the 3' UTR as set forth in SEQ ID NO: 4. In another embodiment, the antisense compounds target at least an 8 nucleobase portion of nucleotides 245-1711 comprising the coding region as set forth in SEQ ID NO: 4. In still other embodiments, the antisense compounds target at least an 8 nucleobase portion of a "preferred target segment" (as defined herein) as set forth in Table 3.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. Targeting splice sites, i.e., intron-exon junctions or exon-intron junctions, may also be particularly useful in situations where aberrant splicing is implicated in disease, or where an overproduction of a particular splice product is implicated in disease. Aberrant fusion junctions due to rearrangements or deletions are also preferred target sites. mRNA transcripts produced via the process of splicing of two (or more) mRNAs from different gene sources are known as "fusion transcripts". It is also known that introns can be effectively targeted using antisense compounds targeted to, for example, DNA or pre-mRNA.

Alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and exonic sequence.

Upon excision of one or more exon or intron regions, or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

Variants can be produced through the use of alternative signals to start or stop transcription. Pre-mRNAs and mRNAs can possess more than one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. Within the context of the invention, the types of variants described herein are also preferred target nucleic acids.

The locations on the target nucleic acid to which the preferred antisense compounds hybridize are hereinbelow referred to as "preferred target segments." As used herein the term "preferred target segment" is defined as at least an 8-nucleobase portion of a target region to which an active antisense compound is targeted. While not wishing to be bound by theory, it is presently believed that these target segments represent portions of the target nucleic acid that are accessible for hybridization.

While the specific sequences of certain preferred target segments are set forth herein, one of skill in the art will recognize that these serve to illustrate and describe particular embodiments within the scope of the present invention. Additional preferred target segments may be identified by one having ordinary skill.

Target segments 8-80 nucleobases in length comprising a stretch of at least eight (8) consecutive nucleobases selected from within the illustrative preferred target segments are considered to be suitable for targeting as well.

Target segments can include DNA or RNA sequences that comprise at least the 8 consecutive nucleobases from the 5'-terminus of one of the illustrative preferred target segments (the remaining nucleobases being a consecutive stretch of the same DNA or RNA beginning immediately upstream of the 5'-terminus of the target segment and continuing until the DNA or RNA contains about 8 to about 80 nucleobases). Similarly preferred target segments are represented by DNA or RNA sequences that comprise at least the 8 consecutive nucleobases from the 3'-terminus of one of the illustrative preferred target segments (the remaining nucleobases being a consecutive stretch of the same DNA or RNA beginning immediately downstream of the 3'-terminus of the target segment and continuing until the DNA or RNA contains about 8 to about 80 nucleobases). One having skill in the art armed with the preferred target segments illustrated herein will be able, without undue experimentation, to identify further preferred target segments.

Once one or more target regions, segments or sites have been identified, antisense compounds are chosen which are sufficiently complementary to the target, i.e., hybridize sufficiently well and with sufficient specificity, to give the desired effect.

The oligomeric compounds are also targeted to or not targeted to regions of the target diacylglycerol acyltransferase 1 nucleobase sequence (e.g., such as those disclosed in Example 13) comprising nucleobases 1-50, 51-100, 101-150, 151-200, 201-250, 251-300, 301-350, 351-400, 401-450, 451-500, 501-550, 551-600, 601-650, 651-700, 701-750, 751-800, 801-850, 851-900, 901-950, 951-1000, 1001-1050, 1051-1100, 1101-1150, 1151-1200, 1201-1250, 1251-1300, 1301-1350, 1351-1400, 1401-1450, 1451-1500, 1501-1550, 1551-1600, 1601-1650, 1651-1700, 1701-1750, 1751-1800, 1801-1850, 1851-1900, 1901-1950, 1951-1976 of the diacylglycerol acyltransferase 1 sequence, or any combination thereof.

In one embodiment, the oligonucleotide compounds of this invention are 100% complementary to these sequences or to small sequences found within each of the above listed sequences. Preferably, the antisense compounds comprise at least 8 contiguous nucleobases of an antisense compound disclosed herein. In another embodiment the oligonucleotide compounds have from at least 3 or 5 mismatches per 20 consecutive nucleobases in individual nucleobase positions to these target regions. Still other compounds of the invention are targeted to overlapping regions of the above-identified portions of the diacylglycerol acyltransferase 1 sequence.

D. Screening and Target Validation

In a further embodiment, the "preferred target segments" identified herein may be employed in a screen for additional compounds that modulate the expression of diacylglycerol acyltransferase 1. "Modulators" are those compounds that decrease or increase the expression of a nucleic acid molecule encoding diacylglycerol acyltransferase 1 and which comprise at least an 8-nucleobase portion that is complementary to a preferred target segment. The screening method comprises the steps of contacting a preferred target segment of a nucleic acid molecule encoding diacylglycerol acyltransferase 1 with one or more candidate modulators, and selecting for one or more candidate modulators which decrease or increase the expression of a nucleic acid molecule encoding diacylglycerol acyltransferase 1. Once it is shown that the candidate modulator or modulators are capable of modulating (e.g. either decreasing or increasing) the expression of a nucleic acid molecule encoding diacylglycerol acyltransferase 1, the modulator may then be employed in further investigative studies of the function of diacylglycerol acyltransferase 1, or for use as a research, diagnostic, or therapeutic agent in accordance with the present invention.

The preferred target segments of the present invention may be also be combined with their respective complementary antisense compounds of the present invention to form stabilized double-stranded (duplexed) oligonucleotides.

Such double stranded oligonucleotide moieties have been shown in the art to modulate target expression and regulate translation as well as RNA processsing via an antisense mechanism. Moreover, the double-stranded moieties may be subject to chemical modifications (Fire et al., *Nature*, 1998, 391, 806-811; Timmons and Fire, *Nature* 1998, 395, 854; Timmons et al., *Gene*, 2001, 263, 103-112; Tabara et al., *Science*, 1998, 282, 430-431; Montgomery et al., *Proc. Natl. Acad. Sci. USA*, 1998, 95, 15502-15507; Tuschl et al., *Genes Dev.*, 1999, 13, 3191-3197; Elbashir et al., *Nature*, 2001, 411, 494-498; Elbashir et al., *Genes Dev.* 2001, 15, 188-200). For example, such double-stranded moieties have been shown to inhibit the target by the classical hybridization of antisense strand of the duplex to the target, thereby triggering enzymatic degradation of the target (Tijsterman et al., *Science*, 2002, 295, 694-697).

The compounds of the present invention can also be applied in the areas of drug discovery and target validation. The present invention comprehends the use of the compounds and preferred target segments identified herein in drug discovery efforts to elucidate relationships that exist between diacylglycerol acyltransferase 1 and a disease state, phenotype, or condition. These methods include detecting or modulating diacylglycerol acyltransferase 1 comprising contacting a sample, tissue, cell, or organism with the compounds of the present invention, measuring the nucleic acid or protein level of diacylglycerol acyltransferase 1 and/or a related phenotypic or chemical endpoint at some time after treatment, and optionally comparing the measured value to a non-treated sample or sample treated with a further compound of the invention. These methods can also be performed in parallel or in combination with other experiments to determine the function of unknown genes for the process of target validation or to determine the validity of a particular gene product as a target for treatment or prevention of a particular disease, condition, or phenotype.

E. Kits, Research Reagents, Diagnostics, and Therapeutics

The compounds of the present invention are utilized for diagnostics, therapeutics, prophylaxis and as research reagents and kits. In one embodiment, such compositions of the invention are useful in the areas of obesity and obesity-associated disorders, such as obesity-related insulin resistance. Furthermore, antisense oligonucleotides, which are able to inhibit gene expression with exquisite specificity, are often used by those of ordinary skill to elucidate the function of particular genes or to distinguish between functions of various members of a biological pathway.

For use in kits and diagnostics, the compounds of the present invention, either alone or in combination with other compounds or therapeutics, are used as tools in differential and/or combinatorial analyses to elucidate expression patterns of a portion or the entire complement of genes expressed within cells and tissues.

As used herein the term "system" is defined as any organism, cell, cell culture or tissue that expresses, or is made competent to express products of the gene encoding diacylglycerol acyltransferase 1. These include, but are not limited to, humans, transgenic animals, cells, cell cultures, tissues, xenografts, transplants and combinations thereof.

As one nonlimiting example, expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds that affect expression patterns.

Examples of methods of gene expression analysis known in the art include DNA arrays or microarrays (Brazma and Vilo, *FEBS Lett.*, 2000, 480, 17-24; Celis, et al., *FEBS Lett.*, 2000, 480, 2-16), SAGE (serial analysis of gene expression) (Madden, et al., *Drug Discov. Today*, 2000, 5, 415-425), READS (restriction enzyme amplification of digested cDNAs) (Prashar and Weissman, *Methods Enzymol.*, 1999, 303, 258-72), TOGA (total gene expression analysis) (Sutcliffe, et al., *Proc. Natl. Acad. Sci. U. S. A.*, 2000, 97, 1976-81), protein arrays and proteomics (Celis, et al., *FEBS Lett.*, 2000, 480, 2-16; Jungblut, et al., *Electrophoresis*, 1999, 20, 2100-10), expressed sequence tag (EST) sequencing (Celis, et al., *FEBS Lett.*, 2000, 480, 2-16; Larsson, et al., *J. Biotechnol.*, 2000, 80, 143-57), subtractive RNA fingerprinting (SuRF) (Fuchs, et al., *Anal. Biochem.*, 2000, 286, 91-98; Larson, et al., *Cytometry*, 2000, 41, 203-208), subtractive cloning, differential display (DD) (Jurecic and Belmont, *Curr. Opin. Microbiol.*, 2000, 3, 316-21), comparative genomic hybridization (Carulli, et al., *J. Cell Biochem. Suppl.*, 1998, 31, 286-96), FISH (fluorescent in situ hybridization) techniques (Going and Gusterson, *Eur. J. Cancer*, 1999, 35, 1895-904) and mass spectrometry methods (To, *Comb. Chem. High Throughput Screen*, 2000, 3, 235-41).

The compounds of the invention are useful for research and diagnostics, because these compounds hybridize to nucleic acids encoding diacylglycerol acyltransferase 1. For example, oligonucleotides that are shown to hybridize with such efficiency and under such conditions as disclosed herein as to be effective diacylglycerol acyltransferase 1 inhibitors will also be effective primers or probes under conditions favoring gene amplification or detection, respectively. These primers and probes are useful in methods requiring the specific detection of nucleic acid molecules encoding diacylglycerol acyltransferase 1 and in the amplification of said nucleic acid molecules for detection or for use in further studies of diacylglycerol acyltransferase 1. Hybridization of the antisense oligonucleotides, particularly the primers and probes, of the invention with a nucleic acid encoding diacylglycerol acyltransferase 1 can be detected by means known in the art. Such means may include conjugation of an enzyme to the oligonucleotide, radiolabelling of the oligonucleotide or any other suitable detection means. Kits using such detection means for detecting the level of diacylglycerol acyltransferase 1 in a sample may also be prepared.

Among diagnostic uses is the measurement of diacylglycerol acyltransferase 1 levels in patients to identify those who may benefit from a treatment strategy aimed at attenuation of inflammation. Such patients suitable for diagnosis include patients with obesity, or related disorders, including diabetes and cardiac disorders. Such disorders may be related to elevated serum glucose levels, elevated circulating insulin levels, elevated fasted serum insulin levels, elevated circulating triglycerides, elevated liver triglycerides and elevated free fatty acids in liver.

The specificity and sensitivity of antisense are also harnessed by those of skill in the art for therapeutic uses. Antisense compounds have been employed as therapeutic moieties in the treatment of disease states in animals, including humans. Antisense oligonucleotide drugs, including ribozymes, have been safely and effectively administered to humans and numerous clinical trials are presently underway. It is thus established that antisense compounds can be useful therapeutic modalities that can be configured to be useful in treatment regimes for the treatment of cells, tissues and animals, especially humans.

For therapeutics, an animal, preferably a human, suspected of having a disease or disorder which can be treated by modulating the expression of diacylglycerol acyltransferase 1 is treated by administering antisense compounds in accordance with this invention. For example, in one non-limiting embodiment, the methods comprise the step of administering to the animal in need of treatment, a therapeutically effective amount of a diacylglycerol acyltransferase 1 inhibitor. The diacylglycerol acyltransferase 1 inhibitors of the present invention effectively inhibit the activity of diacylglycerol acyltransferase 1 or inhibit the expression of diacylglycerol acyltransferase 1. For example, such a compound or composition that reduces levels of diacylglycerol acyltransferase 1 is useful to prevent morbidity and mortality for subjects with obesity-related disorders. For example, as demonstrated in the examples, reduction in DGAT1 can result in the reduction of elevated levels of serum glucose, circulating insulin, fasted serum, circulating triglycerides, liver triglycerides and free fatty acids in liver. Thus, DGAT-1 inhibitors are useful in the treatment of a variety of diabetes, obesity, and cardiac disorders, including acute coronary syndrome. Such a composition is useful for reducing inflammation mediated by diacylglycerol acyltransferase 1 in a subject, e.g., to treat or prevent or reduce the progression of, atherosclerosis; to treat or prevent or reduce the progression of, acute vascular damage at atherosclerotic plaque sites or in coronary arteries; or to treat or prevent or reduce the progression of, damage caused by inflammation associated with myocardial infarctions or renal inflammation. Still other therapeutic or prophylactic methods using diacylglycerol acyltransferase 1 inhibitory compounds of this invention include to treat patients with coronary artery stenting or liver disorders.

In one embodiment, the activity or expression of diacylglycerol acyltransferase 1 in an animal is inhibited by about 10%. Preferably, the activity or expression of diacylglycerol acyltransferase 1 in an animal is inhibited by about 30%. More preferably, the activity or expression of diacylglycerol acyltransferase 1 in an animal is inhibited by 50% or more. Thus, the oligomeric compounds modulate expression of diacylglycerol acyltransferase 1 mRNA by at least 10%, by at least 20%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100%.

For example, the reduction of the expression of diacylglycerol acyltransferase 1 may be measured in serum, adipose tissue, liver or any other body fluid, tissue or organ of the animal. Preferably, the cells contained within said fluids, tissues or organs being analyzed contain a nucleic acid molecule encoding diacylglycerol acyltransferase 1 and/or diacylglycerol acyltransferase 1 itself.

The compounds of the invention can be utilized in pharmaceutical compositions by adding an effective amount of a compound to a suitable pharmaceutically acceptable diluent or carrier. Use of the compounds and methods of the invention may also be useful prophylactically.

F. Modifications

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are generally preferred. In addition, linear compounds may have internal nucleobase complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Modified Internucleoside Linkages (Backbones)

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and borano-phosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage, i.e. a single inverted nucleoside residue that may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos.: 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos.: 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

Modified Sugar and Internucleoside Linkages-Mimetics

In other preferred oligonucleotide mimetics, both the sugar and the internucleoside linkage (i.e. the backbone), of the nucleotide units are replaced with novel groups. The nucleobase units are maintained for hybridization with an appropriate target nucleic acid. One such compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos.: 5,539,082; 5,714,331; and 5,719,262, each of which is herein incorporated by reference. Further teaching of PNA compounds can be found in Nielsen et al., *Science*, 1991, 254, 1497-1500.

Preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene(methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602, 240. Also preferred are oligonucleotides having morpholino backbone structures of the above-referenced U.S. Pat. No. 5,034,506.

Modified Sugars

Modified oligonucleotides may also contain one or more substituted sugar moieties. Preferred oligonucleotides comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$$CH_3$, O($CH_2$)$_n$O$CH_3$, O($CH_2$)$_n$N$H_2$, O($CH_2$)$_n$$CH_3$, O($CH_2$)$_n$ON$H_2$, and O($CH_2$)$_n$ON[($CH_2$)$_n$$CH_3$]$_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., *Helv. Chim. Acta*, 1995, 78, 486-504) i.e., an alkoxyalkoxy group. A further preferred modification includes 2'-dimethylaminooxyethoxy, i.e., a O($CH_2$)$_2$ON ($CH_3$)$_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—N($CH_3$)$_2$, also described in examples hereinbelow.

Other preferred modifications include 2'-methoxy (2'-O—$CH_3$), 2'-aminopropoxy (2'-O$CH_2CH_2CH_2NH_2$), 2'-allyl (2'-$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos.: 4,981,957; 5,118,800; 5,319, 080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

A further preferred modification of the sugar includes Locked Nucleic Acids (LNAs) in which the 2'-hydroxyl group is linked to the 3' or 4' carbon atom of the sugar ring, thereby forming a bicyclic sugar moiety. The linkage is preferably a methylene (—$CH_2$—)$_n$ group bridging the 2' oxygen atom and the 4' carbon atom wherein n is 1 or 2. LNAs and preparation thereof are described in International Patent Publication Nos. WO 98/39352 and WO 99/14226.

Natural and Modified Nucleobases

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido [5,4-b][1,4]benzoxazin-2(3H)-one), carbazole cytidine (2H- pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie, International Edition*, 1991, 30, 613, and those disclosed by Sanghvi, Y. S., Chapter 15, *Antisense Research and Applications*, pages 289-302, Crooke, S. T. and Lebleu, B., ed., *CRC Press*, 1993. Certain of these nucleobases are particularly useful for increasing the binding affinity of the compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos.: 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

Conjugates

Another modification of the oligonucleotides of the invention involves chemically linking to the oligonucleotide one or more moieties or conjugates that enhance the activity, cellular distribution or cellular uptake of the oligonucleotide. These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application PCT/US92/09196, filed Oct. 23, 1992, and U.S. Pat. No. 6,287,860, the entire disclosure of which are incorporated herein by reference. Conjugate moieties include but are not limited to lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethylammonium 1,2-di-o-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999), which is incorporated herein by reference in its entirety.

Representative United States patents that teach the preparation of such oligonucleotide conjugates include, but are not limited to, U.S. Pat. Nos.: 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

Chimeric Compounds

It is not necessary for all positions in a given compound to be uniformly modified, and in fact more than one of the aforementioned modifications may be incorporated in a single compound or even at a single nucleoside within an oligonucleotide.

The present invention also includes antisense compounds that are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, increased stability and/or increased binding affinity for the target nucleic acid. An additional region of the oligonucleotide may serve as a substrate for enzymes capable of cleaving RNA:DNA or RNA:RNA hybrids. By way of example, RNAse H is a cellular endonuclease which cleaves the RNA strand of an RNA:DNA duplex. Activation of RNase H, therefore, results in cleavage of the RNA target, thereby greatly enhancing the efficiency of oligonucleotide-mediated inhibition of gene expression. The cleavage of RNA:RNA hybrids can, in like fashion, be accomplished through the actions of endoribonucleases, such as RNAseL which cleaves both cellular and viral RNA. Cleavage of the RNA target can be routinely detected by gel electrophoresis and, if necessary, associated nucleic acid hybridization techniques known in the art.

In one embodiment, desirable chimeric oligonucleotides are 20 nucleotides in length, composed of a central region consisting of ten 2'-deoxynucleotides, flanked on both sides (5' and 3' directions) by five 2'-methoxyethyl (2'-MOE)$_n$ucleotides. The internucleoside linkages are phosphorothioate throughout the oligonucleotide and all cytidine residues are 5-methylcytidines.

In another embodiment certain preferred chimeric oligonucleotides are those disclosed in the Examples herein, particularly Example 15. Particularly preferred chimeric oligonucleotides are those referred to as ISIS 191643, ISIS 191647, ISIS 191635, and ISIS 191695.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos.: 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

G. Formulations

The compounds of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos.: 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal; including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in International Patent Publication No. WO 93/24510 to Gosselin et al., published Dec. 9, 1993, or in International Patent Publication No. WO 94/26764 and U.S. Pat. No. 5,770,713 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto. For oligonucleotides, preferred examples of pharmaceutically acceptable salts and their uses are further described in U.S. Pat. No. 6,287,860, which is incorporated herein in its entirety.

The present invention also includes pharmaceutical compositions and formulations that include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

Pharmaceutical compositions of the present invention include, but are not limited to, solutions, emulsions, foams and liposome-containing formulations. The pharmaceutical compositions and formulations of the present invention may comprise one or more penetration enhancers, carriers, excipients or other active or inactive ingredients.

Emulsions are typically heterogenous systems of one liquid dispersed in another in the form of droplets usually exceeding 0.1 μm in diameter. Emulsions may contain additional components in addition to the dispersed phases, and the active drug that may be present as a solution in either the aqueous phase., oily phase or itself as a separate phase. Microemulsions are included as an embodiment of the present invention. Emulsions and their uses are well known in the art and are further described in U.S. Pat. No. 6,287,860, which is incorporated herein in its entirety.

Formulations of the present invention include liposomal formulations. As used in the present invention, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes, which are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860, which is incorporated herein in its entirety.

The pharmaceutical formulations and compositions of the present invention may also include surfactants. The use of surfactants in drug products, formulations and in emulsions is well known in the art. Surfactants and their uses are further described in U.S. Pat. No. 6,287,860, which is incorporated herein in its entirety.

In one embodiment, the present invention employs various penetration enhancers to effect the efficient delivery of nucleic acids, particularly oligonucleotides. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860, which is incorporated herein in its entirety.

One of skill in the art will recognize that formulations are routinely designed according to their intended use, i.e. route of administration.

Preferred formulations for topical administration include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA).

For topical or other administration, oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters, pharmaceutically acceptable salts thereof, and their uses are further described in U.S. Pat. No. 6,287,860, which is incorporated herein in its entirety. Topical formulations are described in detail in U.S. patent application Ser. No. 09/315,298, filed on May 20, 1999, which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Preferred bile acids/salts and fatty acids and their uses are further described in U.S. Pat. No. 6,287,860, which is incorporated herein in its entirety. Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally, in granular form including sprayed dried particles, or complexed to form micro or nanoparticles. Oligonucleotide complexing agents and their uses are further described in U.S. Pat. No. 6,287,860, which is incorporated herein in its entirety. Oral formulations for oligonucleotides and their preparation are described in detail in U.S. Published Patent Application No. 2003/0040497 (Feb. 27, 2003) and its parent applications; U.S. Published Patent Application No. 2003/0027780 (Feb. 6, 2003) and its parent applications; and U.S. patent application Ser. No. 10/071,822, filed Feb. 8, 2002, each of which is incorporated herein by reference in their entirety.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Certain embodiments of the invention provide pharmaceutical compositions containing one or more oligomeric compounds and one or more other chemotherapeutic agents, which function by a non-antisense mechanism. Examples of such chemotherapeutic agents include but are not limited to cancer chemotherapeutic drugs such as daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxyco-formycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Combinations of antisense compounds and other non-antisense drugs are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Alternatively, compositions of the invention may contain two or more antisense compounds targeted to different regions of the same nucleic acid target. Numerous examples of antisense compounds are known in the art. Two or more combined compounds may be used together or sequentially.

H. Dosing

The formulation of therapeutic compositions and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 µg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 µg to 100 g per kg of body weight, once or more daily, to once every 20 years.

While the present invention has been described with specificity in accordance with certain of its preferred embodiments, the following examples serve only to illustrate the invention and are not intended to limit the same.

EXAMPLES

Example 1

Synthesis of Nucleoside Phosphoramidites

The following compounds, including amidites and their intermediates were prepared as described in U.S. Pat. No. 6,426,220 and International Patent Publication No. WO 02/36743; 5'-O-Dimethoxytrityl-thymidine intermediate for 5-methyl dC amidite, 5'-O-Dimethoxytrityl-2'-deoxy-5-methylcytidine intermediate for 5-methyl-dC amidite, 5'-O-Dimethoxytrityl-2'-deoxy-N4-benzoyl-5-methylcytidine penultimate intermediate for 5-methyl dC amidite, [5'-O-(4, 4'-Dimethoxytriphenylmethyl)-2'-deoxy-N$^4$-benzoyl-5-methylcytidin-3'-O-yl]-2-cyanoethyl-N,N-diisopropylphosphoramidite (5-methyl dC amidite), 2'-Fluorodeoxyadenosine, 2'-Fluorodeoxyguanosine, 2'-Fluorouridine, 2'-Fluorodeoxycytidine, 2'-O-(2-Methoxyethyl) modified amidites, 2'-O-(2-methoxyethyl)-5-methyluridine intermediate, 5'-O-DMT-2'-O-(2-methoxyethyl)-5-methyluridine penultimate intermediate, [5'-O-(4,4'-Dimethoxytriphenylmethyl)-2'-O-(2-methoxyethyl)-5-methyluridin-3'-O-yl]-2-cyanoethyl-N,N-diisopropylphosphoramidite (MOE T amidite), 5'-O-Dimethoxytrityl-2'-O-(2-methoxyethyl)-5-methylcytidine intermediate, 5'-O-dimethoxytrityl-2'-O-(2-methoxyethyl)-N$^4$-benzoyl-5-methyl-cytidine penultimate intermediate, [5'-O-(4,4'-Dimethoxytriphenylmethyl)-2'-O-(2-methoxyethyl)-N$^4$-benzoyl-5-methylcytidin-3'-O-yl]-2-cyanoethyl-N,N-diisopropylphosphoramidite (MOE 5-Me-C amidite), [5'-O-(4,4'-Dimethoxytriphenylmethyl)-2'-O-(2-methoxyethyl)-N$^6$-benzoyladenosin-3'-O-yl]-2-cyanoethyl-N,N-diisopropylphosphoramidite (MOE A amidite), [5'-O-(4,4'-Dimethoxytriphenylmethyl)-2'-O-(2-methoxyethyl)-N$^4$-isobutyrylguanosin-3'-O-yl]-2-cyanoethyl-N,N-diisopropylphosphoramidite (MOE G amidite), 2'-O-(Aminooxyethyl)nucleoside amidites and 2'-O-(dimethylamino-oxyethyl)nucleoside amidites, 2'-(Dimethylaminooxyethoxy)nucleoside amidites, 5'-O-tert-Butyldiphenylsilyl-O$^2$-2'-anhydro-5-methyluridine , 5'-O-tert-Butyldiphenylsilyl-2'-O-(2-hydroxyethyl)-5-methyluridine, 2'-O-([2-phthalimidoxy)ethyl]-5'-t-butyldiphenylsilyl-5-methyluridine 5'-O-tert-butyldiphenylsilyl-2'-O-[(2-formadoximinooxy)ethyl]-5-methyluridine, 5'-O-tert-Butyldiphenylsilyl-2'-O-[N,N dimethylaminooxyethyl]-5-methyluridine, 2'-O-(dimethylaminooxyethyl)-5-methyluridine, 5'-O-DMT-2'-O-(dimethylaminooxyethyl)-5-methyluridine, 5'-O-DMT-2'-O-(2-N,N-dimethylaminooxyethyl)-5-methyluridine-3'-[(2-cyanoethyl)-N,N-diisopropylphosphoramidite], 2'-(Aminooxyethoxy)nucleoside amidites, N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite](2'-DMAEOE) nucleoside amidites, 2'-O-[2(2-N,N-dimethylaminoethoxy)ethyl]-5-methyl uridine, 5'-O-dimethoxytrityl-2'-O-[2(2-N,N-dimethylaminoethoxy)-ethyl)]-5-methyl uridine and 5'-O-Dimethoxytrityl-2'-O-[2(2-N,N-dimethylaminoethoxy)-ethyl)]-5-methyl uridine-3'-O-(cyanoethyl-N,N-diisopropyl) phosphoramidite.

Example 2

Oligonucleotide and Oligonucleoside Synthesis

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

Oligonucleotides: Unsubstituted and substituted phosphodiester (P=O) oligonucleotides are synthesized on an automated DNA synthesizer (Applied Biosystems model 394) using standard phosphoramidite chemistry with oxidation by iodine.

Phosphorothioates (P=S) are synthesized similar to phosphodiester oligonucleotides with the following exceptions: thiation was effected by utilizing a 10% w/v solution of 3,H-1,2-benzodithiole-3-one 1,1-dioxide in acetonitrile for the oxidation of the phosphite linkages. The thiation reaction step time was increased to 180 sec and preceded by the normal capping step. After cleavage from the CPG column and deblocking in concentrated ammonium hydroxide at 55° C. (12-16 hr), the oligonucleotides were recovered by precipitating with >3 volumes of ethanol from a 1 M NH$_4$OAc solution. Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. Nos. 5,610,289 or 5,625,050, herein incorporated by reference.

Phosphoramidite oligonucleotides are prepared as described in U.S. Pat. Nos. 5,256,775 or 5,366,878, herein incorporated by reference.

Alkylphosphonothioate oligonucleotides are prepared as described in International Patent Application Nos. PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Oligonucleosides: Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 3

RNA Synthesis

In general, RNA synthesis chemistry is based on the selective incorporation of various protecting groups at strategic intermediary reactions. Although one of ordinary skill in the art will understand the use of protecting groups in organic synthesis, a useful class of protecting groups includes silyl ethers. In particular bulky silyl ethers are used to protect the 5'-hydroxyl in combination with an acid-labile orthoester protecting group on the 2'-hydroxyl. This set of protecting groups is then used with standard solid-phase synthesis technology. It is important to lastly remove the acid labile orthoester protecting group after all other synthetic steps. Moreover, the early use of the silyl protecting groups during synthesis ensures facile removal when desired, without undesired deprotection of 2' hydroxyl.

Following this procedure for the sequential protection of the 5'-hydroxyl in combination with protection of the 2'-hydroxyl by protecting groups that are differentially removed and are differentially chemically labile, RNA oligonucleotides were synthesized.

RNA oligonucleotides are synthesized in a stepwise fashion. Each nucleotide is added sequentially (3'- to 5'-direction) to a solid support-bound oligonucleotide. The first nucleoside at the 3'-end of the chain is covalently attached to a solid support. The nucleotide precursor, a ribonucleoside phosphoramidite, and activator are added, coupling the second base onto the 5'-end of the first nucleoside. The support is washed and any unreacted 5'-hydroxyl groups are capped with acetic anhydride to yield 5'-acetyl moieties. The linkage is then oxidized to the more stable and ultimately desired P(V) linkage. At the end of the nucleotide addition cycle, the 5'-silyl group is cleaved with fluoride. The cycle is repeated for each subsequent nucleotide.

Following synthesis, the methyl protecting groups on the phosphates are cleaved in 30 minutes utilizing 1 M disodium-2-carbamoyl-2-cyanoethylene-1,1-dithiolate trihydrate ($S_2Na_2$) in DMF. The deprotection solution is washed from the solid support-bound oligonucleotide using water. The support is then treated with 40% methylamine in water for 10 minutes at 55° C. This releases the RNA oligonucleotides into solution, deprotects the exocyclic amines, and modifies the 2'- groups. The oligonucleotides can be analyzed by anion exchange HPLC at this stage.

The 2'-orthoester groups are the last protecting groups to be removed. The ethylene glycol monoacetate orthoester protecting group developed by Dharmacon Research, Inc. (Lafayette, Colo.), is one example of a useful orthoester protecting group, which has the following important properties. It is stable to the conditions of nucleoside phosphoramidite synthesis and oligonucleotide synthesis. However, after oligonucleotide synthesis the oligonucleotide is treated with methylamine, which not only cleaves the oligonucleotide from the solid support but also removes the acetyl groups from the orthoesters. The resulting 2-ethyl-hydroxyl substituents on the orthoester are less electron-withdrawing than the acetylated precursor. As a result, the modified orthoester becomes more labile to acid-catalyzed hydrolysis. Specifically, the rate of cleavage is approximately 10 times faster after the acetyl groups are removed. Therefore, this orthoester possesses sufficient stability in order to be compatible with oligonucleotide synthesis and yet, when subsequently modified, permits deprotection to be carried out under relatively mild aqueous conditions compatible with the final RNA oligonucleotide product.

Additionally, methods of RNA synthesis are well known in the art (Scaringe, S. A. Ph.D. Thesis, University of Colorado, 1996; Scaringe, S. A., et al., *J. Am. Chem. Soc.*, 1998, 120, 11820-11821; Matteucci, M. D. and Caruthers, M. H. *J. Am. Chem. Soc.*, 1981, 103, 3185-3191; Beaucage, S. L. and Caruthers, M. H. *Tetrahedron Lett.*, 1981, 22, 1859-1862; Dahl, B. J., et al., *Acta Chem. Scand,.* 1990, 44, 639-641; Reddy, M. P., et al., *Tetrahedrom Lett.*, 1994, 25, 4311-4314; Wincott, F. et al., *Nucleic Acids Res.*, 1995, 23, 2677-2684; Griffin, B. E., et al., *Tetrahedron,* 1967, 23, 2301-2313; Griffin, B. E., et al., *Tetrahedron,* 1967, 23, 2315-2331).

RNA antisense compounds (RNA oligonucleotides) of the present invention can be synthesized by the methods herein or purchased from Dharmacon Research, Inc (Lafayette, Colo.). Once synthesized, complementary RNA antisense compounds can then be annealed by methods known in the art to form double stranded (duplexed) antisense compounds. For example, duplexes can be formed by combining 30 μl of each of the complementary strands of RNA oligonucleotides (50 uM RNA oligonucleotide solution) and 15 μl of 5× annealing buffer (100 mM potassium acetate, 30 mM HEPES-KOH pH 7.4, 2 mM magnesium acetate) followed by heating for 1 minute at 90° C., then 1 hour at 37° C. The resulting duplexed antisense compounds can be used in kits, assays, screens, or other methods to investigate the role of a target nucleic acid.

Example 4

Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O-Me]-[2'-deoxy]-[2'-O-Me] Chimeric Phosphorothioate Oligonucleotides

Chimeric oligonucleotides having 2'-O-alkyl phosphorothioate and 2'-deoxy phosphorothioate oligo-nucleotide segments are synthesized using an Applied Biosystems automated DNA synthesizer Model 394, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by incorporating coupling steps with increased reaction times for the 5'-dimethoxytrityl-2'-O-methyl-3'-O-phosphoramidite. The fully protected oligonucleotide is cleaved from the support and deprotected in concentrated ammonia (NH$_4$OH) for 12-16 hr at 55° C. The deprotected oligo is then recovered by an appropriate method (precipitation, column chromatography, volume reduced in vacuo and analyzed spectrophotometrically for yield and for purity by capillary electrophoresis and by mass spectrometry.

[2'-O-(2-Methoxyethyl)]-[2'-deoxy]-[2'-O-(Methoxyethyl)] Chimeric Phosphorothioate Oligonucleotides

[2'-O-(2-methoxyethyl)]-[2'-deoxy]-[-2'-O-(methoxyethyl)] chimeric phosphorothioate oligonucleotides were prepared as per the procedure above for the 2'-O-methyl chimeric oligonucleotide, with the substitution of 2'-O-(methoxyethyl)amidites for the 2'-O-methyl amidites.

[2'-O-(2-Methoxyethyl)Phosphodiester]-[2'-deoxy Phosphorothioate]-[2'-O-(2-Methoxyethyl)Phosphodiester] Chimeric Oligonucleotides

[2'-O-(2-methoxyethyl phosphodiester]-[2'-deoxy phosphorothioate]-[2'-O-(methoxyethyl)phosphodiester]chimeric oligonucleotides are prepared as per the above procedure for the 2'-O-methyl chimeric oligonucleotide with the substitution of 2'-O-(methoxyethyl)amidites for the 2'-O-methyl amidites, oxidation with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 5

Design and Screening of Duplexed Antisense Compounds Targeting Diacyiglycerol Acyltransferase 1

In accordance with the present invention, a series of nucleic acid duplexes comprising the antisense compounds of the present invention and their complements can be designed to target diacylglycerol acyltransferase 1. The nucleobase sequence of the antisense strand of the duplex comprises at least a portion of an oligonucleotide in Table 1. The ends of the strands may be modified by the addition of one or more natural or modified nucleobases to form an overhang. The sense strand of the dsRNA is then designed and synthesized as the complement of the antisense strand and may also contain modifications or additions to either terminus. For example, in one embodiment, both strands of the dsRNA duplex would be complementary over the central nucleobases, each having overhangs at one or both termini.

For example, a duplex comprising an antisense strand having the sequence CGAGAGGCGGACGGGACCG (SEQ ID NO: 228) and having a two-nucleobase overhang of deoxythymidine(dT) would have the following structure (Antisense SEQ ID NO: 229, Complement SEQ ID NO: 230):

```
cgagaggcggacgggaccgTT    Antisense Strand
||||||||||||||||||||
TTgctctccgcctgccctggc    Complement
```

In another embodiment, a duplex comprising an antisense strand having the same sequence CGAGAGGCGGACGGGACCG (SEQ ID NO: 228) may be prepared with blunt ends (no single stranded overhang) as shown (Antisense SEQ ID NO: 228, Complement SEQ ID NO: 231):

```
cgagaggcggacgggaccg    Antisense Strand
|||||||||||||||||||
gctctccgcctgccctggc    Complement
```

RNA strands of the duplex can be synthesized by methods disclosed herein or purchased from Dharmacon Research Inc., (Lafayette, Colo.). Once synthesized, the complementary strands are annealed. The single strands are aliquoted and diluted to a concentration of 50 µM. Once diluted, 30 µL of each strand is combined with 15 µL of a 5× solution of annealing buffer. The final concentration of said buffer is 100 mM potassium acetate, 30 mM HEPES-KOH pH 7.4, and 2mM magnesium acetate. The final volume is 75 µL. This solution is incubated for 1 minute at 90° C. and then centrifuged for 15 seconds. The tube is allowed to sit for 1 hour at 37° C. at which time the dsRNA duplexes are used in experimentation. The final concentration of the dsRNA duplex is 20 µM. This solution can be stored frozen (−20° C.) and freeze-thawed up to 5 times.

Once prepared, the duplexed antisense compounds are evaluated for their ability to modulate diacylglycerol acyltransferase 1 expression.

When cells reached 80% confluency, they are treated with duplexed antisense compounds of the invention. For cells grown in 96-well plates, wells are washed once with 200 µL OPTI-MEM-1™ reduced-serum medium (Gibco BRL) and then treated with 130 µL of OPTI-MEM-1™ medium containing 12 µg/mL LIPOFECTIN™ reagent (Gibco BRL) and the desired duplex antisense compound at a final concentration of 200 nM. After 5 hours of treatment, the medium is replaced with fresh medium. Cells are harvested 16 hours after treatment, at which time RNA is isolated and target reduction measured by RT-PCR.

Example 6

Oligonucleotide Isolation

After cleavage from the controlled pore glass solid support and deblocking in concentrated ammonium hydroxide at 55° C. for 12-16 hours, the oligonucleotides or oligonucleosides are recovered by precipitation out of 1 M $NH_4OAc$ with >3 volumes of ethanol. Synthesized oligonucleotides were analyzed by electrospray mass spectroscopy (molecular weight determination) and by capillary gel electrophoresis and judged to be at least 70% full-length material. The relative amounts of phosphorothioate and phosphodiester linkages obtained in the synthesis were determined by the ratio of correct molecular weight relative to the −16 amu product (+/−32+/−48). For some studies oligonucleotides were purified by HPLC, as described by Chiang et al., *J. Biol. Chem.* 1991, 266, 18162-18171. Results obtained with HPLC-purified material were similar to those obtained with non-HPLC purified material.

Example 7

Oligonucleotide Synthesis—96 Well Plate Format

Oligonucleotides were synthesized via solid phase P(III) phosphoramidite chemistry on an automated synthesizer capable of assembling 96 sequences simultaneously in a 96-well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphoramidites were purchased from commercial vendors (e.g. PE-Applied Biosystems, Foster City, Calif., or Pharmacia, Piscataway, N.J.). Non-standard nucleosides are synthesized as per standard or patented methods. They are utilized as base protected beta-cyanoethyldiisopropyl phosphoramidites.

Oligonucleotides were cleaved from support and deprotected with concentrated $NH_4OH$ at elevated temperature (55-60° C.) for 12-16 hours and the released product then dried in vacuo. The dried product was then re-suspended in sterile water to afford a master plate from which all analytical and test plate samples are then diluted utilizing robotic pipettors.

Example 8

Oligonucleotide Analysis—96-Well Plate Format

The concentration of oligonucleotide in each well was assessed by dilution of samples and UV absorption spectroscopy. The full-length integrity of the individual products was evaluated by capillary electrophoresis (CE) in either the 96-well format (Beckman P/ACE™ MDQ apparatus) or, for individually prepared samples, on a commercial CE apparatus (e.g., Beckman P/ACE™ 5000, ABI 270 apparatus). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 9

Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following cell types are provided for illustrative purposes, but other cell types can be routinely used, provided that the target is expressed in the cell type chosen. This can be readily determined by methods routine in the art, for example Northern blot analysis, ribonuclease protection assays, or RT-PCR.

T-24 Cells

The human transitional cell bladder carcinoma cell line T-24 was obtained from the American Type Culture Collection (ATCC) (Manassas, Va.). T-24 cells were routinely cultured in complete McCoy's 5A basal media (Invitrogen Corporation, Carlsbad, Calif.) supplemented with 10% fetal calf serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence. Cells were seeded into 96-well plates (Falcon-Primaria #353872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.

A549 Cells

The human lung carcinoma cell line A549 was obtained from the American Type Culture Collection (ATCC) (Manassas, Va.). A549 cells were routinely cultured in DMEM basal media (Invitrogen Corporation, Carlsbad, Calif.) supplemented with 10% fetal calf serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence.

NHDF Cells

Human neonatal dermal fibroblast (NHDF) were obtained from the Clonetics Corporation (Walkersville, Md.). NHDFs were routinely maintained in Fibroblast Growth Medium (Clonetics Corporation, Walkersville, Md.) supplemented as recommended by the supplier. Cells were maintained for up to 10 passages as recommended by the supplier.

HEK Cells

Human embryonic keratinocytes (HEK) were obtained from the Clonetics Corporation (Walkersville, Md.). HEKs were routinely maintained in Keratinocyte Growth Medium (Clonetics Corporation, Walkersville, Md.) formulated as recommended by the supplier. Cells were routinely maintained for up to 10 passages as recommended by the supplier.

HepG2 Cells

The human hepatoblastoma cell line HepG2 was obtained from the American Type Culture Collection (Manassas, Va.). HepG2 cells were routinely cultured in Eagle's MEM supplemented with 10% fetal calf serum, non-essential amino acids, and 1 mM sodium pyruvate (Gibco/Life Technologies, Gaithersburg, Md.). Cells were routinely passaged by trypsinization and dilution when they reached 90% confluence. Cells were seeded into 96-well plates (Falcon-Primaria #3872) at a density of 7000 cells/well for use in RT-PCR analysis.

For Northern blotting or other analyses, cells may be seeded onto 100 mm or other standard tissue culture plates and treated similarly, using appropriate volumes of medium and oligonucleotide.

b.END Cells

The mouse brain endothelial cell line b.END was obtained from Dr. Werner Risau at the Max Plank Institute (Bad Nauheim, Germany). b.END cells were routinely cultured in DMEM supplemented with 10% fetal bovine serum (Gibco/Life Technologies, Gaithersburg, Md.). Cells were routinely passaged by trypsinization and dilution when they reached 90% confluence. Cells were seeded into 24-well plates (Falcon-Primaria #3047) at a density of 40,000 cells/well for use in RT-PCR analysis.

For Northern blotting or other analyses, cells may be seeded onto 100 mm or other standard tissue culture plates and treated similarly, using appropriate volumes of medium and oligonucleotide.

Primary Rat Hepatocytes

Primary rat hepatocytes are prepared from Sprague-Dawley rats purchased from Charles River Labs (Wilmington, Mass.) and are routinely cultured in DMEM, high glucose (Invitrogen, Carlsbad, Calif.) supplemented with 10% fetal bovine serum (Invitrogen, Carlsbad, Calif.), 100 units per mL penicillin, and 100 µg/mL streptomycin (Invitrogen, Carlsbad, Calif.). Cells are seeded into 96-well plates (Falcon-Primaria #353872, BD Biosciences, Bedford, Mass.) at a density of 4000-6000 cells/well for treatment with the oligomeric compounds of the invention.

Treatment with Antisense Compounds

When cells reached 65-75% confluency, they were treated with oligonucleotide. For cells grown in 24-well plates, wells were washed once with 400 µL Eagle's DMEM and then treated with 100 µL of Eagle's DMEM containing 3.75 µg/mL LIPOFECTIN™ reagent (Invitrogen Corporation, Carlsbad, Calif.) and the desired concentration of oligonucleotide. Cells are treated and data are obtained in triplicate. After 4-7 hours of treatment at 37° C., the medium was replaced with Eagle's DMEM supplemented with 10% fetal bovine serum. Cells were harvested 20-24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is selected from either ISIS 13920 (TCCGTCATCGCTCCT-CAGGG, SEQ ID NO: 1) which is targeted to human H-ras, or ISIS 18078, (GTGCGCGCGAGCCCGAAATC, SEQ ID NO: 2) which is targeted to human Jun-N-terminal kinase-2 (JNK2). Both controls are 2'-O-methoxyethyl gapmers (2'-O-methoxyethyls shown in bold) with a phosphorothioate backbone. For mouse or rat cells the positive control oligonucleotide is ISIS 15770, ATGCATTCTGCCCCCAAGGA, SEQ ID NO: 3, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-H-ras (for ISIS 13920), JNK2 (for ISIS 18078) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of c-H-ras, JNK2 or c-raf mRNA is then utilized as the oligonucleotide screening concentration in subsequent experiments for that cell line. If 60% inhibition is not achieved, that particular cell line is deemed as unsuitable for oligonucleotide transfection experiments. The concentrations of antisense oligonucleotides used herein are from 50 nM to 300 nM.

Example 10

Analysis of Oligonucleotide Inhibition of Diacylglycerol Acyltransferase 1 Expression Antisense modulation of diacylglycerol acyltransferase 1 expression can be assayed in a variety of ways known in the art. For example, diacylglycerol acyltransferase 1 mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+ mRNA. The preferred method of RNA analysis of the present invention is the use of total cellular RNA as described in other examples herein. Methods of RNA isolation are well known in the art. Northern blot analysis is also routine in the art. Real-time quantitative (PCR) can be conveniently accomplished using the commercially available ABI PRISM™ 7600, 7700, or 7900 Sequence Detection System, available from PE-Applied Biosystems, Foster City, Calif. and used according to manufacturer's instructions.

Protein levels of diacylglycerol acyltransferase 1 can be quantitated in a variety of ways well known in the art, such as immunoprecipitation, Western blot analysis (immunoblotting), enzyme-linked immunosorbent assay (ELISA) or fluorescence-activated cell sorting (FACS). Antibodies directed to diacylglycerol acyltransferase 1 can be identified and obtained from a variety of sources, such as the MSRS catalog of antibodies (Aerie Corporation, Birmingham, Mich.), or can be prepared via conventional monoclonal or polyclonal antibody generation methods well known in the art.

Example 11

Design of Phenotypic Assays and in vivo Studies for the Use of Diacylglycerol Acyltransferase 1 Inhibitors Phenotypic Assays Once diacylglycerol acyltransferase 1 inhibitors have been identified by the methods disclosed herein, the compounds are further investigated in one or more phenotypic assays, each having measurable endpoints predictive of efficacy in the treatment of a particular disease state or condition.

Phenotypic assays, kits and reagents for their use are well known to those skilled in the art and are herein used to investigate the role and/or association of diacylglycerol acyltransferase 1 in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with diacylglycerol acyltransferase 1 inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status, which include pH, stage of the cell cycle, intake or excretion of biological indicators by the cell, are also endpoints of interest.

Analysis of the genotype of the cell (measurement of the expression of one or more of the genes of the cell) after treatment is also used as an indicator of the efficacy or potency of the diacylglycerol acyltransferase 1 inhibitors. Hallmark genes, or those genes suspected to be associated with a specific disease state, condition, or phenotype, are measured in both treated and untreated cells.

In vivo Studies

The individual subjects of the in vivo studies described herein are warm-blooded vertebrate animals, which includes humans.

The clinical trial is subjected to rigorous controls to ensure that individuals are not unnecessarily put at risk and that they are fully informed about their role in the study. To account for the psychological effects of receiving treatments, volunteers are randomly given placebo or diacylglycerol acyltransferase 1 inhibitor. Furthermore, to prevent the doctors from being biased in treatments, they are not informed as to whether the medication they are administering is a diacylglycerol acyltransferase 1 inhibitor or a placebo. Using this randomization approach, each volunteer has the same chance of being given either the new treatment or the placebo.

Volunteers receive either the diacylglycerol acyltransferase 1 inhibitor or placebo for eight week period with biological parameters associated with the indicated disease state or condition being measured at the beginning (baseline measurements before any treatment), end (after the final treatment), and at regular intervals during the study period. Such measurements include the levels of nucleic acid molecules encoding diacylglycerol acyltransferase 1 or the level of diacylglycerol acyltransferase 1 in body fluids, tissues or organs compared to pre-treatment levels. Other measurements include, but are not limited to, indices of the disease state or condition being treated, body weight, blood pressure, serum titers of pharmacologic indicators of disease or toxicity as well as ADME (absorption, distribution, metabolism and excretion) measurements.

Information recorded for each patient includes age (years), gender, height (cm), family history of disease state or condition (yes/no), motivation rating (some/moderate/great) and number and type of previous treatment regimens for the indicated disease or condition.

Volunteers taking part in this study are healthy adults (age 18 to 65 years) and roughly an equal number of males and females participate in the study. Volunteers with certain characteristics are equally distributed for placebo and diacylglycerol acyltransferase 1 inhibitor treatment. In general, the volunteers treated with placebo have little or no response to treatment, whereas the volunteers treated with the diacylglycerol acyltransferase 1 inhibitor show positive trends in their disease state or condition index at the conclusion of the study.

Example 12

RNA Isolation

Poly(A)+ mRNA Isolation

Poly(A)+ mRNA was isolated according to Miura et al., (*Clin. Chem.*, 1996, 42, 1758-1764). Other methods for poly (A)+ mRNA isolation are routine in the art. Briefly, for cells grown on 96-well plates, growth medium was removed from the cells and each well was washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 µL of lysate was transferred to Oligo d(T) coated 96-well plates (AGCT Inc., Irvine Calif.). Plates were incubated for 60 minutes at room temperature, washed 3 times with 200 µL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 µL of elution buffer (5 mM Tris-HCl pH 7.6), preheated to 70° C., was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Total RNA Isolation

Total RNA was isolated using an RNEASY 96™ kit and buffers purchased from Qiagen Inc. (Valencia, Calif.) following the manufacturer's recommended procedures. Briefly, for cells grown on 96-well plates, growth medium was removed from the cells and each well was washed with 200 µL cold, PBS. 150 µL Buffer RLT was added to each well and the plate vigorously agitated for 20 seconds. 150 µL of 70% ethanol was then added to each well and the contents mixed by pipetting three times up and down. The samples were then transferred to the RNEASY 96™ well plate attached to a QIAVAC™ manifold fitted with a waste collection tray and attached to a vacuum source. Vacuum was applied for 1 minute. 500 µL of Buffer RW1 was added to each well of the RNEASY 96™ plate and incubated for 15 minutes and the vacuum was again applied for 1 minute. An additional 500 µL of Buffer RW1 was added to each well of the RNEASY 96™ plate and the vacuum was applied for 2 minutes. 1 mL of Buffer RPE was then added to each well of the RNEASY 96™ plate and the vacuum applied for a period of 90 seconds. The Buffer RPE wash was then repeated and the vacuum was applied for an additional 3 minutes.

The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 140 µL of RNAse free water into each well, incubating 1 minute, and then applying the vacuum for 3 minutes.

The repetitive pipetting and elution steps may be automated using a QIAGEN® Bio-Robot™ 9604 (Qiagen, Inc., Valencia Calif.). Essentially, after lysing of the cells on the culture plate, the plate is transferred to the robot deck where the pipetting, DNase treatment and elution steps are carried out.

Example 13

Real-time Quantitative PCR Analysis of Diacylglycerol Acyltransferase 1 mRNA Levels Quantitation of diacylglycerol acyltransferase 1 mRNA levels was accomplished by real-time quantitative PCR using the ABI PRISMS 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe.

When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ Sequence Detection System.

In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

PCR reagents were obtained from Invitrogen Corporation, (Carlsbad, Calif.). RT-PCR reactions were carried out by adding 30 µL PCR cocktail (2.5×PCR buffer minus $MgCl_2$, 6.6 mM $MgCl_2$, 375 µM each of dATP, dCTP, dCTP and dGTP, 375 nM each of forward primer and reverse primer, 125 nM of probe, 4 Units RNAse inhibitor, 1.25 Units PLATINUM® Taq enzyme, 5 Units MuLV reverse transcriptase, and 2.5×ROX dye) to 96-well plates containing 20 µL total RNA solution (20-200 ng). The RT reaction was carried out by incubation for 30 minutes at 48° C. Following a 10 minute incubation at 95° C. to activate the PLATINUM® Taq enzyme, 45 cycles of a two-step PCR protocol were carried out: 95° C. for 15 seconds (denaturation) followed by 60° C. for 1.5 minutes (annealing/extension).

Gene target quantities obtained by real time RT-PCR are normalized using either the expression level of GAPDH, a gene whose expression is constant, or by quantifying total RNA using RiboGreen™ reagent (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent (Molecular Probes, Inc. Eugene, Oreg.). Methods of RNA quantification by RiboGreen reagent are taught in Jones, L. J., et al, (*Analytical Biochemistry*, 1998, 265, 368-374).

In this assay, 180 µL of RiboGreen™ working reagent (RiboGreen™ reagent diluted 1:350 in 10 mM Tris-HCl, 1 mM EDTA, pH 7.5) is pipetted into a 96-well plate containing 20 µL purified, cellular RNA. The plate is read in a CytoFluor 4000 reader (PE Applied Biosystems) with excitation at 485 nm and emission at 530 nm.

Probes and primers to human diacylglycerol acyltransferase 1 were designed to hybridize to a human diacylglycerol acyltransferase 1 sequence, using published sequence information (GenBank accession number NM_012079.2, incorporated herein as SEQ ID NO: 4). For human diacylglycerol acyltransferase 1 the PCR primers were: forward primer: TCCCCGCATCCGGAA (SEQ ID NO: 5) reverse primer: CTGGGTGAAGAACAGCATCTC (SEQ ID NO: 6) and the PCR probe was: FAM-CGCTTTCTGCTGCGACGGATCC-TAMRA (SEQ ID NO: 7) where FAM is the fluorescent dye and TAMRA is the quencher dye. For human GAPDH the PCR primers were: forward primer: GAAGGTGAAG-GTCGGAGTC(SEQ ID NO: 8) reverse primer: GAAGATG-GTGATGGGATTTC (SEQ ID NO: 9) and the PCR probe was: 5' JOE-CAAGCTTCCCGTTCTCAGCC- TAMRA 3' (SEQ ID NO: 10) where JOE is the fluorescent reporter dye and TAMRA is the quencher dye.

Probes and primers to mouse diacylglycerol acyltransferase 1 were designed to hybridize to a mouse diacylglycerol acyltransferase 1 sequence, using published sequence information (GenBank accession number AF078752.1, incorporated herein as SEQ ID NO: 11). For mouse diacylglycerol acyltransferase 1 the PCR primers were: forward primer: GTTCCGCCTCTGGGCATT (SEQ ID NO: 12) reverse primer: GAATCGGCCCACAATCCalif. (SEQ ID NO: 13) and the PCR probe was: FAM-CAGCCATGATGGCTCAG-GTCCCACT-TAMRA (SEQ ID NO: 14) where FAM is the fluorescent reporter dye and TAMRA is the quencher dye. For mouse GAPDH the PCR primers were:

forward primer: GGCAAATTCAACGGCACAGT(SEQ ID NO: 15) reverse primer: GGGTCTCGCTCCTGGAAGAT (SEQ ID NO: 16) and the PCR probe was: 5' JOE-AAGGC-CGAGAATGGGAAGCTTGTCATC- TAMRA 3' (SEQ ID NO: 17) where JOE is the fluorescent reporter dye and TAMRA is the quencher dye.

Example 14

Northern Blot Analysis of Diacylglycerol Acyltransferase 1 mRNA Levels

Eighteen hours after antisense treatment, cell monolayers were washed twice with cold PBS and lysed in 1 mL RNA-ZOL™ reagent (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBOND™-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ UV Crosslinker 2400' (Stratagene, Inc, La Jolla, Calif.) and then probed using QUICKHYB™ hybridization solution (Stratagene, La Jolla, Calif.) using manufacturer's recommendations for stringent conditions.

To detect human diacylglycerol acyltransferase 1, a human diacylglycerol acyltransferase 1 specific probe was prepared by PCR using the forward primer TCCCCGCATCCGGAA (SEQ ID NO: 5) and the reverse primer CTGGGTGAAGAACAGCATCTC (SEQ ID NO: 6). To normalize for variations in loading and transfer efficiency membranes were stripped and probed for human glyceraldehyde-3-phosphate dehydrogenase (GAPDH) RNA (Clontech, Palo Alto, Calif.).

To detect mouse diacylglycerol acyltransferase 1, a mouse diacylglycerol acyltransferase 1 specific probe was prepared by PCR using the forward primer GTTCCGCCTCTGGGCATT (SEQ ID NO: 12) and the reverse primer GAATCGGCCCACAATCCA (SEQ ID NO: 13). To normalize for variations in loading and transfer efficiency membranes were stripped and probed for mouse glyceraldehyde-3-phosphate dehydrogenase (GAPDH) RNA (Clontech, Palo Alto, Calif.).

Hybridized membranes were visualized and quantitated using a PHOSPHORIMAGER™ apparatus and IMAGEQUANT™ Software V3.3 (Molecular Dynamics, Sunnyvale, Calif.). Data was normalized to GAPDH levels in untreated controls.

Example 15

Antisense Inhibition of Human Diacylglycerol Acyltransferase 1 Expression by Chimeric Phosphorothioate Oligonucleotides Having 2'-MOE Wings and a Deoxy Gap In accordance with the present invention, a series of antisense compounds was designed to target different regions of the human diacylglycerol acyltransferase 1 RNA, using published sequences (GenBank accession number NM_012079.2, incorporated herein as SEQ ID NO: 4). The compounds are shown in Table 1. "Target site" indicates the first (5'-most) nucleotide number on the particular target sequence to which the compound binds. All compounds in Table 1 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines. The compounds were analyzed for their effect on human diacylglycerol acyltransferase 1 mRNA levels by quantitative real-time PCR as described in other examples herein. Data are averages from three experiments in which HepG2 cells were treated with 75 nM of the antisense oligonucleotides of the present invention. The positive control for each data point is identified in the table by sequence ID number. If present, "N.D." indicates "no data".

TABLE 1

Inhibition of human diacylglycerol acyltransferase 1 mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 191617 | 5'UTR | 4 | 1 | gccgcctctctcgtccattc | 57 | 18 | 1 |
| 191619 | 5'UTR | 4 | 21 | gagccgctaactaatggacg | 37 | 19 | 1 |
| 191621 | 5'UTR | 4 | 41 | acaacggctgcgttgctccg | 30 | 20 | 1 |
| 191623 | 5'UTR | 4 | 71 | ccgcccgcgtcaggcccgtc | 40 | 21 | 1 |
| 191625 | 5'UTR | 4 | 91 | gcctcaccagcgcgttcaac | 20 | 22 | 1 |
| 191627 | 5'UTR | 4 | 120 | ccctgccggccgccgtagcc | 24 | 23 | 1 |
| 191629 | 5'UTR | 4 | 151 | ctccgggccctagacaacgg | 45 | 24 | 1 |
| 191631 | 5'UTR | 4 | 181 | gttcgtagcgcccgaggcgc | 53 | 25 | 1 |
| 191633 | 5'UTR | 4 | 211 | cccggccgcagccaagcgtg | 44 | 26 | 1 |
| 191635 | Start Codon | 4 | 231 | gcccatggcctcagcccgca | 77 | 27 | 1 |
| 191637 | Coding | 4 | 281 | tggctcgagggccgcgaccc | 58 | 28 | 1 |

TABLE 1-continued

Inhibition of human diacylglycerol acyltransferase 1 mRNA
levels by chimeric phosphorothioate oligonucleotides
having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 191639 | Coding | 4 | 301 | ccgcaggcccgccgccgccg | 49 | 29 | 1 |
| 191641 | Coding | 4 | 321 | ccgcacctcttcttccgccg | 40 | 30 | 1 |
| 191643 | Coding | 4 | 401 | acgccggcgtctccgtcctt | 92 | 31 | 1 |
| 191645 | Coding | 4 | 421 | gctcccagtggccgctgccc | 60 | 32 | 1 |
| 191647 | Coding | 4 | 441 | ctgcaggcgatggcacctca | 85 | 33 | 1 |
| 191649 | Coding | 4 | 491 | aggatgccacggtagttgct | 62 | 34 | 1 |
| 191651 | Coding | 4 | 511 | gcatcaccacacaccagttc | 37 | 35 | 1 |
| 191653 | Coding | 4 | 561 | gccatacttgatgaggttct | 48 | 36 | 1 |
| 191655 | Coding | 4 | 651 | gacattggccgcaataacca | 47 | 37 | 1 |
| 191657 | Coding | 4 | 681 | cttctcaacctggaatgcag | 29 | 38 | 1 |
| 191659 | Coding | 4 | 721 | gcagtcccgcctgctccgtc | 50 | 39 | 1 |
| 191661 | Coding | 4 | 741 | caggttggctacgtgcagca | 31 | 40 | 1 |
| 191663 | Coding | 4 | 781 | ccagtaagaccacagccgct | 62 | 41 | 1 |
| 191665 | Coding | 4 | 831 | ggtgtgcgccatcagcgcca | 59 | 42 | 1 |
| 191667 | Coding | 4 | 931 | cagcactgctggccttcttc | 52 | 43 | 1 |
| 191669 | Coding | 4 | 1021 | tgagctcgtagcacaaggtg | 43 | 44 | 1 |
| 191671 | Coding | 4 | 1121 | cactgctggatcagccccac | 20 | 45 | 1 |
| 191673 | Coding | 4 | 1181 | atgcgtgagtagtccatgtc | 59 | 46 | 1 |
| 191675 | Coding | 4 | 1231 | tgagccagatgaggtgattg | 62 | 47 | 1 |
| 191677 | Coding | 4 | 1281 | gagctcagccacggcattca | 76 | 48 | 1 |
| 191679 | Coding | 4 | 1351 | tctgccagaagtaggtgaca | 30 | 49 | 1 |
| 191681 | Coding | 4 | 1611 | gatgagcgacagccacacag | 21 | 50 | 1 |
| 191683 | Coding | 4 | 1671 | ctcatagttgagcacgtagt | 73 | 51 | 1 |
| 191685 | 3'UTR | 4 | 1721 | cagtgagaagccaggccctc | 68 | 52 | 1 |
| 191687 | 3'UTR | 4 | 1781 | ccatccccagcactcgaggc | 68 | 53 | 1 |
| 191689 | 3'UTR | 4 | 1801 | aggatgctgtgcagccaggc | 73 | 54 | 1 |
| 191691 | 3'UTR | 4 | 1851 | ggtgcaggacagagccccat | 72 | 55 | 1 |
| 191693 | 3'UTR | 4 | 1881 | gtgtctggcctgctgtcgcc | 71 | 56 | 1 |
| 191695 | 3'UTR | 4 | 1901 | ctcccagctggcatcagact | 76 | 57 | 1 |

As shown in Table 1, SEQ ID Nos. 18, 25, 27, 28, 31, 32, 33, 34, 39, 41, 42, 43, 46, 47, 48, 51, 52, 53, 54, 55, 56 and 57 demonstrated at least 50% inhibition of human diacylglycerol acyltransferase 1 expression in this assay and are therefore preferred. More preferred are SEQ ID NOs 31, 33, 27, and 57. The target regions to which these preferred sequences are complementary are herein referred to as "preferred target segments" and are therefore preferred for targeting by compounds of the present invention. These preferred target segments are shown in Table 3. The sequences represent the reverse complement of the preferred antisense compounds shown in Table 1. "Target site" indicates the first (5'-most) nucleotide number on the particular target nucleic acid to which the oligonucleotide binds. Also shown in Table 3 is the species in which each of the preferred target segments was found.

Example 16

Antisense Inhibition of Mouse Diacylglycerol Acyltransferase 1 Expression by Chimeric Phosphorothioate Oligonucleotides Having 2'-MOE Wings and a Deoxy Gap In accordance with the present invention, a second series of antisense compounds was designed to target different regions of the mouse diacylglycerol acyltransferase 1 RNA, using published sequences (GenBank accession number AF078752.1, incorporated herein as SEQ ID NO: 11). The compounds are shown in Table 2. "Target site" indicates the first (5'-most) nucleotide number on the particular target nucleic acid to which the compound binds. All compounds in Table 2 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'MOE)nucleotides. The internucleoside (backbone) linkages are phosphorothioate (P=S) throughout the oligonucleotide. All cytidine residues are 5-methylcytidines. The compounds were analyzed for their effect on mouse diacylglycerol acyltransferase 1 mRNA levels by quantitative real-time PCR as described in other examples herein. Data are averages from three experiments in which b.END cells were treated with the antisense oligonucleotides of the present invention. If present, "N.D." indicates "no data".

TABLE 2

Inhibition of mouse diacylglycerol acyltransferase 1 mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 191723 | 5'UTR | 11 | 1 | ctacttatttccattcatcc | 2 | 58 |
| 191724 | 5'UTR | 11 | 21 | tatcctaagtatgcctaatt | 0 | 59 |
| 191725 | 5'UTR | 11 | 31 | gcttgagccctatcctaagt | 0 | 60 |
| 191726 | 5'UTR | 11 | 61 | ctcgtcgcggcccaatcttc | 21 | 61 |
| 191727 | Start Codon | 11 | 81 | cccatggcttcggcccgcac | 48 | 62 |
| 191729 | Coding | 11 | 191 | cagccgcgtctcgcacctcg | 74 | 63 |
| 191730 | Coding | 11 | 232 | cggagccggcgcgtcacccc | 63 | 64 |
| 191731 | Coding | 11 | 281 | ccacgctggtccgcccgtct | 67 | 65 |
| 191732 | Coding | 11 | 301 | cagatcccagtagccgtcgc | 59 | 66 |
| 191733 | Coding | 11 | 321 | tcttgcagacgatggcacct | 49 | 67 |
| 191734 | Coding | 11 | 371 | tcaggataccacgataattg | 48 | 68 |
| 191735 | Coding | 11 | 391 | cagcatcaccacacaccaat | 52 | 69 |
| 191736 | Coding | 11 | 411 | aaccttgcattactcaggat | 62 | 70 |
| 191737 | Coding | 11 | 451 | atccaccaggatgccatact | 29 | 71 |
| 191738 | Coding | 11 | 471 | agagacaccacctggatagg | 42 | 72 |
| 191740 | Coding | 11 | 601 | cagcagcccatctgctctg | 63 | 73 |
| 191741 | Coding | 11 | 621 | gccaggttaaccacatgtag | 58 | 74 |
| 191742 | Coding | 11 | 661 | aaccagtaaggccacagctg | 16 | 75 |
| 191743 | Coding | 11 | 681 | cccactggagtgatagactc | 42 | 76 |
| 191744 | Coding | 11 | 711 | atggagtatgatgccagagc | 53 | 77 |
| 191745 | Coding | 11 | 771 | acccttcgctggcggcacca | 68 | 78 |
| 191746 | Coding | 11 | 841 | tggatagctcacagcttgct | 56 | 79 |
| 191747 | Coding | 11 | 861 | tctcggtaggtcaggttgtc | 32 | 80 |
| 191748 | Coding | 11 | 961 | ctcaagaactcgtcgtagca | 60 | 81 |
| 191749 | Coding | 11 | 1001 | gttggatcagcccacttga | 37 | 82 |

TABLE 2-continued

Inhibition of mouse diacylglycerol acyltransferase 1 mRNA
levels by chimeric phosphorothioate oligonucleotides
having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 191750 | Coding | 11 | 1061 | gtgaatagtccatatccttg | 48 | 83 |
| 191751 | Coding | 11 | 1081 | taagagacgctcaatgatcc | 18 | 84 |
| 191752 | Coding | 11 | 1161 | tctgccacagcattgagaca | 50 | 85 |
| 191753 | Coding | 11 | 1201 | ccaatctctgtagaactcgc | 55 | 86 |
| 191754 | Coding | 11 | 1221 | gtgacagactcagcattcca | 56 | 87 |
| 191755 | Coding | 11 | 1271 | gtctgatgcaccacttgtgc | 72 | 88 |
| 191756 | Coding | 11 | 1301 | tgccatgtctgagcataggc | 70 | 89 |
| 191757 | Coding | 11 | 1331 | atactcctgtcctggccacc | 65 | 90 |
| 191759 | Coding | 11 | 1471 | attgccatagttcccttgga | 68 | 91 |
| 191760 | Coding | 11 | 1491 | agtgtcacccacacagctgc | 66 | 92 |
| 191761 | Coding | 11 | 1511 | ccaccggttgcccaatgatg | 71 | 93 |
| 191762 | Coding | 11 | 1531 | gtggacatacatgagcacag | 62 | 94 |
| 191763 | Coding | 11 | 1551 | tagttgagcacgtagtagtc | 40 | 95 |
| 191764 | Stop Codon | 11 | 1586 | ctttggcagtagctcatacc | 37 | 96 |
| 191765 | 3'UTR | 11 | 1621 | tccagaactccaggcccagg | 59 | 97 |

As shown in Table 2, SEQ ID Nos. 63, 64, 65, 66, 69, 70, 73, 74, 77, 78, 79, 81, 85, 86, 87, 88, 89, 90, 9.1, 92, 93, 94 and 97 demonstrated at least 50% inhibition of mouse diacylglycerol acyltransferase 1 expression in this experiment and are therefore preferred. More preferred are SEQ ID Nos. 63, 88, 91, and 93. The target regions to which these preferred sequences are complementary are herein referred to as "preferred target segments" and are therefore preferred for targeting by compounds of the present invention. These preferred target segments of the mRNA are shown in Table 3 as the appropriate RNA sequence, where thymine (T) has been replaced with uracil (U) to reflect correct representation of an RNA sequence. The sequences represent the reverse complement of the preferred antisense compounds shown in Tables 1 and 2. "Target site" indicates the first (5'-most) nucleotide number on the particular target nucleic acid to which the oligonucleotide binds. Also shown in Table 3 is the species in which each of the preferred target segments was found.

TABLE 3

Sequence and position of preferred target segments
identified in diacylglycerol acyltransferase 1.

| SITE ID | TARGET SEQ ID NO | TARGET SITE | SEQUENCE | REV COMP OF SEQ ID | ACTIVE IN | SEQ ID NO |
|---|---|---|---|---|---|---|
| 108088 | 4 | 1 | gaauggacgagagaggcggc | 18 | H. sapiens | 98 |
| 108094 | 4 | 151 | ccguugucuagggcccggag | 24 | H. sapiens | 99 |
| 108095 | 4 | 181 | gcgccucgggcgcuacgaac | 25 | H. sapiens | 100 |
| 108096 | 4 | 211 | cacgcuuggcugcggccggg | 26 | H. sapiens | 101 |
| 108097 | 4 | 231 | ugcgggcugaggccaugggc | 27 | H. sapiens | 102 |
| 108098 | 4 | 281 | gggucgcggcccucgagcca | 28 | H. sapiens | 103 |
| 108099 | 4 | 301 | cggcggcggcgggccugcgg | 29 | H. sapiens | 104 |

TABLE 3-continued

Sequence and position of preferred target segments
identified in diacylglycerol acyltransferase 1.

| SITE ID | TARGET SEQ ID NO | TARGET SITE | SEQUENCE | REV COMP OF SEQ ID | ACTIVE IN | SEQ ID NO |
|---------|------------------|-------------|----------|--------------------|-----------|-----------|
| 108101 | 4 | 401 | aaggacggagacgccggcgu | 31 | H. sapiens | 105 |
| 108102 | 4 | 421 | gggcagcggccacugggagc | 32 | H. sapiens | 106 |
| 108103 | 4 | 441 | ugaggugccaucgccugcag | 33 | H. sapiens | 107 |
| 108104 | 4 | 491 | agcaacuaccguggcauccu | 34 | H. sapiens | 108 |
| 108106 | 4 | 561 | agaaccucaucaaguauggc | 36 | H. sapiens | 109 |
| 108107 | 4 | 651 | ugguuauugcggccaauguc | 37 | H. sapiens | 110 |
| 108109 | 4 | 721 | gacggagcaggcgggacugc | 39 | H. sapiens | 111 |
| 108111 | 4 | 781 | agcggcugugucuuacugg | 41 | H. sapiens | 112 |
| 108112 | 4 | 831 | uggcgcugauggcgcacacc | 42 | H. sapiens | 113 |
| 108113 | 4 | 931 | gaagaaggccagcagugcug | 43 | H. sapiens | 114 |
| 108114 | 4 | 1021 | caccuugugcuacgagcuca | 44 | H. sapiens | 115 |
| 108116 | 4 | 1181 | gacauggacuacucacgcau | 46 | H. sapiens | 116 |
| 108117 | 4 | 1231 | caaucaccucaucuggcuca | 47 | H. sapiens | 117 |
| 108118 | 4 | 1281 | ugaaugccguggcugagcuc | 48 | H. sapiens | 118 |
| 108121 | 4 | 1671 | acuacgugcucaacuaugag | 51 | H. sapiens | 119 |
| 108122 | 4 | 1721 | gagggccuggcuucucacug | 52 | H. sapiens | 120 |
| 108123 | 4 | 1781 | gccucgagugcuggggaugg | 53 | H. sapiens | 121 |
| 108124 | 4 | 1801 | gccuggcugcacagcauccu | 54 | H. sapiens | 122 |
| 108125 | 4 | 1851 | augggcucuguccugcacc | 55 | H. sapiens | 123 |
| 108126 | 4 | 1881 | ggcgacagcaggccagacac | 56 | H. sapiens | 124 |
| 108127 | 4 | 1901 | agucugaugccagcugggag | 57 | H. sapiens | 125 |
| 108139 | 11 | 81 | gugcgggccgaagccauggg | 62 | M. musculus | 126 |
| 108141 | 11 | 191 | cgaggugcgagacgcggcug | 63 | M. musculus | 127 |
| 108142 | 11 | 232 | ggggugacgcgccggcuccg | 64 | M. musculus | 128 |
| 108143 | 11 | 281 | agacgggcggaccagcgugg | 65 | M. musculus | 129 |
| 108144 | 11 | 301 | gcgacggcuacugggaucug | 66 | M. musculus | 130 |
| 108145 | 11 | 321 | aggugccaucgucugcaaga | 67 | M. musculus | 131 |
| 108146 | 11 | 371 | caauuaucgugguauccuga | 68 | M. musculus | 132 |
| 108147 | 11 | 391 | auuggugugguugaugcug | 69 | M. musculus | 133 |
| 108148 | 11 | 411 | auccugaguaaugcaagguu | 70 | M. musculus | 134 |
| 108152 | 11 | 601 | cagagcagauggggcugcug | 73 | M. musculus | 135 |
| 108153 | 11 | 621 | cuacaugugguuaaccuggc | 74 | M. musculus | 136 |
| 108156 | 11 | 711 | gcucuggcaucauacuccau | 77 | M. musculus | 137 |
| 108157 | 11 | 771 | uggugccgccagcgaagggu | 78 | M. musculus | 138 |
| 108158 | 11 | 841 | agcaagcgugugagcuaucca | 79 | M. musculus | 139 |
| 108160 | 11 | 961 | ugcuacgacgaguucuugag | 81 | M. musculus | 140 |

TABLE 3-continued

Sequence and position of preferred target segments
identified in diacylglycerol acyltransferase 1.

| SITE ID | TARGET SEQ ID NO | TARGET SITE | SEQUENCE | REV COMP OF SEQ ID | ACTIVE IN | SEQ ID NO |
|---------|------------------|-------------|----------|---------------------|-----------|-----------|
| 108162 | 11 | 1061 | caaggauauggacuauucac | 83 | M. musculus | 141 |
| 108164 | 11 | 1161 | ugucucaaugcuguggcaga | 85 | M. musculus | 142 |
| 108165 | 11 | 1201 | gcgaguucuacagagauugg | 86 | M. musculus | 143 |
| 108166 | 11 | 1221 | uggaaugcugagucugucac | 87 | M. musculus | 144 |
| 108167 | 11 | 1271 | gcacaaguggugcaucagac | 88 | M. musculus | 145 |
| 108168 | 11 | 1301 | gccuaugcucagacauggca | 89 | M. musculus | 146 |
| 108169 | 11 | 1331 | gguggccaggacaggaguau | 90 | M. musculus | 147 |
| 108171 | 11 | 1471 | uccaagggaacuauggcaau | 91 | M. musculus | 148 |
| 108172 | 11 | 1491 | gcagcugugugggugacacu | 92 | M. musculus | 149 |
| 108173 | 11 | 1511 | caucauugggcaaccggugg | 93 | M. musculus | 150 |
| 108174 | 11 | 1531 | cugugcucauguauguccac | 94 | M. musculus | 151 |
| 108177 | 11 | 1621 | ccugggccuggaguucugga | 97 | M. musculus | 152 |

As these "preferred target segments" have been found by experimentation to be open to, and accessible for, hybridization with the antisense compounds of the present invention, one of skill in the art will recognize or be able to ascertain, using no more than routine experimentation, further embodiments of the invention that encompass other compounds that specifically hybridize to these preferred target segments and consequently inhibit the expression of diacylglycerol acyltransferase 1.

According to the present invention, antisense compounds include antisense oligomeric compounds, antisense oligonucleotides, ribozymes, external guide sequence (EGS) oligonucleotides, alternate splicers, primers, probes, and other short oligomeric compounds, that hybridize to at least a portion of the target nucleic acid.

Example 17

Western Blot Analysis of Diacylglycerol Aacyltransferase 1 Levels

Western blot analysis (immunoblot analysis) is carried out using standard methods. Cells are harvested 16-20 h after oligonucleotide treatment, washed once with PBS, suspended in Laemmli buffer (100 µL/well), boiled for 5 minutes and loaded on a 16% SDS-PAGE gel. Gels are run for 1.5 hours at 150 V, and transferred to membrane for western blotting. Appropriate primary antibody directed to diacylglycerol acyltransferase 1 is used, with a radiolabeled or fluorescently labeled secondary antibody directed against the primary antibody species. Bands are visualized using a PHOSPHORIMAGER™ instrument (Molecular Dynamics, Sunnyvale Calif.).

Example 18

Antisense Inhibition of Mouse Diacylglycerol Acyltransferase 1 Expression: Dose Response in b.END Cells In accordance with the present invention, six oligonucleotides targeted to mouse diacylglycerol acyltransferase 1, ISIS 191729 (SEQ ID NO: 63), ISIS 191731 (SEQ ID NO: 65), ISIS 191755 (SEQ ID NO: 88), ISIS 191756 (SEQ ID NO: 89), ISIS 191759 (SEQ ID NO: 91), and ISIS 191761 (SEQ ID NO: 93), were further investigated in a dose response study.

In the dose-response experiment, with mRNA levels as the endpoint, b.END cells were treated with ISIS 191729, ISIS 191731, ISIS 191755, ISIS 191756, ISIS 191759, or ISIS 191761 at doses of 1, 5, 10, 25, 50, and 100 nM oligonucleotide. Data were obtained by real-time quantitative PCR as described in other examples herein and are averaged from three experiments and are normalized to untreated control cells. The data are shown in Table 4.

TABLE 4

Inhibition of mouse diacylglycerol acyltransferase 1
mRNA levels by chimeric phosphorothioate oligonucleotides
having 2'-MOE wings and a deoxy gap: dose response

| | | Dose (nM) | | | | | |
|---------|-----------|----|----|----|----|----|-----|
| ISIS # | SEQ ID NO | 1 | 5 | 10 | 25 | 50 | 100 |
| | | % Inhibition | | | | | |
| 191729 | 63 | 26 | 62 | 78 | 80 | 83 | 83 |
| 191731 | 65 | 27 | 58 | 57 | 58 | 82 | 85 |
| 191755 | 88 | 41 | 59 | 72 | 75 | 83 | 79 |

TABLE 4-continued

Inhibition of mouse diacylglycerol acyltransferase 1 mRNA levels by chimeric phosphorothioate oligonucleotides having 2'-MOE wings and a deoxy gap: dose response

| ISIS # | SEQ ID NO | Dose (nM) | | | | | |
|---|---|---|---|---|---|---|---|
| | | 1 | 5 | 10 | 25 | 50 | 100 |
| | | | | % Inhibition | | | |
| 191756 | 89 | 13 | 39 | 59 | 65 | 81 | 75 |
| 191759 | 91 | 26 | 44 | 74 | 80 | 82 | 86 |
| 191761 | 93 | 23 | 63 | 71 | 80 | 85 | 87 |

From these data, it is evident that all of the oligonucleotides presented in Table 4 are capable of reducing diacylglycerol acyltransferase 1 mRNA levels in a dose-dependent manner.

Example 19

Effects of Antisense Inhibition of Diacylglycerol Acyltransferase 1 (ISIS 191729 and ISIS 191755) on Serum Glucose Levels—in vivo Studies Leptin is a hormone produced by fat cells that regulates appetite. Deficiencies in this hormone in both humans and non-human animals leads to obesity. ob/ob mice have a mutation in the leptin gene which results in obesity and hyperglycemia. As such, these mice are a useful model for the investigation of obesity and diabetes and treatments designed to treat these conditions. ob/ob mice have higher circulating levels of insulin and are less hyperglycemic than db/db mice, which harbor a mutation in the leptin receptor. In accordance with the present invention, the oligomeric compounds of the invention are tested in the ob/ob model of obesity and diabetes as potential agents to lower serum glucose levels.

Seven-week old male C57Bl/6J-Lep ob/ob mice (Jackson Laboratory, Bar Harbor, Me.) were fed a Purina 5015 diet (10-15% fat) and were evaluated over the course of 4 weeks for the effects of ISIS 191729 (SEQ ID No: 63) and ISIS 191755 (SEQ ID NO: 88) on serum glucose levels. Mice were dosed intraperitoneally twice a week with 25 mg/kg ISIS 191729 or ISIS 191755. Control animals received saline treatment twice per week for 4 weeks. Each group consisted of 8 animals. At the end of the treatment period, animals were sacrificed. Glucose levels in serum were measured using a YSI glucose analyzer (YSI Scientific, Yellow Springs, Ohio). Data are presented as the average of the 8 animals in each treatment group.

Both antisense oligonucleotides were able to reduce serum glucose levels relative to the saline-treated animals. Before any treatment was started (week 0), the measured glucose levels for each group of animals were 357, 368, and 346 mg/dL for the groups that would be treated with saline, ISIS 191729, and ISIS 191755, respectively. After two weeks, serum glucose levels were 300 and 278 mg/dL for ISIS 191729 and ISIS 191755, respectively, compared to 360 mg/dL for saline control. After four weeks of treatment, the serum glucose levels were further reduced to 224 and 188 mg/dL for ISIS 191729 and ISIS 191755, respectively, compared to 313 mg/dL for saline control.

These data indicate that ISIS 191729 and ISIS 191755 significantly reduced serum glucose levels in vivo. ISIS 191755 also caused no change in food intake or body weight, but reduced epididymal fat pad weight by 12%. (See Table 5 for a summary of in vivo data).

Example 20

Effects of Antisense Inhibition of Diacylglycerol Acyltransferase 1 (ISIS 191729 and ISIS 191755) on Diacylglycerol Acyltransferase 1 mRNA Levels in C57BL/6 Mice In a further embodiment, the mice described in Example 19 were evaluated for diacylglycerol acyltransferase 1 expression in liver and white adipose tissue. Following the four week treatment with twice weekly injections of 25 mg/kg ISIS 191729 (SEQ ID No: 63) and ISIS 191755 (SEQ ID NO: 88) the mice were sacrificed and liver and white adipose tissues were procured. Diacylglycerol acyltransferase 1 mRNA levels were quantitated by real-time PCR as described in other examples herein. Data presented are the average of the 8 animals in each treatment group.

The diacylglycerol acyltransferase 1 mRNA levels in white adipose tissue of the mice dosed with ISIS 191729 were 29% that of the saline-treated mice, and those dosed with ISIS 191755 were 16% that of the saline-treated mice. The diacylglycerol acyltransferase 1 mRNA levels in liver of the mice dosed with ISIS 191729 were 8% that of the saline-treated mice, and those dosed with ISIS 191755 were 4% that of the saline-treated mice.

It has been reported in the art that diacylglycerol acyltransferase 1 knockout mice demonstrate enhanced resistance to diet-induced obesity and this was not coupled with changes in energy expenditure or plasma glucose levels in ob/ob mice due to a compensatory upregulation of diacylglycerol acyltransferase 2 expression in white adipose tissue (Smith et al., Nat. Genet., 2000, 25, 87-90; Chen et al., J. Clin. Invest., 2002, 109, 1049-1055). The results of studies described herein using antisense compounds to transiently modulate diacylglycerol acyltransferase 1 mRNA levels are in contrast to those seen in the diacylglycerol acyltransferase 1 knockout studies. The results shown herein indicate that antisense oligonucleotides ISIS 191729 and ISIS 191755 are able to reduce diacylglycerol acyltransferase 1 mRNA levels, reduce serum glucose levels, and reduce fat pad weight while not affecting food intake and total body weight. (See Table 5 for a summary of in vivo data).

TABLE 5

Effects of ISIS 191729 or ISIS 191755 treatment on serum glucose levels and diacylglycerol acyltransferase 1 mRNA levels in ob/ob mice.

| Biological Marker Measured | | Treated with | | |
|---|---|---|---|---|
| | | Saline | ISIS 191729 | ISIS 191755 |
| | Week | | | |
| Glucose mg/dL | 0 | 357 | 368 | 346 |
| | 2 | 360 | 300 | 278 |
| | 4 | 313 | 224 | 188 |
| | Tissue | | | |
| mRNA % of control | Liver | 100 | 8 | 4 |
| | White adipose | 100 | 29 | 16 |

Example 21

Antisense Inhibition of Diacylglycerol Acyltransferase 1 in a Mouse Model of Diet-induced Obesity: a 7 Week Study The C57BL/6 mouse strain is reported to be susceptible to hyperlipidemia-induced atherosclerotic plaque formation.

Consequently, when these mice are fed a high-fat diet, they develop diet-induced obesity. Accordingly these mice are a useful model for the investigation of obesity and treatments designed to treat this condition. In this study, animals with diet-induced obesity were evaluated for diacylglycerol acytransferase 1 mRNA expression, circulating plasma glucose and insulin levels, serum tranaminase levels, food intake, body weight and metabolic rate.

Male C57BL/6 mice (7-weeks old) received a 60% fat diet for 8 weeks, after which mice were subcutaneously injected twice weekly with a 25 mg/kg dose of ISIS 191729 (SEQ ID NO: 63) or ISIS 141923 (CCTTCCCTGAAGGTTCCTCC; incorporated herein as SEQ ID NO: 153) for a period of 7 weeks. Control animals received subcutaneous saline injections twice weekly for 7 weeks. Each treatment group consisted of 8 mice.

ISIS 141923, a scrambled control oligonucleotide, is a chimeric oligonucleotides ("gapmer") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE) nucleotides. The internucleoside (backbone) linkages are phosphorothioate (P=S) throughout the oligonucleotide. All cytidine residues are 5-methylcytidines.

At study termination, 72 hours after the final injections, the animals were sacrificed and evaluated for diacylglycerol acyltransferase 1 mRNA expression in liver and white adipose tissue (WAT). RNA was isolated from liver and mRNA was quantitated as described herein. Diacylglycerol acyltransferase 1 mRNA levels from each treatment group (n=8) were averaged. Relative to saline-treated animals, treatment with ISIS 191729 resulted in an 86% and 77% reduction in diacylglycerol acyltransferase 1 mRNA levels in liver and WAT, respectively. Treatment with the scrambled control ISIS 141923 resulted in 9% decrease and a 23% increase in diacylglycerol acyltransferase 1 mRNA levels in liver and WAT, respectively. These results demonstrate that antisense compounds targeted to diacylglycerol acyltransferase 1 significantly reduced diacylglycerol acyltransferase 1 mRNA expression in liver and WAT in a model of diet-induced obesity.

Example 22

Effects of Antisense Inhibition of Diacylglycerol Acyltransferase 1 in a Mouse Model of Diet-induced Obesity: Circulating Glucose and Insulin Levels In a further embodiment, the mice described in Example 21 were evaluated for circulating glucose and insulin levels over the course of treatment with saline, ISIS 191729 (SEQ ID NO: (63) and ISIS 141923 (SEQ ID NO: 153). Measurements were taken prior to the beginning of the treatment period (week 0), and after 3 and 7 weeks of treatment. Glucose levels in serum were measured using a YSI glucose analyzer (YSI Scientific, Yellow Springs, Ohio) and insulin levels in serum were measure using an rat insulin-specific ELISA kit (ALPCO Diagnostics, Windham, N.H.). The levels of circulating glucose (mg/dL) and insulin (ng/mL) levels at the indicated time points are presented in Table 6 as the average result from each treatment group (n=8).

TABLE 6

Effects of antisense inhibition of diacylglycerol acyltransferase 1 on circulating glucose and insulin levels in a mouse model of diet-induced obesity

| Biological Marker Measured | Treatment | Weeks of treatment | | |
|---|---|---|---|---|
| | | 0 | 3 | 7 |
| Glucose levels mg/dL | Saline | 223 | 203 | 252 |
| | ISIS 141923 | 196 | 199 | 230 |
| | ISIS 191729 | 240 | 183 | 206 |
| Insulin levels ng/mL | Saline | 1.2 | 1.8 | 1.8 |
| | ISIS 141923 | 0.9 | 1.9 | 2.2 |
| | ISIS 191729 | 1.5 | 1.2 | 0.8 |

These results illustrate that inhibition of diacylglycerol acyltransferase 1 expression significantly decreased circulating insulin levels with respect to animals injected with ISIS 141923 or saline.

Example 23

Effects of Antisense Inhibition of Diacylglycerol Acyltransferase 1 in a Mouse Model of Diet-induced Obesity: Serum Transaminase Levels In a further embodiment, the mice described in Example 21 were evaluated for levels of the serum transaminases ALT and AST. Increases in these enzymes can indicate hepatotoxicity.

At study termination, seventy-two hours after the final injections, the animals treated with ISIS 191723 (SEQ ID NO: 63), ISIS 141923 (SEQ ID NO: 153) and saline were sacrificed and evaluated for ALT and AST levels in serum. ALT and AST were measured by routine methods at LabCorp clinical laboratories (San Diego, Calif.). These results are presented in Table 7 as the average result from each treatment group (n=8), in international units/L (IU/L).

TABLE 7

Effects of antisense inhibition of diacylglycerol acyltransferase 1 on serum transaminase in a mouse model of diet-induced obesity

| Treatment | Serum Transaminases IU/L | |
|---|---|---|
| | AST | ALT |
| Saline | 84 | 51 |
| ISIS 141923 | 89 | 43 |
| ISIS 191729 | 179 | 132 |

In this animal model, hepatotoxicity is defined as an ALT or AST level above twice that of the control. These results demonstrate that ISIS 191729 resulted in an elevation of ALT and AST levels to approximately twice the level of the control.

Example 24

Effects of Antisense Inhibition of Diacylglycerol Acyltransferase 1 in a Mouse Model of Diet-induced Obesity: Body Weight, Food Intake and Metabolic Rate In a further embodiment, the mice described in Example 21 were evaluated for body weight, food intake and metabolic rate during the course of treatment with ISIS 191729 (SEQ ID NO: 63), ISIS 141923 (SEQ ID NO: 153) and saline. Body weight and food intake were recorded weekly throughout the 7 week study period, and were found not to change significantly among the 3 treatment groups. At week 4, metabolic rates were measured by placing the mice a metabolic chamber for indirect calorimetry measurements (Oxymax; Columbus Instruments International, Columbus, Ohio) for a period of 24 hours. Relative to saline- or ISIS 141923-treated mice, no significant differences were found in the metabolic rates of mice treated with ISIS 191729. These results demonstrate that treatment with antisense compounds targeted to diacylglycerol acyltransferase 1 did not significantly affect body weight, food intake or metabolic rate in a mouse model of diet-induced obesity.

Example 25

Antisense Inhibition of Diacylglycerol Acyltransferase 1 mRNA in a Mouse Model of Diet-induced Obesity: a 5 Week Study The C57BL/6 mouse strain is reported to be susceptible to hyperlipidemia-induced atherosclerotic plaque formation. Consequently, when these mice are fed a high-fat diet, they develop diet-induced obesity. Accordingly these mice are a useful model for the investigation of obesity and treatments designed to treat this conditions. A 5 week study was performed to further investigate the effects of antisense inhibition of diacylglycerol acyltransferase 1 in a mouse model of diet-induced obesity. In this study, mice receiving treatment with antisense compounds targeted to diacylglycerol acyltransferase 1 were evaluated for target mRNA expression, tolerance to glucose and insulin challenges, fasting serum insulin levels, serum free fatty acids, serum triglycerides and liver tissue triglycerides.

Male C57BL/6 mice (7-weeks old) received a 60% fat diet for 5 weeks, after which mice were subcutaneously injected twice weekly with a 25 mg/kg dose of ISIS 141923 (SEQ ID NO: 153) or ISIS 191729 (SEQ ID NO: 63) for a period of 5 weeks. Control animals received subcutaneous saline injections twice per week for 5 weeks. Each treatment group consisted of 8 mice.

At study termination, 72 hours after the final injections, the animals were sacrificed and evaluated for diacylglycerol acyltransferase 1 mRNA expression in liver and white adipose tissue (WAT). RNA was isolated from liver and WAT and mRNA was quantitated as described herein. Diacylglycerol acyltransferase 1 mRNA levels from each treatment group (n=8) were averaged. Relative to saline-treated animals, treatment with ISIS 191729 resulted in a 90% and 82% reduction in diacylglycerol acyltransferase 1 mRNA levels in liver and WAT, respectively. The mice treated with the scrambled control oligonucleotide ISIS 141923 exhibited a 16% increase and 25% reduction in diacylglycerol acyltransferase 1 mRNA levels in liver and WAT, respectively. These results demonstrate that, as was observed in the 7 week study in a mouse model of diet-induced obesity, ISIS 191729 significantly reduced diacylglycerol acyltransferase 1 mRNA expression in liver and WAT.

Example 26

Effects of Antisense Inhibition of Diacylglycerol Acyltransferase 1 on Serum Insulin Levels Following a 4 Hour Fast In a further embodiment, after 4 weeks of treatment with saline, ISIS 191729 (SEQ ID NO: 63) or ISIS 141923 (SEQ ID NO: 153) the mice described in Example 25 were evaluated for serum insulin levels following a 4 hour fast. Serum insulin levels were measured using an insulin-specific ELISA kit (American Laboratory Products, Windham, N.H.). Mice treated with ISIS 191729 had lower fasting serum insulin levels (.52 ng/ml) when compared to saline-treated (1.11 ng/ml) or ISIS 141923-treated (0.95 ng/ml) mice. Results presented are the average result from each treatment group (n=8). These results demonstrate that antisense compounds targeted to diacylglycerol acyltransferase 1 significantly decreased fasting serum insulin levels in a mouse model of diet-induced obesity.

Example 27

Effects of Antisense Inhibition of Diacylglycerol Acyltransferase 1 in a Mouse Model of Diet-induced Obesity: Insulin and Glucose Tolerance Tests In a further embodiment, the mice described in Example 25 were evaluated on their performance on insulin and glucose tolerance tests. Through measurement of glucose levels following the injection of a bolus of glucose or insulin, tolerance tests assess the physiological response to an insulin or glucose challenge.

Glucose tolerance tests (GTT) were performed after 5 weeks of treatment with saline, ISIS 141923 (SEQ ID NO: 153) ISIS 191729 (SEQ ID NO: 63). To provide a baseline glucose level, blood glucose levels were measured before the glucose challenge. Mice received intraperitoneal injections of glucose at a dose of 1 g/kg. Blood glucose levels were measured 15, 30, 60, 90 and 120 minutes post-challenge using an Olympus Clinical Analyzer (Olympus America, Melville, N.H.).

Insulin tolerance tests (ITT) were performed after 4 weeks of treatment with saline, ISIS 141923 or ISIS 191729. To provide a baseline insulin level, blood insulin levels were measured before the glucose challenge. Mice received intraperitoneal injections of insulin at a dose of 0.5 units/kg. Blood glucose levels were measured 15, 30, 60, 90 and 120 minutes post-challenge using an Olympus Clinical Analyzer (Olympus America, Melville, N.H.).

The results are presented in Table 8 as the average result from each treatment group (n=8). Saline-treated mice served as the control to which insulin and glucose levels were compared.

TABLE 8

Effects of antisense inhibition of diacylglycerol acyltransferase 1 on insulin and glucose tolerance tests

| | | Glucose, mg/dL at intervals after challenge | | | | | |
|---|---|---|---|---|---|---|---|
| | Treatment | 0 min | 15 min | 30 min | 60 min | 90 min | 120 min |
| Insulin Tolerance Test | Saline | 178 | 184 | 131 | 140 | 188 | 217 |
| | ISIS 141923 | 171 | 168 | 121 | 133 | 177 | 213 |
| | ISIS 191729 | 160 | 148 | 114 | 113 | 140 | 160 |
| Glucose Tolerance Test | Saline | 103 | 319 | 345 | 292 | 252 | 220 |
| | ISIS 141923 | 113 | 313 | 345 | 276 | 211 | 193 |
| | ISIS 191729 | 94 | 267 | 304 | 235 | 187 | 164 |

These results demonstrate that in animals treated with ISIS 191729, but not those treated with saline or ISIS 141923, glucose levels returned to and did not exceed baseline values within two hours following the insulin challenge. For both insulin and glucose tolerance tests, a graph of the data presented in Table 8 demonstrates an improved area under the curve following treatment with ISIS 191729, revealing an improved performance on glucose and insulin tolerance tests.

Example 28

Effects of Antisense Inhibition of Diacylglycerol Acyltransferase 1 in a Mouse Model of Diet-induced Obesity: Serum Triglyceride, Liver Triglyceride, and Free Fatty Acid Levels In a further embodiment, the mice described in Example 25 were evaluated for the effects of saline, ISIS 141923 (SEQ ID NO: 153) and ISIS 191729 (SEQ ID NO: 63) treatment on serum triglyceride, liver triglyceride, and free fatty acid levels.

Animals were subjected to a 4 hour fast after the 5 week treatment period for measurement of serum free fatty acids. Serum free fatty acids (4 hour fasting, mEq/L) were measured using a kit for non-esterified free fatty acids (Wako Chemicals, Richmond, Va.). Data are presented in Table 9 as the average of 8 animals in a treatment group.

Following sacrifice of the animals, 72 hours after the last injection, serum was collected and serum triglycerides (mg/dl) were measured by routine methods at LabCorp clinical laboratories (San Diego, Calif.). Liver tissue was procured and liver triglyceride (mg/g wet tissue) levels were measured using a Triglyceride GPO Assay from Roche Diagnostics (Indianapolis, Ind.). Liver triglyceride levels are used to assess hepatic steatosis, or clearing of lipids from the liver. These results are presented in Table 9 as the average result from 8 animals in a treatment group.

TABLE 9

Effects of antisense inhibition of diacylglycerol acyltransferase 1 on serum triglyceride, liver triglyceride, and free fatty acid levels

| | Biological Marker Measured | | |
|---|---|---|---|
| | Free Fatty Acids | Triglycerides | |
| Treatment | Serum mEq/L | Serum mg/dL | Liver mg/g |
| Saline | 0.74 | 85 | 71 |
| ISIS 141923 | 0.68 | 80 | 58 |
| ISIS 191729 | 0.56 | 56 | 64 |

These results demonstrate that antisense compounds targeted to diacylglycerol acyltransferase 1 reduced circulating triglyceride levels in a mouse model of diet-induced obesity. The data are also suggestive of a drop in liver triglyceride and free fatty acid levels in a mouse model of diet-induced obesity.

The data obtained in a mouse model of diet-induced obesity and presented herein demonstrate that treatment with ISIS 191729 significantly decreased in diacylglycerol acyltransferase 1 mRNA expression in both liver and white adipose tissue. The inhibition of target mRNA expression resulted in a reduction in circulating insulin and triglyceride levels and an improved area under the curve following glucose and insulin tolerance tests. The data also suggest a reduction in circulating free fatty acids and liver triglycerides. These effects were independent of changes in food intake, metabolic rate or body weight. Together, these data reveal that ISIS 191729 treatment improved the overall metabolic rate and cardiovascular risk profile in a model of diet-induced obesity. Moreover, the effects of a transient reduction in diacylglycerol acyltransferase 1 expression, described herein, were in contrast to findings in the diacylglycerol transferase 1 mouse gene disruption model, where said mice are resistant to diet-induced obesity and protected against insulin resistance.

Example 29

Antisense Inhibition of Rat Diacylglycerol Acyltransferase 1 Expression by Chimeric Phosphorothioate Oligonucleotides Having 2'-MOE Wings and a Deoxy Gap In accordance with the present invention, a series of antisense compounds was designed to target different regions of the rat diacylglycerol acyltransferase 1 RNA, using published sequence information (GenBank accession number AF296131.1, incorporated herein as SEQ ID NO: 154). The compounds are shown in Table 10. "Target site" indicates the first (5'-most) nucleotide number on the particular target sequence to which the compound binds. All compounds in Table 10 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE) nucleotides. The internucleoside (backbone) linkages are phosphorothioate (P=S) throughout the oligonucleotide. All cytidine residues are 5-methylcytidines.

The compounds were analyzed for their effect on rat diacylglycerol acyltransferase 1 mRNA levels by quantitative real-time PCR as described in other examples herein. Probes and primers to rat diacylglycerol acyltransferase 1 were designed to hybridize to a rat diacylglycerol acyltransferase 1 sequence, using published sequence information (GenBank accession number AF296131.1, incorporated herein as SEQ ID NO: 154). For rat diacylglycerol acyltransferase 1 the PCR primers were:

forward primer: CAGACCAGCGTGGGCG (SEQ ID NO: 155) reverse primer: GAACAAAGAGTCTTGCAGAC-GATG (SEQ ID NO: 156) and the PCR probe was: FAM-CGGCCACTGGGAGCTGAGGTG-TAMRA (SEQ ID NO: 157) where FAM is the fluorescent reporter dye and TAMRA is the quencher dye. Rat target gene quantities were normalized by quantifying total RNA using RiboGreen™ RNA quantification reagent.

Data are averages from three experiments in which rat primary hepatocytes were treated with 50 nM of the antisense oligonucleotides of the present invention. Data, shown in Table 10, are presented as percent inhibition normalized to untreated control samples.

TABLE 10

Inhibition of rat diacylglycerol acyltransferase 1 mRNA levels by chimeric phosphorothioate oligonucleotides having 2'-MOE wings and a deoxy gap

| ISIS # | REGION | TARGET SEQ ID NO | TARGET SITE | Sequence | % INHIB | SEQ ID NO |
|---|---|---|---|---|---|---|
| 191726 | 5'UTR | 11 | 1 | ctcgtcgcggcccaatcttc | 0 | 61 |
| 191733 | Coding | 11 | 261 | tcttgcagacgatggcacct | 68 | 67 |
| 327788 | Start Codon | 154 | 24 | TCGCCCATGGCTTCGGCCCG | 0 | 158 |
| 327789 | Coding | 154 | 44 | AGCTTCCCGCGCCTCCGCGG | 0 | 159 |
| 327790 | Coding | 154 | 61 | GGTCCTGCGACGCCGAGAGC | 0 | 160 |
| 327791 | Coding | 154 | 82 | CTGGACGGAAACCCGCGAGC | 0 | 161 |
| 327792 | Coding | 154 | 103 | TACCTTGGGCCCACTACCTC | 0 | 162 |
| 327793 | Coding | 154 | 121 | TCGCACCTCGTCCTCTTCTA | 0 | 163 |
| 327794 | Coding | 154 | 170 | GAGCCGGCGCGTCACCCCCG | 0 | 164 |
| 327795 | Coding | 154 | 191 | TATGGGCTGGAGCCGGAGCC | 0 | 165 |
| 327796 | Coding | 154 | 196 | CCGGGTATGGGCTGGAGCCG | 0 | 166 |
| 327797 | Coding | 154 | 225 | TCGCCCACGCTGGTCTGCCG | 63 | 167 |
| 327798 | Coding | 154 | 248 | GGCACCTCAGCTCCCAGTGG | 64 | 168 |
| 327799 | Coding | 154 | 282 | CTGTCTGAGCTGAACAAAGA | 0 | 169 |
| 327800 | Coding | 154 | 309 | AGGATACCACGGTAATTGCT | 0 | 170 |
| 327801 | Coding | 154 | 318 | CACCAATTCAGGATACCACG | 0 | 171 |
| 327802 | Coding | 154 | 345 | GCATTACTCAGGATCAGCAT | 0 | 172 |
| 327803 | Coding | 154 | 359 | CTAAAGATAACCTTGCATTA | 0 | 173 |
| 327804 | Coding | 154 | 374 | ACTTGATAAGATTCTCTAAA | 0 | 174 |
| 327805 | Coding | 154 | 389 | CCACCAGGATGCCATACTTG | 0 | 175 |
| 327806 | Coding | 154 | 393 | GGATCCACCAGGATGCCATA | 0 | 176 |
| 327807 | Coding | 154 | 415 | AAACAGAGACACCACCTGGA | 0 | 177 |
| 327808 | Coding | 154 | 463 | GGATGCAATGATCAAGCATG | 0 | 178 |
| 327809 | Coding | 154 | 477 | ACAATAAAGATATTGGATGC | 0 | 179 |
| 327810 | Coding | 154 | 499 | CTTCTCAATCTGAAATGTAG | 0 | 180 |
| 327811 | Coding | 154 | 504 | AGGCGCTTCTCAATCTGAAA | 0 | 181 |
| 327812 | Coding | 154 | 527 | GCTCTGTCAGGGCACCCACT | 0 | 182 |
| 327813 | Coding | 154 | 537 | AGCCCCATCTGCTCTGTCAG | 20 | 183 |

TABLE 10-continued

Inhibition of rat diacylglycerol acyltransferase 1 mRNA levels by chimeric phosphorothioate oligonucleotides having 2'-MOE wings and a deoxy gap

| ISIS # | REGION | TARGET SEQ ID NO | TARGET SITE | Sequence | % INHIB | SEQ ID NO |
|---|---|---|---|---|---|---|
| 327814 | Coding | 154 | 552 | ACCACATGTAGCAGCAGCCC | 17 | 184 |
| 327815 | Coding | 154 | 579 | GGGAAGCAGATAATTGTGGC | 0 | 185 |
| 327816 | Coding | 154 | 594 | AAGGCCACAGCTGCTGGGAA | 0 | 186 |
| 327817 | Coding | 154 | 607 | AGACTCAACCAGTAAGGCCA | 25 | 187 |
| 327818 | Coding | 154 | 616 | TGGAGTGATAGACTCAACCA | 2 | 188 |
| 327819 | Coding | 154 | 649 | GGAGTATGATGCCAGAGCAA | 0 | 189 |
| 327820 | Coding | 154 | 661 | GAGGAAGATGATGGAGTATG | 0 | 190 |
| 327821 | Coding | 154 | 679 | CCGGTAGGAAGAAAGCTTGA | 0 | 191 |
| 327822 | Coding | 154 | 709 | CCTTCGCTGGCGGCACCACA | 29 | 192 |
| 327823 | Coding | 154 | 726 | ACAGCTTTGGCCTTGACCCT | 0 | 193 |
| 327824 | Coding | 154 | 744 | ACCTTCTTCCCTGCAGACAC | 0 | 194 |
| 327825 | Coding | 154 | 758 | CAGCAGCCCCACTGACCTTC | 6 | 195 |
| 327826 | Coding | 154 | 779 | GATAGCTTACAGTGTTCTGG | 0 | 196 |
| 327827 | Coding | 154 | 797 | GGTAGGTCAGGTTGTCCGGA | 0 | 197 |
| 327828 | Coding | 154 | 806 | AGAGATCTCGGTAGGTCAGG | 0 | 198 |
| 327829 | Coding | 154 | 819 | AAGATGAAGTAATAGAGATC | 0 | 199 |
| 327830 | Coding | 154 | 833 | ACAAAGTAGGAGCAAAGATG | 0 | 200 |
| 327831 | Coding | 154 | 849 | AAGTTGAGTTCATAACACAA | 0 | 201 |
| 327832 | Coding | 154 | 912 | AAAAAGAGCATCTCAAGAAC | 0 | 202 |
| 327833 | Coding | 154 | 934 | CAGCCCCACTTGAAGCTGGG | 0 | 203 |
| 327834 | Coding | 154 | 949 | CATCCACTGCTGGATCAGCC | 0 | 204 |
| 327835 | Coding | 154 | 970 | GGAGTTCTGGATAGTAGGGA | 0 | 205 |
| 327836 | Coding | 154 | 981 | AAGGGCTTCATGGAGTTCTG | 0 | 206 |
| 327837 | Coding | 154 | 991 | CATGTCCTTGAAGGGCTTCA | 0 | 207 |
| 327838 | Coding | 154 | 1030 | CGCCAGCTTTAAGAGACGCT | 0 | 208 |
| 327839 | Coding | 154 | 1103 | GCTCTGCCACAGCATTGAGA | 0 | 209 |
| 327840 | Coding | 154 | 1131 | TAGAACTCGCGGTCTCCAAA | 0 | 210 |
| 327841 | Coding | 154 | 1162 | GGTGACAGACTCAGCATTCC | 0 | 211 |
| 327842 | Coding | 154 | 1186 | GATATTCCAGTTCTGCCAAA | 0 | 212 |
| 327843 | Coding | 154 | 1212 | TGTCTGATGCACCACTTGTG | 0 | 213 |
| 327844 | Coding | 154 | 1271 | AGACCCCAGTCCTGGCCATC | 22 | 214 |
| 327845 | Coding | 154 | 1299 | TACTCATGAAAGAAAGCTGA | 0 | 215 |
| 327846 | Coding | 154 | 1351 | CATTGCTGTGAATGCCCAAA | 0 | 216 |
| 327847 | Coding | 154 | 1380 | ACAATCCAGGCCAGTGGGAC | 0 | 217 |
| 327848 | Coding | 154 | 1414 | TGCATTGCCATAGTTCCCTT | 0 | 218 |

TABLE 10-continued

Inhibition of rat diacylglycerol acyltransferase 1 mRNA levels by chimeric phosphorothioate oligonucleotides having 2'-MOE wings and a deoxy gap

| ISIS # | REGION | TARGET SEQ ID NO | TARGET SITE | Sequence | % INHIB | SEQ ID NO |
|--------|--------|------------------|-------------|----------|---------|-----------|
| 327849 | Coding | 154 | 1442 | GCCCAATGATGAGTGTCACC | 0 | 219 |
| 327850 | Coding | 154 | 1477 | GTAGTCGTGGACATACATGA | 0 | 220 |
| 327851 | Stop Codon | 154 | 1524 | TTGGCAGTAGCTCATGCCCC | 0 | 221 |
| 327852 | Stop Codon | 154 | 1531 | CTGGCCTTTGGCAGTAGCTC | 12 | 222 |
| 327853 | 3'UTR | 154 | 1562 | CCTCCAGAACTCCAGGCCCA | 55 | 223 |
| 327854 | 3'UTR | 154 | 1637 | ATCCCCAAGAGCAGGAGTAG | 0 | 224 |
| 327855 | 3'UTR | 154 | 1670 | CCCAGCACTGGCTCAACCAG | 0 | 225 |
| 327856 | 3'UTR | 154 | 1702 | TTGATATCCTAAGCCCCTGG | 0 | 226 |
| 327857 | 3'UTR | 154 | 1727 | TTTTTTTTTTTTAGATAGCT | 0 | 227 |

As shown in Table 10, SEQ ID NOs 67, 167, 168, 183, 184, 187, 192, 214, 222 and 223 demonstrated at least 10% inhibition of rat diacylglycerol acyltransferase 1 in this assay.

SEQ ID NOs 61 and 67 are cross-species antisense oligonucleotides that target both mouse and rat diacylglycerol acyltransferase 1.

Example 30

Antisense Inhibition of Rat Diacylglycerol Acyltransferase 1 by Chimeric Phosphorothioate Oligonucleotides Having 2'-MOE Wings and a Deoxy Gap: Dose Response In a further embodiment, six oligonucleotides were selected for further investigation in a dose response experiment in rat primary hepatocytes. Rat primary hepatocytes were treated with 1, 5, 10, 25, 50 and 100 nM of ISIS 191733 (SEQ ID NO: 67), ISIS 327798 (SEQ ID NO: 168), ISIS 327814 (SEQ ID NO: 184), ISIS 327817 (SEQ ID NO: 187), ISIS 327822 (SEQ ID NO: 192), ISIS 327844 (SEQ ID NO: 214) and ISIS 327853 (SEQ ID NO: 223). Untreated cells served as a control. Target mRNA levels were measured by real-time PCR as described in other examples herein. Data, presented in Table 11, are the average of three experiments and are normalized to untreated control samples.

TABLE 11

Inhibition of rat diacylglycerol acyltransferase 1 by chimeric phosphorothioate oligonucleotides: dose response

| ISIS # | SEQ ID NO | Dose of oligonucleotide | | | | | |
|--------|-----------|---|----|----|----|-----|-----|
| | | 5 | 10 | 25 | 50 | 100 | 200 |
| | | % Inhibition | | | | | |
| 191733 | 67 | 20 | 53 | 77 | 91 | 97 | 99 |
| 327798 | 168 | 0 | 13 | 68 | 88 | 96 | 98 |
| 327814 | 184 | 0 | 5 | 37 | 72 | 80 | 89 |
| 327817 | 187 | 0 | 0 | 0 | 57 | 76 | 87 |
| 327822 | 192 | 0 | 32 | 52 | 73 | 88 | 95 |
| 327844 | 214 | 0 | 0 | 17 | 66 | 71 | 87 |
| 327853 | 223 | 0 | 0 | 48 | 70 | 80 | 92 |

As demonstrated in Table 11, all 7 antisense oligonucleotides tested were able to inhibit the expression of diacylglycerol acyltransferase 1 in a dose-dependent manner.

All documents referenced in this specification are incorporated by reference.

What is claimed is:

1. A compound 12 to 80 nucleobases in length targeted to at least an 8 nucleobase portion of nucleotides 401 to 460 of SEQ ID NO: 4 encoding diacylglycerol acyltransferase 1, wherein said compound is at least 95% complementary to SEQ ID NO:4.

2. The compound of claim 1 comprising 12 to 50 nucleobases in length.

3. The compound of claim 2 comprising 15 to 30 nucleobases in length.

4. The compound of claim 1 comprising an oligonucleotide.

5. The compound of claim 4 comprising an antisense oligonucleotide.

6. The compound of claim 4 comprising a DNA oligonucleotide.

7. The compound of claim 4 comprising an RNA oligonucleotide.

8. The compound of claim 4 comprising a chimeric oligonucleotide.

9. The compound according to claim 8, wherein said chimeric oligonucleotide is 20 nucleotides in length, comprising ten 2'-deoxynucleotides, flanked on each side by five 2'-O-methoxyethyl nucleotides, wherein the internucleoside linkages are phosphorothioate, and all cytidine residues are 5-methylcytidines.

10. The compound of claim 4 wherein at least a portion of said compound hybridizes with RNA to form an oligonucleotide-RNA duplex.

11. The compound of claim 1 having at least one modified internucleoside linkage, sugar moiety, or nucleobase.

12. The compound of claim 1 having at least one 2'-O-methoxyethyl sugar moiety.

13. The compound of claim 1 having at least one phosphorothioate internucleoside linkage.

14. The compound of claim 1 having at least one 5-methylcytosine.

15. A method of inhibiting the expression of diacylglycerol acyltransferase 1 in cells or tissues comprising contacting said cells or tissues with the compound of claim 1 so that expression of diacylglycerol acyltransferase 1 is inhibited.

16. A kit or assay device comprising the compound of claim 1.

17. A method of treating an animal having a disease or condition associated with diacylglycerol acyltransferase 1 comprising administering to said animal a therapeutically or prophylactically effective amount of the compound of claim 1 so that expression of diacylglycerol acyltransferase 1 is inhibited.

18. The method of claim 17 wherein the condition involves abnormal lipid metabolism.

19. The method of claim 17 wherein the condition involves abnormal cholesterol metabolism.

20. The method of claim 17 wherein the condition is atherosclerosis.

21. The method of claim 17 wherein the condition is an abnormal metabolic condition.

22. The method of claim 21 wherein the abnormal metabolic condition is hyperlipidemia.

23. The method of claim 17 wherein the disease is diabetes.

24. The method of claim 23 wherein the diabetes is Type 2 diabetes.

25. The method of claim 17 wherein the condition is obesity.

26. The method of claim 17 wherein the disease is cardiovascular disease.

27. A method of modulating glucose levels in an animal comprising administering to said animal the compound of claim 1.

28. The method of claim 27 wherein the animal is a human.

29. The method of claim 27 wherein the glucose levels are plasma glucose levels.

30. The method of claim 27 wherein the glucose levels are serum glucose levels.

31. The method of claim 27 wherein the animal is a diabetic animal.

32. A method of delaying the onset of a disease or condition associated with diacylglycerol acyltransferase 1 in an animal comprising administering to said animal a therapeutically effective amount of the compound of claim 1.

33. The method of claim 32 wherein the animal is a human.

34. The method of claim 32 wherein the condition is an abnormal metabolic condition.

35. The method of claim 34 wherein the abnormal metabolic condition is hyperlipidemia.

36. The method of claim 32 wherein the disease is diabetes.

37. The method of claim 36 wherein the diabetes is Type 2 diabetes.

38. The method of claim 32 wherein the condition is obesity.

39. A method of modulating cholesterol levels in an animal comprising administering to said animal the compound of claim 1.

40. The method of claim 39 wherein the animal is a human.

41. The method of claim 39 wherein the cholesterol levels are plasma cholesterol levels.

42. The method of claim 39 wherein the cholesterol levels are serum cholesterol levels.

43. A method of lowering triglyceride levels in an animal comprising administering to said animal the compound of claim 1.

44. The method of claim 43 wherein the animal is a human.

45. The method of claim 43 wherein the triglyceride levels are plasma triglyceride levels.

46. The method of claim 43 wherein the triglyceride levels are serum triglyceride levels.

47. A method of reducing serum glucose levels in an animal comprising contacting said animal with the compound of claim 1.

48. A method of reducing diacylglycerol acyltransferase 1 levels in the liver of an animal comprising contacting said animal with the compound of claim 1.

49. A method of reducing circulating insulin levels in an animal comprising contacting said animal with the compound of claim 1.

50. The method according to claim 49, wherein said reduction is sustained over at least 5 weeks.

51. A method of decreasing fasted serum insulin levels in an animal comprising contacting said animal with the compound of claim 1.

52. A method of reducing serum glucose levels in an animal comprising contacting said animal with the compound of claim 1.

53. A method of improving an animal's performance on glucose tolerance tests and insulin tolerance tests comprising contacting said animal with the compound of claim 1.

54. A method of reducing circulating triglycerides in an animal comprising contacting said animal with the compound of claim 1.

55. A method of reducing liver triglycerides in an animal comprising contacting said animal with the compound of claim 1.

56. A method of reducing free fatty acids in the liver of an animal comprising contacting said animal with the compound of claim 1.

57. The compound of claim 1 wherein the compound comprises at least and 8 nucleobase portion of SEQ ID NO: 31, 32 or 33.

58. The compound of claim 1, wherein the compound consists of SEQ ID NO: 31, 32, or 33.

59. The compound of claim 1 wherein the compound inhibits diacylglycerol acyltransferase 1 expression by at least 60%.

60. The compound of claim 57, wherein the oligonucleotide comprises:
   a gap segment consisting of linked deoxynucleosides;
   a 5' wing segment consisting of linked nucleosides;
   a 3' wing segment consisting of linked nucleosides;
   wherein the gap segment is positioned between the 5' wing segment and the 3' wing segment and wherein each nucleoside of each wing segment comprises a modified sugar.

61. The compound of claim 60, wherein the oligonucleotide comprises:
   a gap segment consisting of ten linked deoxynucleosides;
   a 5' wing segment consisting of five linked nucleosides;
   a 3' wing segment consisting of five linked nucleosides;
   wherein the gap segment is positioned between the 5' wing segment and the 3' wing segment, wherein each nucleoside of each wing segment comprises a 2'-O-methoxyethyl sugar; and wherein each internucleoside linkage is a phosphorothioate linkage.

62. A compound comprising an oligonucleotide consisting of the nucleobase sequence of SEQ ID NO: 33, wherein the oligonucleotide comprises:
   a gap segment consisting of linked deoxynucleosides;
   a 5' wing segment consisting of linked nucleosides;
   a 3' wing segment consisting of linked nucleosides;
   wherein the gap segment is positioned between the 5' wing segment and the 3' wing segment and wherein each nucleoside of each wing segment comprises a modified sugar.

63. The compound of claim 62, wherein the oligonucleotide comprises:
   a gap segment consisting of ten linked deoxynucleosides;
   a 5' wing segment consisting of five linked nucleosides;
   a 3' wing segment consisting of five linked nucleosides;
   wherein the gap segment is positioned between the 5' wing segment and the 3' wing segment, wherein each nucleoside of each wing segment comprises a 2'-O-methoxyethyl sugar; and wherein each internucleoside linkage is a phosphorothioate linkage.

64. A composition comprising an oligonucleotide consisting of 12 to 80 linked nucleosides and having a nucleobase sequence comprising at least 8 contiguous nucleobases of the nucleobase sequence recited in SEQ ID NO: 33 or a salt thereof and a pharmaceutically acceptable carrier or diluents.

65. A method of inhibiting the expression of diacylglycerol acyltransferase 1 in a human comprising administering to said human the composition of claim 62.

* * * * *